(12) United States Patent
Stamatoyannopoulos et al.

(10) Patent No.: US 10,590,433 B2
(45) Date of Patent: Mar. 17, 2020

(54) GENOMIC INSULATOR ELEMENTS AND USES THEREOF

(71) Applicant: UNIVERSITY OF WASHINGTON, Seattle, WA (US)

(72) Inventors: George Stamatoyannopoulos, Seattle, WA (US); John Stamatoyannopoulos, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 15/126,115

(22) PCT Filed: Mar. 13, 2015

(86) PCT No.: PCT/US2015/020369
§ 371 (c)(1),
(2) Date: Sep. 14, 2016

(87) PCT Pub. No.: WO2015/138852
PCT Pub. Date: Sep. 17, 2015

(65) Prior Publication Data
US 2017/0175136 A1 Jun. 22, 2017

Related U.S. Application Data

(60) Provisional application No. 62/068,226, filed on Oct. 24, 2014, provisional application No. 61/953,419, filed on Mar. 14, 2014.

(51) Int. Cl.
| | | |
|---|---|---|
| *C12N 15/86* | (2006.01) | |
| *C12N 15/10* | (2006.01) | |
| *C12N 15/85* | (2006.01) | |
| *C12N 15/113* | (2010.01) | |
| *A61K 48/00* | (2006.01) | |
| *C12Q 1/6876* | (2018.01) | |

(52) U.S. Cl.
CPC ............ *C12N 15/86* (2013.01); *A61K 48/005* (2013.01); *C12N 15/113* (2013.01); *C12Q 1/6876* (2013.01); *C12N 2310/141* (2013.01); *C12N 2740/15043* (2013.01); *C12N 2740/16043* (2013.01); *C12N 2830/40* (2013.01)

(58) Field of Classification Search
None
See application file for complete search history.

(56) References Cited

U.S. PATENT DOCUMENTS

| | | | |
|---|---|---|---|
| 5,610,053 A | 3/1997 | Chung et al. | |
| 8,709,754 B2 | 4/2014 | Krumm et al. | |
| 8,828,718 B2 * | 9/2014 | Cohen-Haguenauer | C12N 15/86 435/320.1 |
| 2010/0022006 A1 | 1/2010 | Kim et al. | |
| 2010/0144543 A1 | 6/2010 | Witcher et al. | |
| 2011/0294114 A1 | 12/2011 | Van Der Loo et al. | |
| 2011/0294873 A1 * | 12/2011 | Mermod | C07K 14/4702 514/44 R |
| 2012/0115227 A1 | 5/2012 | Cohen-Haguenauer et al. | |
| 2012/0178641 A1 | 7/2012 | Stamatoyannopoulos | |
| 2015/0079123 A1 * | 3/2015 | Berkower | A61K 39/21 424/188.1 |

FOREIGN PATENT DOCUMENTS

| | | |
|---|---|---|
| WO | 9535319 A1 | 12/1995 |
| WO | 0102553 A2 | 1/2001 |

OTHER PUBLICATIONS

Aiuti et al., "Gene Therapy for Immunodeficiency Due to Adenosine Deaminase Deficiency", N. Engl. J. Med. 360(5):447-458 (2009).
Aiuti et al., "Multilineage hematopoietic reconstitution without clonal selection in ADA-SCID patients treated with stem cell gene therapy", J. Clin. Invest. 117(8):2233-2240 (2007).
Aker et al., "Extended Core Sequences from the cHS4 Insulator Are Necessary for Protecting Retroviral Vectors from Silencing Position Effects", Human Gene Therapy 18:333-343 (2007).
Baum et al., "Concise Review: Managing Genotoxicity in the Therapeutic Modification of Stem Cells", Stem Cells 29:1479-1484 (2011).
Baum, "Gene Therapy for SCID-X1: Focus on Clinical Data", Molecular Therapy 19(12):2103-2104 (2011).
Cartier et al., "Hematopoietic Stem Cell Gene Therapy with a Lentiviral Vector in X-Linked Adrenoleukodystrophy", Science 326:818-823 (2009).
Cavazzana-Calvo et al., "Transfusion independence and HMGA2 activation after gene therapy of human β-thalassaemia", Nature 467(7313):318-322 (2010).
Deichmann et al., "Vector integration is nonrandom and clustered and influences the fate of lymphopoiesis in SCID-X1 gene therapy", J. Clin. Invest. 117(8):2225-2232 (2007).

(Continued)

*Primary Examiner* — Maria Marvich
(74) *Attorney, Agent, or Firm* — Nixon Peabody LLP; Mark J. FitzGerald

(57) ABSTRACT

Provided herein are methods for identifying high potency genomic insulator elements that can be used in a vector composition e.g., that are useful for preventing unwanted expression of neighboring genes, such as proto-oncogenes, when administered to a subject in need thereof. Also provided herein are methods for treating disease and methods for administering a nucleic acid to a subject using such vectors.

26 Claims, 31 Drawing Sheets

Specification includes a Sequence Listing.

(56) References Cited

OTHER PUBLICATIONS

Dunbar et al., "Gene therapy activates EVI1, destabilizes chromosomes", Nat. Met 16(2):163-165 (2010).
Galy et al., "Gene therapy for the Wiskott-Aldrich syndrome", Curr. Opin. Allergy Clin. Immunol. 11:545-550 (2011).
Grant et al., "FIMO: scanning for occurrences of a given motif", Bioinformatics 27(7):1017-1018 (2011).
Hacein-Bey-Abina et al., "Efficacy of Gene Therapy for X-Linked Severe Combined Immunodeficiency", N. Engl. J. Med. 363(4):355-364 (2010).
Hacein-Bey-Abina et al., "Insertional oncogenesis in 4 patients after retrovirus-mediated gene therapy of SCID-X1", J. Clin. Invest. 118(9):3132-3142 (2008).
Howe et al., "Insertional mutagenesis combined with acquired somatic mutations causes leukemogenesis following gene therapy of SCID-X1 patients", J. Clin. Invest. 118(9):3143-3150 (2008).
Jolma et al., "DNA-Binding Specificities of Human Transcription Factors", Cell 152:327-339 (2013).
Kharchenko et al., "Design and analysis of ChIP-seq experiments for DNA-binding proteins", Nat. Biotechnol. 26(12):1351-1359 (2008).
Kohn et al. "Gene Therapy Fulfilling Its Promise", N. Engl. J. Med. 360(5):518-521 (2009).
Li et al., "Extensive Promoter-centered Chromatin Interactions Provide a Topological Basis for Transcription Regulation", Cell 148(1-2):84-98 (2012).
Matys et al., "TRANSFAC and its module TRANSCompel: transcriptional gene regulation in eukaryotes", Nucleic Acids Research 34(Database issue):D108-D110 (2006).
Mukhopadhyay et al., "The Binding Sites for the Chromatin Insulator Protein CTCF Map to DNA Methylation-Free Domains Genome-Wide", Genome Research 14:1594-1602 (2004).
Nakahashi et al., "A Genome-wide Map of CTCF Multivalency Redefines the CTCF Code", Cell Reports 3:1678-1689 (2013).
Neph et al., "An expansive human regulatory lexicon encoded in transcription factor footprints", Nature 489(7414):83-90 (2012).
Neph et al., "BEDOPS: high-performance genomic feature operations", Bioinformatics 28(14):1919-1920 (2012).
Newburger et al., "UniPROBE: an online database of protein binding microarray data on protein-DNA interactions", Nucleic Acids Research 37(Database issue):D77-D82 (2009).
Ohlsson et al., "CTCF is a uniquely versatile transcription regulator linked to epigenetics and disease", TRENDS in Genetics 17(9):520-527 (2001).
Portales-Casamar et al., "JASPAR 2010: the greatly expanded open-access database of transcription factor binding profiles", Nucleic Acids Research 38(Database issue):D105-D110 (2010).
Schwarzwaelder et al., "Gammaretrovirus-mediated correction of SCID-X1 is associated with skewed vector integration site distribution in vivo", J. Clin. Invest. 117(8):2241-2249 (2007).
Seita et al., "Gene Expression Commons: An Open Platform for Absolute Gene Expression Profiling", PLoS One 7(7):e40321 (2012).
Song et al., "Open chromatin defined by DNaseI and FAIRE identifies regulatory elements that shape cell-type identity", Genome Research 21:1757-1767 (2011).
Stein et al., "Genomic instability and myelodysplasia with monosomy 7 consequent to EVI1 activation after gene therapy for chronic granulomatous disease", Nat Med. 16(2):198-204 (2010).
Thurman et al., "The accessible chromatin landscape of the human genome", Nature 489(7414):75-82 (2012).
Tubb et al., "Simultaneous sequence transfer into two independent locations of a reporter vector using MultiSite Gateway Technology", BioTechniques 39:553-557 (2005).
Arumugam et al., "Improved Human beta-globin Expression from Self-inactivating Lentiviral Vectors Carrying the Chicken Hypersensitive Site-4 (cHS4) Insulator Element", Mol. Ther. 15:1863-1871 (2007).

Bell et al., "The Protein CTCF Is Required for the Enhancer Blocking Activity of Vertebrate Insulators", Cell 98:387-396 (1999).
Burgess-Beusse et al., "The insulation of genes from external enhancers and silencing chromatin", Proc. Natl. Acad. Sci. U.S.A. 99(suppl. 4):16433-16437 (2002).
Chung et al., "Characterization of the chicken beta-globin insulator", Proc. Natl. Acad. Sci. U.S.A. 94:575-580 (1997).
Dickson et al., "VEZF1 Elements Mediate Protection from DNA Methylation", PLoS Genet 6(1):e1000804 (2010).
Dixon et al., "Topological Domains in Mammalian Genomes Identified by Analysis of Chromatin Interactions", Nature 485(7398):376-380(2012).
Emery et al., "A chromatin insulator protects retrovirus vectors from chromosomal position effects", Proc. Natl. Acad. Sci. U.S.A. 97(16):9150-9155 (2000).
Emery, "The Use of Chromatin Insulators to Improve the Expression and Safety of Integrating Gene Transfer Vectors", Hum. Gene Ther. 22:761-774 (2011).
Evans-Galea et al., "Suppression of Clonal Dominance in Cultured Human Lymphoid Cells by Addition of the cHS4 Insulator to a Lentiviral Vector", Mol. Ther. 15(4):801-809 (2007).
Gales et al., "Chromatin Boundaries, Insulators, and Long-Range Interactions in the Nucleus", Cold Spring Harb. Symp. Quant. Biol. 75:79-85 (2010).
Kim et al., "Analysis of the Vertebrate Insulator Protein CTCF-Binding Sites in the Human Genome", Cell 128:1231-1245 (2007).
Li et al., "Genomic and Functional Assays Demonstrate Reduced Gammaretroviral Vector Genotoxicity Associated With Use of the cHS4 Chromatin Insulator", Mol. Ther. 17(4):716-724 (2009).
Maurano et al., "Widespread Site-Dependent Buffering of Human Regulatory Polymorphism.", PLoS Genet., 8(3):e1002599 (2012).
Nienhuis et al., "Genotoxicity of Retroviral Integration in Hematopoietic Cells", Mol. Ther. 13(6):1031-1049 (2006).
Parelho et al., "Cohesins Functionally Associate with CTCF on Mammalian Chromosome Arms", Cell 132:422-433 (2008).
Phillips et al., "CTCF: Master Weaver of the Genome", Cell 137:1194-1211 (2009).
Renda et al., "Critical DNA Binding Interactions of the Insulator Protein CTCF: a small number of zinc fingers mediate strong binding, and a single finger-DNA interaction controls binding at imprinted loci", J. Biol. Chem. 282(46):33336-33345 (2007).
Ryu et al., "An experimental system for the evaluation of retroviral vector design to diminish the risk for proto-oncogene activation", Blood 111(4):1866-1875 (2008).
Schmidt et al., "Waves of Retrotransposon Expansion Remodel Genome Organization and CTCF Binding in Multiple Mammalian Lineages", Cell 148:335-348 (2012).
Uchida et al., "The Chicken Hypersensitivity Site 4 Core Insulator Blocks Promoter Interference in Lentiviral Vectors", Hum. Gene. Ther. Methods 24:117-124 (2013).
Wang et al., "Widespread plasticity in CTCF occupancy linked to DNA methylation", Genome Res. 22:1680-1688 (2012). (with Supplemental pp. 1-10).
Xi et al., Identification and Characterization of Cell Type-Specific and Ubiquitous Chromatin Regulatory Structures in the Human Genome, PLoS Genet. 3(8):e136 (2007).
Chung et al., "A 5' Element of the Chicken beta-Globin Domain Serves as an Insulator in Human Erythroid Cells and Protects against Position Effect in Drosophila", Cell 74(3), 505-514, 1993.
Gaszner et al., "Insulators: exploiting transcriptional and epigenetic mechanisms", Nat Rev Genet 7(9), 703-713, 2006.
Liu et al., "Genomic discovery of potent chromatin insulators for human gene therapy", Nat Biotechnol 33(2), 198-203, 2015.
Ryu et al., "A chromatin insulator blocks interactions between globin regulatory elements and cellular promoters in erythroid cells", Blood Cells Mol Dis 39(3), 221-228, 2007.
Wendt et al., "Cohesin mediates transcriptional insulation by CCCTC-binding factor", Nature 451(7180), 796-801, 2008.

* cited by examiner

| Vector | Estimated no. tumors[a] | Estimated no. provirus[b] | Tumors per $10^5$ provirus | Probability vs. no insert[c] | Probability vs. cHS4[c] |
|---|---|---|---|---|---|
| Mock | 0 | 0 | 0 | <<0.001 | <<0.001 |
| No insert | 23.0 | $0.49 \times 10^5$ | 46.9 | -- | <0.001 |
| Spacer | ≥30 | $0.67 \times 10^5$ | ≥44.7 | n.e. | <0.001 |
| cHS4 | 9.15 | $0.54 \times 10^5$ | 16.9 | <0.001 | -- |
| A1 | 2.23 | $0.64 \times 10^5$ | 3.9 | <0.001 | <0.05 |

(a) Based on the poisson distribution for the fraction of recipients with no tumors; (b) Based on the initial cell numbers and initial transduction rates; (c) Based on the Z-test for two proportions.

*FIG. 4C*

GENOMIC INSULATOR ELEMENTS AND USES THEREOF

CROSS-REFERENCE TO RELATED APPLICATIONS

This application is a 35 U.S.C. § 371 National Phase Entry Application of International Application No. PCT/US2015/020369 filed Mar. 13, 2015, which designates the U.S. and which claims benefit under 35 U.S.C. § 119(e) of U.S. Provisional Application Nos. 61/953,419 filed Mar. 14, 2014 and 62/068,226 filed Oct. 24, 2014, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 13, 2015, is named 034186-084340-PCT_SL2.txt and is 32,877 bytes in size.

GOVERNMENT SUPPORT

This invention was made with government support under Grant No. PO1 HL053750, awarded by the National Institutes of Health. The government has certain rights in the invention.

FIELD OF THE DISCLOSURE

The field of the disclosure relates to gene therapy vector compositions comprising a genomic insulator and uses thereof.

BACKGROUND

Hematopoietic stem cell gene therapy has already made an impact on the treatment of several inherited diseases. Patients with X-linked SCID (1), adenosine deaminase deficiency (2), X-linked adeno-leukodystrophy (3) and beta thalassemia (4) have been cured of their disease or their clinical status was dramatically improved. However, genotoxic side effects secondary to vector-mediated insertional mutagenesis appeared in a proportion of patients, including T-cell leukemia in almost 25% of patients treated in the X-linked SCID gene therapy trials (1). Genotoxicity arises from the activation of cellular oncogenes by the enhancers in the viral vectors (reviewed in 5,6). Various approaches have been attempted to decrease the risks of insertional mutagenesis.

SUMMARY

The compositions and methods described herein are based, in part, on the discovery of a method for identifying a high potency genomic insulator that can provide strong insulator activity when administering an exogenous nucleic acid sequence. Such strong insulator activity can, for example, prevent oncogene activation. Thus, provided herein are compositions comprising gene therapy vectors encoding at least one copy of a genomic insulator element and uses thereof. The compositions and methods described herein have the advantage of reducing tumor formation compared to gene therapy vectors lacking high potency genomic insulator element(s) as described herein. In addition, the high potency genomic insulator elements described herein are small in size, such that they can be easily incorporated into gene therapy vectors without significantly affecting viral titers.

One aspect provided herein relates to a viral vector composition encoding: at least one copy of a high potency genomic insulator element, wherein the genomic insulator element comprises a sequence less than 400 bp and a CTCF binding site core sequence. CTCF is the name given to the CCCTC-binding factor initially discovered as a negative transcriptional regulator of the chicken c-myc gene (Lobanenkov, W. et al., (1990) *Oncogene* 5; 1743-1752).

In one embodiment of this aspect and all other aspects described herein, the viral vector is a retroviral vector.

In another embodiment of this aspect and all other aspects described herein, the retroviral vector is a lentiviral vector.

In another embodiment of this aspect and all other aspects described herein, the viral vector is an adenoviral vector or adeno-associated viral vector.

In another embodiment of this aspect and all other aspects described herein, the viral vector is a gene therapy vector.

In another embodiment of this aspect and all other aspects described herein, the vector further comprises a sequence encoding a therapeutic agent.

In another embodiment of this aspect and all other aspects described herein, the core sequence is a 14 bp sequence selected from the group consisting of: CACCAGGTG-GCGCT (SEQ ID NO.: 1), CCACCAGGGGGAGC (SEQ ID NO.: 2), TCAGTAGAGGGCGC (SEQ ID NO.: 3), CCACTAGGGGGCAG (SEQ ID NO.: 4), CAGCA-GAGGGCGCT (SEQ ID NO.: 5), CAGTAGAGGGCGCT (SEQ ID NO.: 6), CCCTCTCCTGGGCA (SEQ ID NO.: 7), GCAGCAGAGAGCAA (SEQ ID NO.: 8), and CCCTCT-GCTGACTG (SEQ ID NO.: 9).

In another embodiment of this aspect and all other aspects described herein, the genomic insulator element comprises a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In another embodiment of this aspect and all other aspects described herein, the vector comprises at least two genomic insulator elements.

In another embodiment of this aspect and all other aspects described herein, the at least two genomic insulator elements are positioned in the vector such that they flank the vector provirus.

In another embodiment of this aspect and all other aspects described herein, the vector comprises two copies of the same genomic insulator element.

In another embodiment of this aspect and all other aspects described herein, the at least two genomic insulator elements are two different genomic insulator elements.

In another embodiment of this aspect and all other aspects described herein, the at least two genomic insulator elements are each a 14 bp sequence selected from the group consisting of:

CACCAGGTGGCGCT, (SEQ ID NO.: 1)

CCACCAGGGGAGC, (SEQ ID NO.: 2)

TCAGTAGAGGGCGC, (SEQ ID NO.: 3)

CCACTAGGGGCAG, (SEQ ID NO.: 4)

CAGCAGAGGGCGCT, (SEQ ID NO.: 5)

CAGTAGAGGGCGCT, (SEQ ID NO.: 6)

CCCTCTCCTGGGCA, (SEQ ID NO.: 7)

GCAGCAGAGAGCAA, (SEQ ID NO.: 8)
and

CCCTCTGCTGACTG. (SEQ ID NO.: 9)

In another embodiment of this aspect and all other aspects described herein, the at least two genomic insulator elements each comprise a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In another embodiment of this aspect and all other aspects described herein, the CTCF binding site core sequence is a high occupancy CTCF binding site in the human genome.

In another embodiment of this aspect and all other aspects described herein, the high occupancy site comprises at least 85%, at least 90%, at least 95%, at least 98%, at least 99% or 100% CTCF occupancy. In one embodiment, the high occupancy site is determined in a K562 myelogenous leukemia immortalized cell line.

In another embodiment of this aspect and all other aspects described herein, the gene insulator element does not significantly alter viral titers of the vector.

In another embodiment of this aspect and all other aspects described herein, the sequence of the genomic insulator element is less than 300 bp. In another embodiment of this aspect and all other aspects described herein, the sequence of the genomic insulator elements is less than 400 bp.

In another embodiment of this aspect and all other aspects described herein, the genomic insulator element does not substantially comprise silencer activity.

In another embodiment of this aspect and all other aspects described herein, the vector optionally comprises one or more of the following: (a) a promoter, (b) an enhancer, (c) a restriction site, (d) an untranslated region, (e) a DNaseI-hypersensitive site, (f) a multiple cloning site, (g) a long terminal repeat, or (h) a sequence encoding a poly A tail.

In another embodiment of this aspect and all other aspects described herein, the therapeutic agent comprises a gene of interest, a protein, a dominant negative mutant, an RNA interference agent, or an miRNA. In another embodiment, the therapeutic agent is a zinc finger nuclease, a TALEN, a CRISPR, or a meganuclease.

In another embodiment of this aspect and all other aspects described herein, the high potency genomic insulator exhibits an enhancer blocking activity greater than that of the cHS4 insulator element. In one embodiment, the high potency genomic insulator exhibits an enhancer blocking activity at least 50% greater than that of the cHS4 insulator element. In other embodiments, the high potency genomic insulator exhibits an enhancer blocking activity at least 75%, at least 80%, at least 90%, at least 1-fold, at least 2-fold, at least 5-fold, at least 10-fold, at least 15-fold, at least 20-fold, at least 50-fold, at least 100-fold (or more) greater than that of the cHS4 insulator element.

Also provided herein in another aspect is a method for identifying a high potency genomic insulator, the method comprising: (a) determining the occupancy of one or more CTCF binding motifs in a genome by CTCF protein, and (b) testing for enhancer blocking activity, thereby identifying a high potency genomic insulator.

In one embodiment of this aspect and all other aspects described herein, the method further comprises the following steps after step (a): (i) classifying the one or more CTCF binding motifs determined to have occupancy by CTCF into classes each having a unique CTCF core sequence, (ii) ranking the classes of CTCF binding motifs identified in step (i) by their CTCF occupancy from highest occupancy to lowest, and (iii) selecting one or more CTCF binding motifs within a highly ranked class.

In another embodiment of this aspect and all other aspects described herein, the step (a) of determining the occupancy of one or more CTCF binding motifs in a genome comprises the following steps: (i) determining the number of instances of one or more CTCF binding motifs in the genome by scanning a database comprising the substantially complete genomic sequence for the one or more CTCF binding motifs, (ii) identifying the one or more CTCF binding motifs in the genome that function to bind CTCF using a database comprising sequences that bind CTCF determined using ChIP-sequencing technology, (iii) aligning each instance of the one or more CTCF binding motifs of step (i) with the CTCF binding data of step (ii), and (iv) calculating the percentage of CTCF binding motifs instances that function to bind CTCF, thereby determining the occupancy.

In another embodiment of this aspect and all other aspects described herein, the core sequence is a 14 bp sequence selected from the group consisting of:

CACCAGGTGGCGCT, (SEQ ID NO.: 1)

CCACCAGGGGAGC, (SEQ ID NO.: 2)

TCAGTAGAGGGCGC, (SEQ ID NO.: 3)

CCACTAGGGGCAG, (SEQ ID NO.: 4)

CAGCAGAGGGCGCT, (SEQ ID NO.: 5)

CAGTAGAGGGCGCT, (SEQ ID NO.: 6)

-continued

CCCTCTCCTGGGCA,                    (SEQ ID NO.: 7)

GCAGCAGAGAGCAA,                    (SEQ ID NO.: 8)
and

CCCTCTGCTGACTG.                    (SEQ ID NO.: 9)

In another embodiment of this aspect and all other aspects described herein, the CTCF binding motif comprises a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In another embodiment of this aspect and all other aspects described herein, the occupancy of the CTCF binding motif selected for testing exhibits at least 85%, at least 90%, at least 95%, at least 98%, at least 99% or 100% CTCF occupancy in an established cell line or in primary cells. For the avoidance of doubt, CTCF occupancy can be determined relative to the occupancy determined in K562 cells.

In another embodiment of this aspect and all other aspects described herein, the sequence of the CTCF binding motif is less than 300 bp. In another embodiment of this aspect and all other aspects described herein, the sequence of the CTCF binding motif is less than 400 bp.

In another embodiment of this aspect and all other aspects described herein, the high potency genomic insulator exhibits an enhancer blocking activity greater than that of the cHS4 insulator element. In one embodiment, the high potency genomic insulator exhibits an enhancer blocking activity at least 50% greater than that of the cHS4 insulator element. In other embodiments, the high potency genomic insulator exhibits an enhancer blocking activity at least 75%, at least 80%, at least 90%, at least 1-fold, at least 2-fold, at least 5-fold, at least 10-fold, at least 15-fold, at least 20-fold, at least 50-fold, at least 100-fold (or more) greater than that of the cHS4 insulator element.

Also provided herein in another aspect is a method for treating a disease, the method comprising administering a vector as described herein, wherein the vector further comprises a sequence encoding a therapeutic agent, and wherein the therapeutic agent mediates treatment of the disease.

In one embodiment of this aspect and all other aspects described herein, the therapeutic agent comprises a protein, a dominant negative mutant, an RNA interference agent, or an miRNA.

In another embodiment of this aspect and all other aspects described herein, the high potency genomic insulator exhibits an enhancer blocking activity greater than that of the cHS4 insulator element. In one embodiment, the high potency genomic insulator exhibits an enhancer blocking activity at least 50% greater than that of the cHS4 insulator element. In other embodiments, the high potency genomic insulator exhibits an enhancer blocking activity at least 75%, at least 80%, at least 90%, at least 1-fold, at least 2-fold, at least 5-fold, at least 10-fold, at least 15-fold, at least 20-fold, at least 50-fold, at least 100-fold (or more) greater than that of the cHS4 insulator element.

Another aspect provided herein relates to a method for administering a nucleic acid encoding a therapeutic agent, the method comprising administering to a subject a viral vector encoding: (a) a therapeutic agent, and (b) at least one copy of a high potency genomic insulator element, wherein the genomic insulator element comprises a sequence less than 400 bp and a CTCF binding site core sequence.

In one embodiment of this aspect and all other aspects described herein, the gene therapy vector reduces tumor formation in the subject by at least 50% compared to a gene therapy vector lacking the high potency genomic insulator element.

In another embodiment, the vector produces an at least 10-fold reduction in rate of tumor production compared to the same vector lacking the high potency genomic insulator element. In other embodiments, the vector produces an at least 15-fold, at least 20-fold, at least 25-fold, at least 30-fold, at least 40-fold, at least 50-fold, at least 100-fold or more reduction in rate of tumor production compared to the same vector lacking the high potency genomic insulator element.

In another embodiment of this aspect and all other aspects described herein, the viral vector is a retroviral vector.

In another embodiment of this aspect and all other aspects described herein, the retroviral vector is a lentiviral vector.

In another embodiment of this aspect and all other aspects described herein, the viral vector is an adenoviral vector or adeno-associated viral vector.

In another embodiment of this aspect and all other aspects described herein, the core sequence is a 14 bp sequence selected from the group consisting of:

CACCAGGTGGCGCT,                    (SEQ ID NO.: 1)

CCACCAGGGGGAGC,                    (SEQ ID NO.: 2)

TCAGTAGAGGGCGC,                    (SEQ ID NO.: 3)

CCACTAGGGGCAG,                     (SEQ ID NO.: 4)

CAGCAGAGGGCGCT,                    (SEQ ID NO.: 5)

CAGTAGAGGGCGCT,                    (SEQ ID NO.: 6)

CCCTCTCCTGGGCA,                    (SEQ ID NO.: 7)

GCAGCAGAGAGCAA,                    (SEQ ID NO.: 8)
and

CCCTCTGCTGACTG.                    (SEQ ID NO.: 9)

In another embodiment of this aspect and all other aspects described herein, the genomic insulator element comprises a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In another embodiment of this aspect and all other aspects described herein, the vector comprises at least two genomic insulator elements.

In another embodiment of this aspect and all other aspects described herein, the at least two genomic insulator elements are positioned in the vector such that they flank the vector provirus.

In another embodiment of this aspect and all other aspects described herein, the vector comprises at least two copies of the same genomic insulator element.

In another embodiment of this aspect and all other aspects described herein, the at least two genomic insulator elements are at least two different genomic insulator elements.

In another embodiment of this aspect and all other aspects described herein, the at least two genomic insulator elements are each a 14 bp sequence selected from the group consisting of:

CACCAGGTGGCGCT, (SEQ ID NO.: 1)

CCACCAGGGGGAGC, (SEQ ID NO.: 2)

TCAGTAGAGGGCGC, (SEQ ID NO.: 3)

CCACTAGGGGGCAG, (SEQ ID NO.: 4)

CAGCAGAGGGCGCT, (SEQ ID NO.: 5)

CAGTAGAGGGCGCT, (SEQ ID NO.: 6)

CCCTCTCCTGGGCA, (SEQ ID NO.: 7)

GCAGCAGAGAGCAA, (SEQ ID NO.: 8)
and

CCCTCTGCTGACTG. (SEQ ID NO.: 9)

In another embodiment of this aspect and all other aspects described herein, the at least two genomic insulator elements each comprise a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In another embodiment of this aspect and all other aspects described herein, the CTCF binding site core sequence is a high occupancy CTCF binding site in the human genome.

In another embodiment of this aspect and all other aspects described herein, the high occupancy site comprises a least 95%, at least 98%, at least 99% or 100% CTCF occupancy.

In another embodiment of this aspect and all other aspects described herein, the gene insulator element does not significantly alter viral titers of the vector.

In another embodiment of this aspect and all other aspects described herein, the sequence of the genomic insulator element is less than 300 bp. In another embodiment of this aspect and all other aspects described herein, the sequence of the genomic insulator elements is less than 400 bp.

In another embodiment of this aspect and all other aspects described herein, the genomic insulator element does not comprise silencer activity.

In another embodiment of this aspect and all other aspects described herein, wherein the vector optionally comprises one or more of the following: (a) a promoter, (b) an enhancer, (c) a restriction site, (d) an untranslated region, (e) a DNaseI-hypersensitivity site, (f) a multiple cloning site, and (g) a sequence encoding a poly A tail.

In another embodiment of this aspect and all other aspects described herein, the therapeutic agent comprises a gene of interest, a protein, a dominant negative mutant, an RNA interference agent, or an miRNA.

In another embodiment of this aspect and all other aspects described herein, the high potency genomic insulator exhibits an enhancer blocking activity greater than that of the cHS4 insulator element. In one embodiment, the high potency genomic insulator exhibits an enhancer blocking activity at least 50% greater than that of the cHS4 insulator element. In other embodiments, the high potency genomic insulator exhibits an enhancer blocking activity at least 75%, at least 80%, at least 90%, at least 1-fold, at least 2-fold, at least 5-fold, at least 10-fold, at least 15-fold, at least 20-fold, at least 50-fold, at least 100-fold (or more) greater than that of the cHS4 insulator element.

BRIEF DESCRIPTION OF THE FIGURES

(FIG. 2A) Assay design. The reporter plasmid pJCS-4/P4-P2K contains an expression cassette for GFP transcribed from the Aγ-globin gene promoter (γpro), and erythroid specific HS2 enhancer (HS2). Candidate fragments were inserted at two locations: upstream of the Aγ-globin-globin gene promoter, and between the nco gene (Nco) and the HS2 enhancer. In this configuration, the 3' insertion site allows the candidate insulator to physically block the communication between the HS2 enhancer and Aγ-globin-globin gene promoter. (FIG. 2B) Frequency of G418-resistant colonies as a percent of the neutral control. Histograms represent the mean±standard deviation from 4 independent experiments, and are reported as a percentage of the mean colony formation obtained with the spacer control (set at 100%). (FIG. 2C) Degree of insulation expressed as fold changed compared to the cHS4 control. The fold changes were calculated using the mean of colony numbers listed in Table 2. (FIG. 2D) Insulator activity as a function of the insulator class. Data are the same as in panel (FIG. 2B), but arranged according to insulator classes.

(FIG. 3A) Silencer assay design. The reporter plasmid is similar to that used for the enhancer-blocking assay (FIG. 3A), except that the 3' insertion site was located distal to the HS2 enhancer, allowing for uninterrupted communication between the HS2 enhancer and the Aγ-globin gene promoter. (FIG. 3B) Frequency of G418-resistant colonies as a percent of the neutral control. Histograms represent the mean±standard deviation from 3 or more independent experiments, and are reported as a percentage of the mean colony formation obtained with the spacer control (set at 100%). The 321 bp element used as a silencer (called T39) was identified in related studies, and maps to chrX: 11551258-11551578 (hg19). p vs control >0.05 for cHS4 and all insulator candidates (Bonferroni-corrected), p=3× $10^{-11}$ versus control for the silencer T39. (FIG. 3C) Lentiviral vector titer assay design. The third-generation lentiviral reporter vector expresses GFP from an internal Pgk gene promoter, and was flanked with the insulator candidates by insertion in the "double-copy" position of the 3' LTR. (FIG. 3D) Fraction of GFP-positive cells following transduction of HT1080 cells with titrating amounts of vector supernatant as a percentage of the no-insert control. Histograms represent the mean±standard deviation from 3 independent experiments, and are reported as a percentage of the fraction of GFP-positive cells obtained with the no-insert control (set at 100%). The insulators tested correspond to the elements of FIG. 2 except for C4 which was cloned only into the lentiviral vector.

FIGS. 4A-4C Genotoxicity assay. (FIG. 4A) Assay design for assessing the ability of insulators to reduce the rate of vector mediated genotoxicity. Insulator A1 was inserted into the proximal end of the 3' LTR of a gammaretroviral vector. During generation of vector provirus, this insert is copied to the 5' LTR, effectively flanking the internal expression cassettes. Supernatant from ecotropic vector producer lines matched for titer was used to transduce the IL-3 dependent cell line 32D. Independent sub-pools were subsequently expanded and transplanted into congenic mice (one independent sub-pool per mouse). Recipients were subsequently monitored for tumor formation (typically manifesting as splenomegaly) (24). (FIG. 4B) Kaplan-Myer tumor-free survival curves for mice transplanted with 32D cells that were mock-transduced or transduced with a vector containing insulator A1, or the 1.2 kb cHS4, or a 790 bp fragment from a portion of the cDNA for the mouse G6PD gene (as a neutral control), or no insert. (FIG. 4C) The underlying rate of transformation (tumors per $10^5$ provirus) was calculated by first estimating the number of transformation events based on the fraction of tumor-free animals at 28 weeks and the Poisson distribution, and then dividing these by the estimated number of cells that were transduced in the original cultures as described (24). P values were based on z-test for two proportions.

(FIG. 5A) The number of CTCF sites for each CTCF occupancy class that are bound or not bound by CTCF are shown for each of the top 1000 CTCF occupancy classes. CTCF occupancy classes sharing identical 14 bp core sequences were selected to have >50 sites. (FIG. 5B) Similar analysis showing the relative proportion of CTCF sites for each CTCF occupancy class that are bound by CTCF. Data from both panels are based on ChIP-seq studies in K562 cells.

(FIG. 12A) Cohesin is more frequently found at higher-occupancy CTCF classes. The proportion of members in each CTCF occupancy class overlapping cohesin (Rad21) binding by ChIP-seq in K562 cells was assessed (one data point for each of 1000 classes). Only instances with CTCF ChIP-seq occupancy were included. The trend line represents the LOESS fit. The locations of the high-occupancy classes A-F are indicated by arrows. R, Pearson correlation. (FIGS. 12B-12C) CTCF sites that overlap cohesin (+) have higher levels of CTCF occupancy (FIG. 12B) by ChIP-seq in K562 cells (16) and more accessible chromatin (FIG. 12C) by DNaseI-seq (47) than sites that don't (−). Legend for box plots: open box ends, first and third quartiles; whiskers, 1.5 times the interquartile range; filled circle, population median; open circles, individual outlier data points.

(FIG. 13A) Schematic showing the consensus sequences for the CTCF core and the extended recognition sequences (SEQ ID NOS: 108-110, respectively, in order of appearance). The spacing between the extended upstream motif and the core motif can vary (+0 or +1 bp), resulting in three modes of potential binding (Nakahashi et al. 2013). (FIG. 13B) Relationship between CTCF occupancy class and CTCF binding mode. The best matching of the three binding modes was determined for each CTCF binding site (by FIMO P-value), and then these data were used to determine the proportion of instances for each CTCF occupancy class that included overlapping the extended upstream motif (one data point for each of 1000 classes). Trend lines are shown for the proportion of instances involved overlapping the extended upstream motif with +0 spacing, +1 spacing, or either spacing as determined by LOESS fit. Note the inverse correlation between binding modes involving the upstream motifs and the CTCF occupancy class rank. R, Pearson correlation.

(FIG. 14A) Average number of RNA Polymerase II-mediated interactions spanning CTCF class instances in K562 cells; sum of two replicates (31). (FIG. 14B) Average number of CTCF-mediated interactions within 25 kb of class instances in K562 cells (31). (FIG. 14C) Proportion of instances in each class within 50 kb of IMR90 topologically associated domains (TADs) (25). In each panel, the high-affinity motif classes from which candidate insulators were chosen for testing. High occupancy classes A-F are highlighted. Trend lines represent LOESS fits. Interactions based on ChIA-PET for (FIG. 14A) and (FIG. 14B) were downloaded from the UCSC Genome Browser; only intrachromosomal interactions were considered (31). R indicates Spearman's correlation over top 400 CTCF occupancy classes.

DETAILED DESCRIPTION

Figure 1:
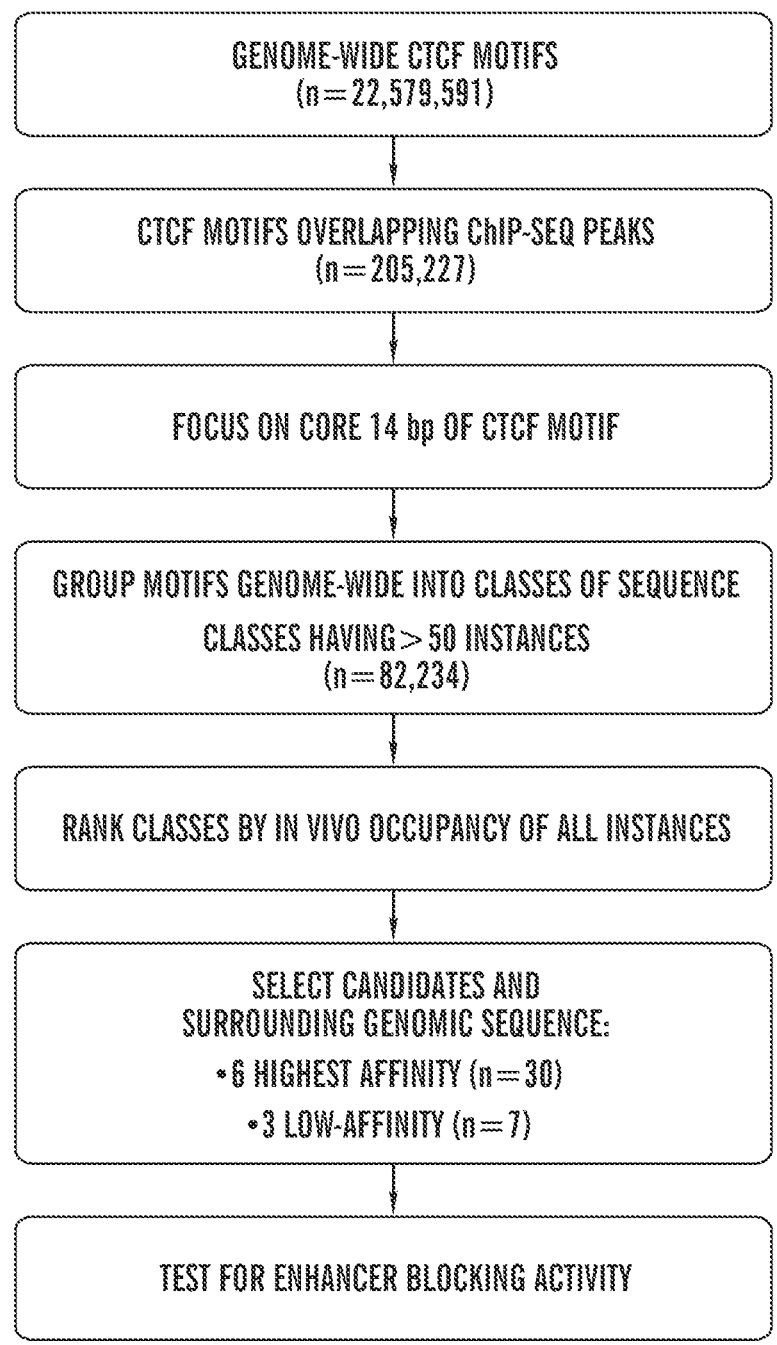
FIG. 1 Identification of putative insulators by genomic profiling. CTCF sites are marked by the presence of a sequence motif (Top right) and by ChIP-seq occupancy (shown in human K562 erythroleukemia cells). Sites were grouped into classes based on sharing identical 14 bp core sequences. Classes were then ranked according to genome-wide occupancy per class. Candidate sites for each class were tested for enhancer-blocker activity as described in the text (SEQ ID NOs: 108-110, respectively, in order of appearance).
Figure 1:
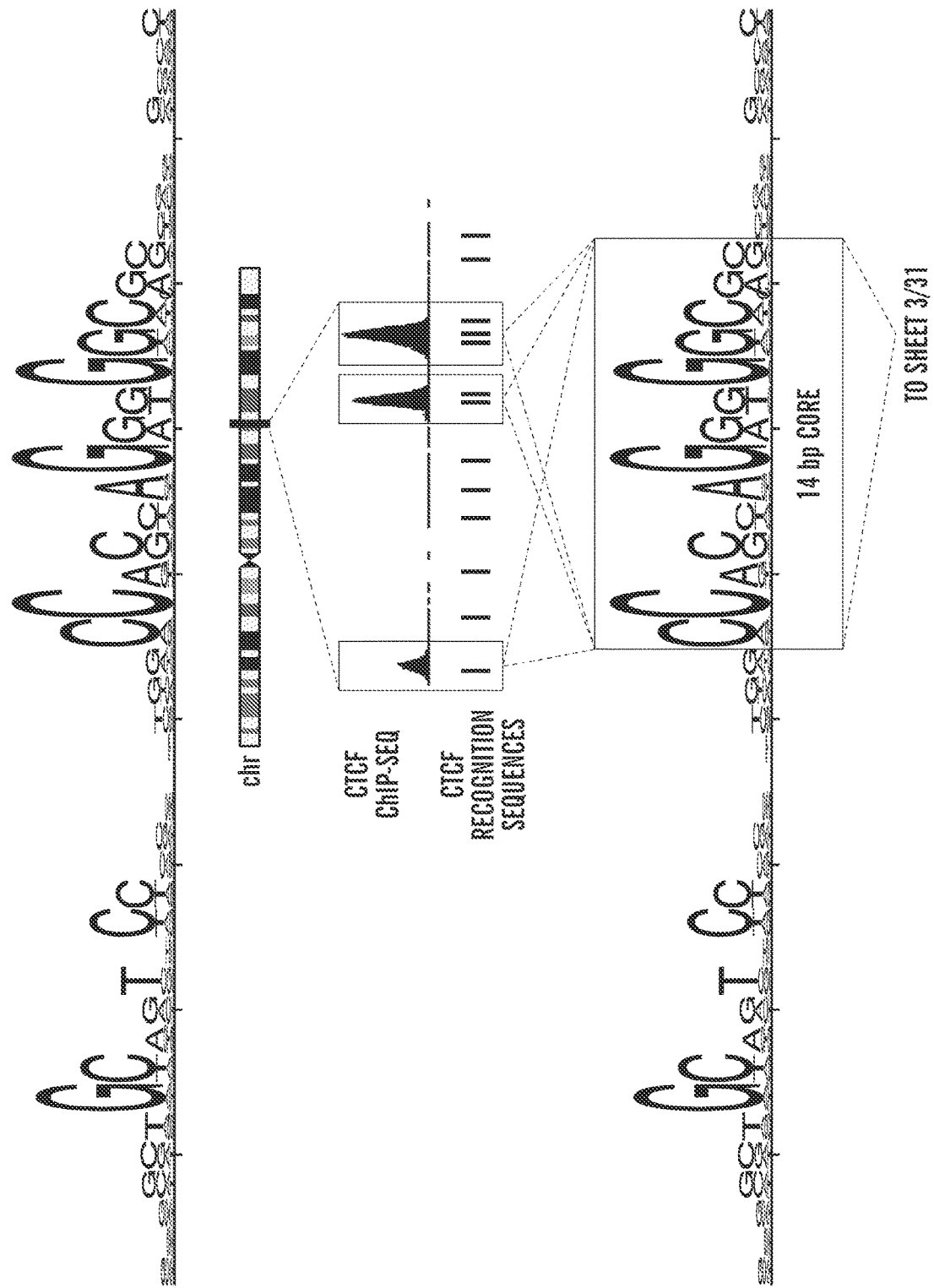
Figure 1:
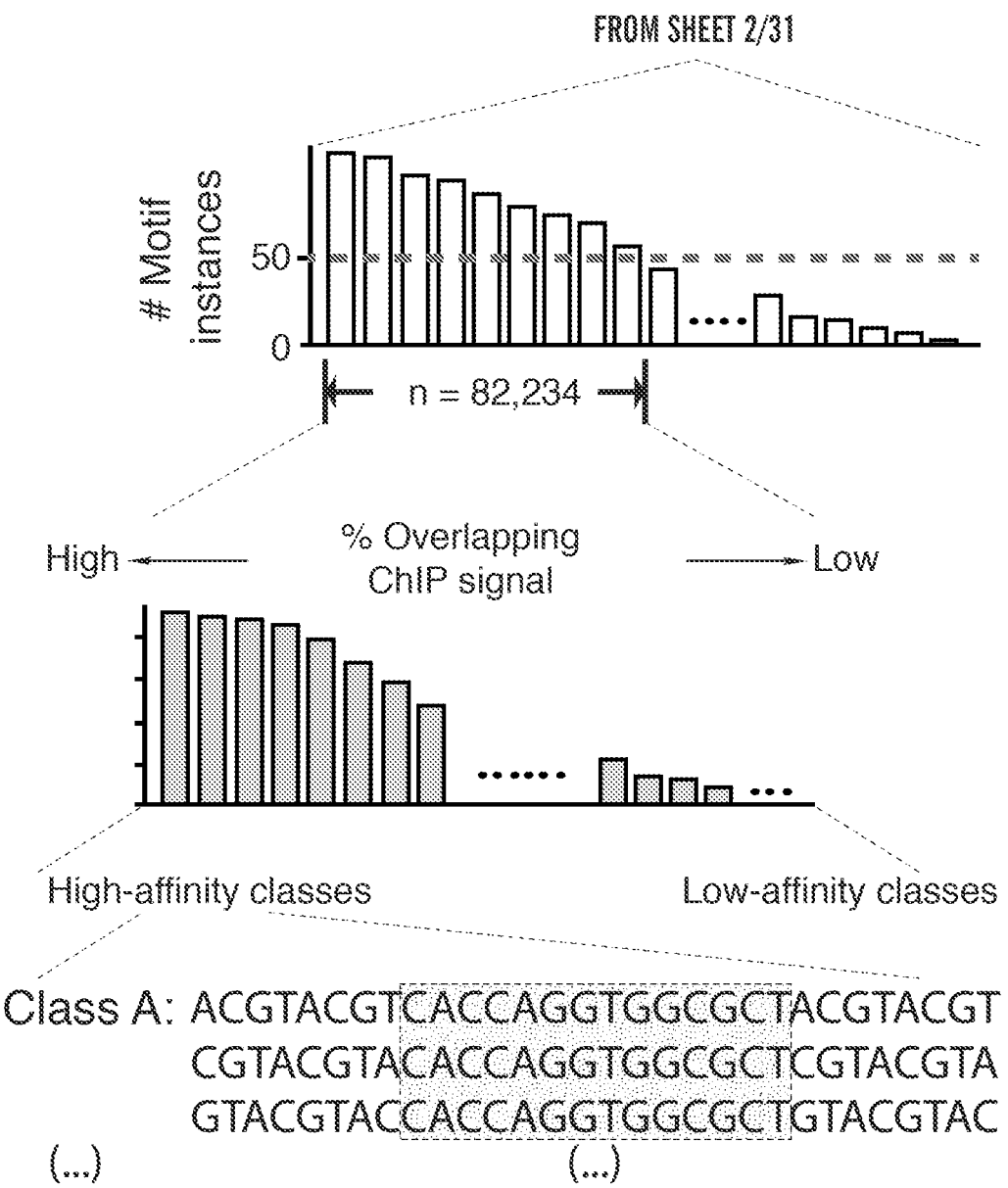

Provided herein are methods for identifying high potency genomic insulator elements that can be used in a vector composition e.g., that are useful for preventing unwanted expression of neighboring genes, such as proto-oncogenes, when administered to a subject in need thereof. Also provided herein are vectors comprising such elements, methods for treating disease and methods for administering a nucleic acid to a subject using such vectors.

Definitions

The term "vector," refers to a nucleic acid vehicle that contains a combination of recombinant DNA sequence components for directing transgene expression. In one embodiment, the vector is a viral vector including, but not limited to, retroviral vectors (e.g., lentiviral vectors), adenoviral vectors, or adeno-associated viral vectors. In another embodiment, the vector is a gene therapy vector.

As used herein, the term "retrovirus" refers an RNA virus that reverse transcribes its genomic RNA into a linear double-stranded DNA copy and subsequently covalently integrates its genomic DNA into a host genome. Retroviruses belong to the family Retroviridae, which is composed of numerous non-icosahedral, enveloped viruses which possess two copies of a single-stranded RNA genome that has a short dimerized region. Retroviruses are a common tool for gene delivery (Miller, 2000, Nature. 357: 455-460). Once the virus is integrated into the host genome, it is referred to as a "provirus." The provirus serves as a template for RNA polymerase II and directs the expression of RNA molecules which encode the structural proteins and enzymes needed to produce new viral particles. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. The term "retrovirus" or "retroviral vector", as used herein is meant to include "lentivirus" and "lentiviral vectors" respectively.

As used herein, the term "lentivirus" refers to a group (or genus) of complex retroviruses. Illustrative retroviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

As used herein the term "genomic insulator element" refers to a nucleic acid sequence that prevents the read-through expression of a gene (e.g., a neighboring gene). Such genomic insulator elements can comprise a barrier function to protect chromosomal domains from heterchromatinization and/or an enhancer-blocking function to prevent the interaction between regulatory elements of different chromatin domains. The genomic insulator element can include, for example, a CTCF core sequence or a CTCF binding motif that includes a CTCF core sequence. In one embodiment, the genomic insulator element comprises a CTCF binding motif. In another embodiment, the genomic insulator element comprises, at a minimum, a CTCF binding site core sequence.

As used herein the term "high potency genomic insulator element" refers to a genomic insulator element that prevents read-through expression of a neighboring gene or genomic sequence from a vector promoter by at least 50% compared to an identical vector lacking the genomic insulator element (as determined using an enhancer blocking assay as described herein in the working Examples). In some embodiments, the high potency genomic insulator element prevents read-through expression by at least 75%, at least 80%, at least 85%, at least 90%, at least 95%, at least 98%, at least 99%, or even 100% (i.e., no read-through expression detected) compared to the identical vector lacking the genomic insulator element.

The terms "CTCF binding site core sequence" or "core sequence" are used interchangeably herein and refer, at a minimum, to a 14 bp nucleic acid sequence comprising a GC-rich region that is sufficient to engage at least one of zinc fingers 4-8 of CTCF. CTCF binding motifs in a genome can be classified into sub-groups or "classes" of genomic insulator elements based on this 14 bp core sequence. That is, CTCF binding motifs can be classified based on the unique 14 bp core sequence to which CTCF binds.

As used herein, the term "high occupancy CTCF binding site" refers to a nucleic acid sequence comprising a CTCF binding site core sequence that is occupied by CTCF at a frequency of at least 85% over the total number of instances of the core sequence in a given genome (e.g., a human genome, a K562 cell genome etc.). That is, at least 85% of the time that the given CTCF core sequence appears in a given genome, it is bound by CTCF as determined using e.g., ChIP-sequencing data. In other embodiments, the high occupancy CTCF binding site is at 90% occupied, at least 95% occupied, at least 96% occupied, at least 97% occupied, at least 98% occupied, at least 99% occupied, or even 100% occupied (i.e., CTCF binds to every instance in the genome where the core sequence is detected). In some embodiments, the term "high affinity CTCF binding site" is used interchangeably with the term "high occupancy CTCF binding site." In contrast, a "low affinity CTCF binding site" or "low occupancy CTCF binding site" refers to a site that is occupied at a frequency of less than 10% of the time. An "intermediate affinity CTCF binding site" or "intermediate occupancy CTCF site" refers to a site that is occupied at a frequency of between 10% and 85% of the time, for example, 15-85%, 25-85%, 50-85%, 75-85%, 15-75%, 15-50%, 15-25%, 25-75%, 25-50%, 50-75%, or any range therebetween.

As used herein, the phrase "does not significantly alter viral titers of the vector" indicates that a vector comprising at least one genomic insulator element has, in one embodiment, substantially the same viral titer as the identical vector lacking the at least one genomic insulator element, for example, in a lentiviral vector titer assay as described herein. In other embodiments, the viral titer of the vector comprising a genomic insulator element is modulated (i.e., increased titer or decreased titer) by less than 20%, less than 15%, less than 10%, less than 5%, less than 2%, or less than 1% as compared to an identical vector lacking the genomic insulator element.

As used herein, the term "silencer activity" refers to the ability of a nucleic acid sequence to bind a repressor to prevent protein expression from a gene. In one embodiment, silencer activity can be assessed by cloning the candidate insulator into a neo reporter construct such that the insertion brackets, rather than blocks, the enhancer and promoter. The constructs are then analyzed for the rate of colony formation under G418 selection in K652 cells.

As used herein, the term "does not substantially comprise silencer activity" indicates that the genomic insulator element comprises substantially the same silencer activity as a negative control insert.

As used herein, the term "therapeutic agent" refers to a molecule or composition that when administered can mediate treatment of a disease or disorder. The molecule or composition can be a protein, a nucleic acid sequence encoding a protein or a nucleic acid that comprises activity itself (e.g., miRNA). The therapeutic agent can be used to augment or replace functionality of a protein associated with a disease (i.e., due to misfolding, truncation, impaired activity, increased protein degradation, and the like). Alternatively the therapeutic agent can be used to inhibit, reduce or depress function of an in vivo target. Thus, a therapeutic agent can be an antibody, an antibody fragment, a protein, a dominant negative mutant, an RNA interference agent (e.g., an siRNA, an shRNA), or an miRNA, among others, each of which can be expressed from the viral vector(s) described herein. One of ordinary skill in the art can envision many therapeutic agents for use in the treatment of a disease or disorder.

As used herein, the term "highly ranked class" refers to a set of CTCF binding motifs classified by a unique 14 bp core sequence, which is among the top 20% (e.g., the top 15%, the top 10%, the top 5%, the top 2%, the top 1%) of the classes when they are ranked from highest occupancy to lowest. Alternatively the term "highly ranked class" can refer to the top 5, 4, 3, 2, or 1 classes of CTCF binding motifs when they are ranked from highest occupancy to lowest.

The term "operably linked" refers to the joining of distinct DNA molecules, or DNA sequences, to produce a functional transcriptional unit.

The terms "gene," "gene of interest," "transgene," and "nucleic acid sequence encoding a therapeutic agent" are used interchangeably herein. Generally, the terms refer to a nucleic acid sequence (e.g., DNA), that contains a coding sequence for a particular polypeptide, for example, a recombinant protein of interest such as a therapeutic antibody or a replacement enzyme. A transgene can also contain heterologous sequences to encode a fusion protein. The terms "gene," "gene of interest," "transgene," and "therapeutic agent" are not intended to include polyadenylation sites, promoters, enhancers, and insulators.

The term "promoter" refers to a nucleic acid sequence, that is typically positioned upstream of a gene and that recruits transcriptional machinery, such as the RNA polymerase and associated factors, that, in turn, initiates transcription of the gene.

The term "enhancer" refers to a nucleic acid sequence that can recruit transcriptional regulatory proteins, such as transcriptional activators, to enhance the transcriptional activation of a gene in an essentially position and orientation independent manner Thus, unlike a promoter, an enhancer can be located upstream, downstream, or even within an intron of a transcription unit. Enhancer elements from heterologous sources can be used as a component within expression vectors that represent embodiments of the compositions and methods described herein.

The term "flanking" refers to a relative position of one nucleic acid sequence with respect to another nucleic acid sequence. A flanking sequence precedes or follows a flanked sequence but need not be contiguous with, or immediately adjacent to the flanked sequence. For example, in the context of a transcription unit comprising a genomic insulator element and a transgene, the genomic insulator element can be placed at either (or both) ends of the nucleic acid encoding the therapeutic agent.

The terms "homology," "identity," and "similarity" refer to the degree of sequence similarity between two polypeptides or between two nucleic acid molecules being compared by sequence alignment. The degree of homology between two discrete nucleic acid sequences being compared is a function of the number of identical, or matching, nucleotides at comparable positions. The degree of homology between two discrete amino acid sequences being compared is a function of the number of identical, or matching, amino acids at comparable positions.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA," is defined as an RNA agent which functions to inhibit expression of a target gene, e.g., by RNAi. An siRNA can be chemically synthesized, can be produced by in vitro transcription, or can be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and can contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

The term "pharmaceutically acceptable" refers to compounds and compositions which can be administered to mammals without undue toxicity.

As used herein, the term "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by conventional methods (see, for example, Remington's Pharmaceutical Sciences, 18th edition, A. Gennaro, ed., Mack Publishing Co., Easton, Pa., 1990). The term "pharmaceutically acceptable carriers" excludes tissue culture medium.

As used herein, "a" or "an" means at least one, unless clearly indicated otherwise. As used herein, to "prevent" or "protect against" a condition or disease means to hinder, reduce or delay the onset or progression of the condition or disease.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "statistically significant" or "significantly" refers to statistical significance and generally means two standard deviations (2SD) or more above or below normal or a reference. The term refers to statistical evidence that there is a difference. It is defined as the probability of making a decision to reject the null hypothesis when the null hypothesis is actually true. The decision is often made using the p-value.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), and Current Protocols in Protein Science (CPPS), John E. Coligan (ed.), John Wiley and Sons, Inc., 2005 (ISBN 0471142735), the contents of which are all incorporated by reference herein in their entireties.

Genomic Insulator Element

Chromatin insulators can decrease the risk of insertional mutagenesis by disrupting the interactions between the enhancers in the vectors and the regulatory elements of cellular oncogenes (6,7). There are two kinds of chromatin insulators: barrier insulators, which protect chromosomal domains from heterochromatinization, and enhancer-blocking insulators, which prevent the interaction between regulatory elements of different chromatin domains (8). Certain elements combine barrier- and enhancer-blocking activities. The most extensively studied chromatin insulator is located in DNase I hypersensitive site 4 of the Locus Control Region of the chicken beta globin locus (cHS4) (9,10). Extensive studies have demonstrated that the enhancer-blocking activity of cHS4 insulator depends on binding of the transcriptional factor CTCF (11-14). Occupancy by CTCF genome-wide has been surveyed across a large number of cell types (15,16) and its binding sites are surprisingly conserved across species (17). A large fraction of CTCF binding sites genome-wide overlap with cohesin proteins, and insulator function at cHS4 is reportedly dependent upon cohesin (18). Furthermore, CTCF sites are enriched at topological domain boundaries (19).

Several studies have addressed the role of chromatin insulators in gene therapy, mostly by incorporating cHS4 or its components in viral vectors. cHS4 decreases the probability of vector silencing by its barrier function (20,21), the probability of activation of proximal regulatory elements by its enhancer-blocking function (22-24), and the risk of genotoxicity in ex vivo and in vivo assays (24-26). However, the cHS4 insulator has two noteworthy disadvantages: the fully active cHS4 element is very large (1.2 kb) and consumes precious space in viral vectors; and the incorporation of the full-length cHS4 often results in diminished vector titers.

The genomic insulator elements provided herein comprise enhancer-blocking to reduce the probability of activation of proximal regulatory elements. However the genomic insulator elements described herein are shorter than the active cHS4 element and can be easily incorporated into viral vectors without substantial loss of viral titers.

In one embodiment, the genomic insulator elements described herein are less than 600 bp in length. In other embodiments, the genomic insulator elements are less than 550 bp, less than 500 bp, less than 450 bp, less than 400 bp, less than 350 bp, less than 325 bp, less than 300 bp, less than 290 bp, less than 280 bp, less than 270 bp, less than 260 bp, less than 250 bp, less than 240 bp, less than 230 bp, less than 220 bp, less than 210 bp, less than 200 bp, less than 190 bp, less than 180 bp, less than 170 bp, less than 160 bp, less than 150 bp, less than 125 bp, less than 100 bp, less than 50 bp, less than 25 bp, less than 15 bp, or smaller. In one embodiment, the genomic insulator element is 14 bp in length.

In other embodiments, the genomic insulator elements described herein are between 100-600 bp in length, between 100-500 bp, between 100-400 bp, between 100-300 bp, between 100-250 bp, between 100-200 bp, between 100-175 bp, between 100-150 bp, between 150-600 bp, between 200-600 bp, between 300-600 bp, between 400-600 bp, between 500-600 bp, between 125-300 bp, between 150-300 bp, between 175-300 bp, between 200-300 bp, between 225-300 bp, between 250-300 bp, between 275-300 bp, and any range therebetween. In certain embodiments, the genomic insulator elements described herein are between 150-250 nucleotides in length. In certain embodiments, the genomic insulator elements described herein are between 119-284 nucleotides in length.

In one embodiment, a genomic insulator element provided herein comprises a 14 bp core sequence selected from the group consisting of:

```
                            (SEQ ID NO.: 1)
CACCAGGTGGCGCT, (SEQ ID NO.: 2)
CCACCAGGGGGAGC, (SEQ ID NO.: 3)
TCAGTAGAGGGCGC, (SEQ ID NO.: 4)
CCACTAGGGGGCAG, (SEQ ID NO.: 5)
CAGCAGAGGGCGCT, (SEQ ID NO.: 6)
CAGTAGAGGGCGCT, (SEQ ID NO.: 7)
CCCTCTCCTGGGCA, (SEQ ID NO.: 8)
GCAGCAGAGAGCAA,
and (SEQ ID NO.: 9)
CCCTCTGCTGACTG.
```

In another embodiment, a genomic insulator element as provided herein comprises a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36 (see e.g., Table 7).

Also contemplated herein are variants or homologues of the genomic insulator elements listed in Table 7, provided that the variants or homologues retain at least 75%, at least 80%, at least 85%, at least 90%, at least 95%, at least 98%, at least 99% or even 100% of the enhancer-blocking activity of the genomic insulator elements (determined, for example, using an enhancer-blocking assay as described in the working Examples). In some embodiments, it is also contemplated that a variant or homologue of a genomic insulator element listed in Table 7 will have greater enhancer-blocking activity than the sequences provided in Table 7. For example, a variant and/or homologue can have an activity at least 20% higher than the activity of a genomic insulator element sequence listed in Table 7. In other embodiments, the variant and/or homologue can have an activity at least 50% higher, at least 60% higher, at least 70% higher, at least 80% higher, at least 85% higher, at least 90% higher, at least 95% higher, at least 98% higher, at least 99% higher, at least 1-fold higher, at least 2-fold higher, at least 5-fold higher, at least 10-fold higher, at least 20-fold higher, at least 50-fold higher, at least 75-fold higher, at least 100-fold higher, at least 150-fold higher, at least 200-fold higher, at least 500-fold higher, at least 1000-fold higher activity, or more compared to the activity of a genomic insulator element listed in Table 7.

In one embodiment, a variant of a genomic insulator element comprises a sequence at least 80% identical to a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36. In other embodiments, the sequence of a genomic insulator element as described herein comprises a sequence at least 85%, at least 90%, at least 95%, at least 96%, at least 97%, at least 98%, or at least 99% identical to a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

In some embodiments, the genomic insulator element(s) described herein retain 100% identity within the 14 bp core sequence but the sequences outside of the core sequence (e.g., on either side of the core sequence) can comprise a sequence at least at least 85%, at least 90%, at least 95%, at least 96%, at least 97%, at least 98%, or at least 99% identical to the regions outside of the 14 bp core sequence in a sequence selected from the group consisting of: SEQ ID NO.: 10, SEQ ID NO.: 11, SEQ ID NO.: 12, SEQ ID NO.: 13, SEQ ID NO.: 14, SEQ ID NO.: 15, SEQ ID NO.: 16, SEQ ID NO.: 17, SEQ ID NO.: 18, SEQ ID NO.: 19, SEQ ID NO.: 20, SEQ ID NO.: 21, SEQ ID NO.: 22, SEQ ID NO.: 23, SEQ ID NO.: 24, SEQ ID NO.: 25, SEQ ID NO.: 26, SEQ ID NO.: 27, SEQ ID NO.: 28, SEQ ID NO.: 29, SEQ ID NO.: 30, SEQ ID NO.: 31, SEQ ID NO.: 32, SEQ ID NO.: 33, SEQ ID NO.: 34, SEQ ID NO.: 35, and SEQ ID NO.: 36.

The genomic insulator elements described herein can be used in the design of a vector composition e.g., for effecting gene therapy and/or treating a disease. At a minimum, the viral vectors described herein comprise at least one copy of a high potency genomic insulator element. However, viral vectors comprising multiple copies (i.e., 2 or more) of a single genomic insulator element or viral vectors comprising multiple different genomic insulator elements are also contemplated herein.

Accordingly in some embodiments, the vector comprises at least 1, at least 2, at least 3, at least 4, at least 5, at least 6, at least 7, at least 8, at least 9, at least 10, or more copies of a single genomic insulator element. In other embodiments, the vector comprises at least 2, at least 3, at least 4, at least 5, at least 6, at least 7, at least 8, at least 9 or more different genomic insulator elements. Vectors that comprise at least two different genomic insulator elements can also comprise at least 1, at least 2, at least 3, at least 4, at least 5, at least 6, at least 7, at least 8, at least 9, at least 10, or more copies of one or more of the genomic insulator elements. One of skill in the art can readily design vectors to include multiple copies or multiple genomic insulator elements which can balance the enhancer blocking activity of the vector with an overall insert size conducive for viral vector constraints.

Vectors

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

Essentially any viral vector can be used with the compositions and methods described herein, particularly since the use of the genomic insulator elements described herein can prevent inappropriate read-through of expression and therefore mitigates the carcinogenic effect of the viral vector in a subject.

In one embodiment, the viral vector comprising a genomic insulator element as described herein is a retroviral vector. The term "retroviral vector" refers to a viral vector or a plasmid containing structural and functional genetic elements that are primarily derived from a retrovirus. The term retrovirus is intended to encompass lentiviral vectors.

Also contemplated for use herein are "hybrid vectors." The term "hybrid" refers to a vector, LTR or other nucleic acid containing both retroviral, (e.g., lentiviral sequences) and non-lentiviral viral sequences. Such viral sequences can include, for example, sequences for reverse transcription, replication, integration and/or packaging sequences, non-structural proteins, and/or polymerase recognition sites.

The use of a genomic insulator element is particularly important in vectors that are incorporated into the genome (e.g., retroviral vectors), however the use of an adenoviral vector, an adeno-associated viral vector (AAV), or components thereof can also include a genomic insulator element. The AAV vector can be selected from the group consisting of serotype 1, 2, 3, 4, 5, 6, 7, 8, 9, and 10 or a chimeric AAV derived therefrom (Wu et al., 2006, Mol Therapy 14:316-27; Bowles et al., 2012, Mol Therapy 20:443-455). In general, for transduction in mice, AAV serotype 6 and AAV serotype 9 are particularly suitable, while for gene transfer into a human, AAV serotypes 1, 6, 8 and 9 are preferred.

Recombinant viral vectors can be generated according to standard techniques. Prior to their in vivo application viral vectors may be desalted by gel filtration methods, such as sepharose columns, and purified by subsequent filtering. Purification reduces potential deleterious effects in the subject to which the vectors are administered. The administered virus is substantially free of wild-type and replication-competent virus. The purity of the virus can be proven by suitable methods, such as sodium dodecyl sulfate-polyacrylamide gel electrophoresis (SDS-PAGE) followed by silver staining.

As will be appreciated by one of ordinary skill in the art, viral vectors are typically preferred for administration of nucleic acid sequences to a subject (e.g., a human), however the genomic insulator element(s) described herein are contemplated for use with any suitable gene therapy vector or even with plasmid or naked nucleic acid sequences.

Vector Components

The vectors described herein can include any number of sequences known to those of skill in the art, such as promoters (e.g., constitutive or inducible), enhancers, long-terminal repeats (LTRs), multiple cloning sites, restriction sequences, and the like. It will be appreciated by those of ordinary skill in the art that a vector can be designed to include any number of optional sequences e.g., to enhance expression of a therapeutic agent in a subject. Some non-limiting examples of these sequences, referred to herein as "viral components" are described herein.

The vectors described herein can contain zero, one or more of the following components: promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, or epitope tags.

Promoters used with the vector compositions described herein can be constitutive, inducible, or tissue-specific.

As used herein, the term "constitutive promoter" refers to a promoter that continually or continuously allows for transcription of an operably linked sequence. Constitutive promoters may be a "ubiquitous promoter" that allows expression in a wide variety of cell and tissue types or a "tissue-specific promoter" that allows expression in a restricted variety of cell and tissue types. Illustrative ubiquitous promoters include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus Orions et al., Nature Biotechnology 25, 1477-1482 (2007)), a Ubiquitin C promoter (UBC), a phosphoglycerate kinase-1 (PGK) promoter, a cytomegalovirus enhancer/chicken β-actin (CAG) promoter, and a β-actin promoter.

In one embodiment, it may be desirable to use a tissue-specific promoter to achieve cell type specific, lineage specific, or tissue-specific expression of a desired polynucleotide sequence. Illustrative examples of tissue specific promoters include, but are not limited to: an B29 promoter (B cell expression), a runt transcription factor (CBFa2) promoter (stem cell specific expression), an CD14 promoter (monocytic cell expression), an CD43 promoter (leukocyte and platelet expression), an CD45 promoter (hematopoietic cell expression), an CD68 promoter (macrophage expression), a CYP450 3A4 promoter (hepatocyte expression), an desmin promoter (muscle expression), an elastase 1 promoter (pancreatic acinar cell expression, an endoglin promoter (endothelial cell expression), a fibroblast specific protein 1 promoter (FSP1) promoter (fibroblast cell expression), a fibronectin promoter (fibroblast cell expression), a fms-related tyrosine kinase 1 (FLT1) promoter (endothelial cell expression), a glial fibrillary acidic protein (GFAP) promoter (astrocyte expression), an insulin promoter (pancreatic beta cell expression), an integrin, alpha 2b (ITGA2B) promoter (megakaryocytes), an intracellular adhesion molecule 2 (ICAM-2) promoter (endothelial cells), an interferon beta (IFN-β) promoter (hematopoietic cells), a keratin 5 promoter (keratinocyte expression), a myoglobin (MB) promoter (muscle expression), a myogenic differentiation 1 (MYOD1) promoter (muscle expression), a nephrin promoter (podocyte expression), a bone gamma-carboxyglutamate protein 2 (OG-2) promoter (osteoblast expression), an 3-oxoacid CoA transferase 2B (Oxct2B) promoter, (haploid-spermatid expression), a surfactant protein B (SP-B) promoter (lung expression), a synapsin promoter (neuron expression), and a Wiskott-Aldrich syndrome protein (WASP) promoter (hematopoietic cell expression).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue-specific expression. Certain embodiments of the methods and compositions herein provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, Gene, 323:67), the cumate inducible gene switch (WO 2002/088346), tetracycline-dependent regulatory systems, etc.

Conditional expression can also be achieved by using a site-specific DNA recombinase. According to certain embodiments, the vector comprises at least one (typically two) site(s) for recombination mediated by a site-specific recombinase. As used herein, the terms "recombinase" or "site-specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The vectors may comprise one or more recombination sites for any of a wide variety of site-specific recombinases. It is to be understood that the target site for a site-specific recombinase is in addition to any site(s) required for integration of a vector, e.g., a retroviral vector or lentiviral vector. As used herein, the terms "recombination sequence," "recombination site," or "site-specific recombination site" refer to a particular nucleic acid sequence which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see e.g., Sauer, B., Current Opinion in Biotechnology 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), F1, F2, F3 (Schlake and Bode, 1994), F4, F5 (Schlake and Bode, 1994), FRT(LE) (Senecoff et al., 1988), FRT(RE) (Senecoff et al., 1988). Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000).

In one embodiment, the vectors described herein can include an "internal ribosome entry site" or "IRES," which refers to an element that promotes direct internal ribosome entry to the initiation codon, such as ATG, of a cistron (a protein encoding region), thereby leading to the cap-independent translation of the gene. In particular embodiments, the vectors contemplated herein may include one or more genes of interest that encode one or more polypeptides (e.g., therapeutic proteins). To achieve efficient translation of each of the plurality of polypeptides, the polynucleotide sequences can be separated by one or more IRES sequences or polynucleotide sequences encoding self-cleaving polypeptides.

As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO: 37), where R is a purine (A or G) (Kozak, 1986. Cell. 44(2):283-92, and Kozak, 1987. Nucleic Acids Res. 15(20):8125-48).

In particular embodiments, vectors comprise a polyadenylation sequence 3' of a polynucleotide encoding a polypeptide to be expressed. Polyadenylation sequences can promote mRNA stability by addition of a polyA tail to the 3' end of the coding sequence and thus, contribute to increased translational efficiency. Recognized polyadenylation sites include an ideal polyA sequence (e.g., ATTAAA, ATTAAA AGTAAA), a bovine growth hormone polyA sequence (BGHpA), a rabbit β-globin polyA sequence (rβgpA), or another suitable heterologous or endogenous polyA sequence known in the art.

If desired, the vectors described herein can comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977. Cell 11:223-232) and adenine phosphoribosyltransferase (Lowy et al., 1990. Cell 22:817-823) genes which can be employed in tk- or aprt-cells, respectively.

In one embodiment, the vector composition described herein comprises a long-terminal repeat. The term "long terminal repeat (LTR)" typically refers to domains of base pairs located at the ends of retroviral DNAs which, in their natural sequence context, are direct repeats and contain U3, R and U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The vectors described herein can comprise an entire LTR or can comprise one or more regions selected from the group consisting of the U3, R, and U5 regions.

In other embodiments, the vector can comprise modified 5' and/or 3' LTRs. Modifications of the 3' LTR are often made to improve the safety of lentiviral or retroviral systems by rendering viruses replication-defective. As used herein, the term "replication-defective" refers to a virus that is not capable of complete, effective replication such that infective virions are not produced (e.g., replication-defective lentiviral progeny). In contrast, the term "replication-competent" refers to wild-type virus or mutant virus that is capable of replication, such that viral replication of the virus is capable of producing infective virions (e.g., replication-competent lentiviral progeny).

The vectors described herein can also be "self-inactivating" (SIN) vectors, e.g., a replication-defective vector in which the right (3') LTR enhancer-promoter region, known as the U3 region, has been modified (e.g., by deletion or substitution) to prevent viral transcription beyond the first round of viral replication. In a further embodiment, the 3' LTR is modified such that the U5 region is replaced, for example, with an ideal poly(A) sequence.

An additional safety enhancement can be provided by replacing the U3 region of the 5' LTR with a heterologous promoter to drive transcription of the viral genome during production of viral particles. Examples of heterologous promoters which can be used include, for example, simian virus 40 (SV40) (e.g., early or late), cytomegalovirus (CMV) (e g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system.

In addition, a vector can further contain a packaging sequence (e.g., the psi sequence), a "trans-activation response" genetic element, an "R-region", a reverse transcription site, a FLAP element, an export element, a post-transcriptional regulatory element, and/or a polyadenylation site, among others. One of ordinary skill in the art will recognize the use of such elements and can incorporate them into the design of the vectors as described herein, when desired.

In one embodiment, the vector can further contain at least one element directing the efficient termination and polyadenylation of the heterologous nucleic acid transcripts to increase heterologous gene expression. Transcription termination signals are generally found downstream of the polyadenylation signal. The term "polyA site" or "polyA sequence" as used herein denotes a DNA sequence which directs both the termination and polyadenylation of the nascent RNA transcript by RNA polymerase II. Efficient polyadenylation of the recombinant transcript is desirable as transcripts lacking a poly A tail are unstable and are rapidly degraded. Illustrative examples of polyA signals that can be used in a vector include an ideal polyA sequence (e.g., AATAAA, ATTAAA AGTAAA), a bovine growth hormone polyA sequence (BGHpA), a rabbit β-globin polyA sequence (rβgpA), or another suitable heterologous or endogenous polyA sequence known in the art.

The vectors described herein, when used for gene therapy, can permit expression of a therapeutic agent. A therapeutic agent can be a bioactive protein, a therapeutic protein, a dominant negative mutant, an RNA interference agent, or an miRNA. In one embodiment, the sequence encoding the therapeutic agent is included in a nucleic acid cassette.

The term 'nucleic acid cassette" as used herein refers to genetic sequences within the vector which can express an RNA, and subsequently a protein of interest. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In one embodiment, the nucleic acid cassette contains the sequence of a therapeutic gene used to treat disease. The cassette can be removed and inserted into a plasmid or viral vector as a single unit.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are known by those of skill in the art. A retroviral/lentiviral transfer vector can be introduced into a packaging cell line, via transfection, transduction or infection, to generate a producer cell or cell line. The packaging vectors can be introduced into human cells or cell lines by standard methods including, e.g., calcium phosphate transfection, lipofection or electroporation. In some embodiments, the packaging vectors are introduced into the cells together with a dominant selectable marker, such as neomycin, hygromycin, puromycin, blastocidin, zeocin, thymidine kinase, DHFR, Gln synthetase or ADA, followed by selection in the presence of the appropriate drug and isolation of clones. A selectable marker gene can be linked physically to genes encoding by the packaging vector, e.g., by IRES or self-cleaving viral peptides.

Viral envelope proteins (env) determine the range of host cells which can ultimately be infected and transformed by recombinant retroviruses generated from the cell lines. In the case of lentiviruses, such as HIV-1, HIV-2, SIV, FIV and EIV, the env proteins include gp41 and gp120. Preferably, the viral env proteins expressed by packaging cells are encoded on a separate vector from the viral gag and pol genes, as has been previously described.

Illustrative examples of retroviral-derived env genes which can be employed in the vectors and constructs described herein include, but are not limited to: MLV envelopes, 10A1 envelope, BAEV, FeLV-B, RD114, SSAV, Ebola, Sendai, FPV (Fowl plague virus), and influenza virus envelopes. Similarly, genes encoding envelopes from RNA viruses (e.g., RNA virus families of Picornaviridae, Caliciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BLV, EBV, CAEV, SNV, ChTLV, STLV, MPMV, SMRV, RAV, FuSV, MH2, AEV, AMV, CT10, EIAV.

In other embodiments, envelope proteins for pseudotyping a virus as useful for vectors or constructs described herein include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Bar virus (EBV), human herpes viruses (HHV), human herpes virus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephalitis causing virus.

In one embodiment, the vector tropism can be modified by expression of an antibody or antigen binding fragment on the surface of the vector particle.

Identifying a High Potency Genomic Insulator Element

Provided herein are methods for identifying a high potency genomic insulator element. Briefly, the methods comprise assessing the number of instances of a CTCF binding motif in a genome and aligning them with data from ChIP sequencing for CTCF to determine CTCF binding motifs with high occupancy, optionally classifying the CTCF binding motifs by the presence of a 14 bp core sequence, optionally ranking the classes from highest occupancy to lowest (or vice versa), selecting candidates for functional study and testing for enhancer blocking activity. In one embodiment, the method for identifying a high potency genomic insulator element comprises the steps outlined in FIG. 1.

In another embodiment, the method for identifying a high potency genomic insulator element comprises the methods outlined in the working examples.

Genotoxicity

The use of gene therapy vectors in human is limited by their toxicity, particularly the tendency to produce genotoxicity from the activation of cellular oncogenes by the enhancers present in the viral vector. Such genotoxicity is evidenced by, for example, the appearance of hematopoietic malignancies in humans treated with gene therapy vectors, and, for example, an increased number of tumors in experimental animals administered viral vectors. While genotoxicity at any level is generally undesirable, the incidence of animals with tumors associated with genotoxicity of the vectors described herein is reduced by at least 50%, at least 75%, at least 80%, at least 90%, at least 95%, at least 98%, at least 99% or more as compared to a vector lacking the genomic insulator element(s) but otherwise identical. In some embodiments, the incidence of tumors associated with genotoxicity of the vectors described herein is reduced by at least 1-fold, at least 2-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 200-fold or more compared to a vector lacking the genomic insulator element(s) but otherwise identical.

Genotoxicity can be determined with various in vitro and in vivo methods including measuring the number or extent of tumors associated with vector administration.

In one embodiment, genotoxicity is determined using a tumor transplant genotoxicity assay. In this assay, a cell line transduced with gammaretroviral vectors is transplanted into mice and the number of tumors or rates of tumor free survival are determined in the mice. This assay allows quantification of genotoxic effects by assessing e.g., rates of tumor free survival or overall rate of tumor formation.

Gene Therapy Administration & Efficacy

As used herein, the terms "treat" "treatment" "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced.

Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a given disease or disorder, diminishment of extent of disease, stabilized disease (i.e., not worsening), delay or slowing of progression of the disease, amelioration or palliation of the disease state, and remission (whether partial or total). The term "treatment" of a disease also includes providing at least partial relief from the symptoms or side-effects of the disease (including palliative treatment).

In one embodiment, as used herein, the term "prevention" or "preventing" when used in the context of a subject refers to stopping, hindering, and/or slowing the development of a given disease or disorder.

As used herein, the term "therapeutically effective amount" means that amount necessary, at least partly, to attain the desired effect, or to delay the onset of, inhibit the progression of, or halt altogether, the onset or progression of the particular disease or disorder being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. In some embodiments, a maximum dose of a therapeutic agent is used, that is, the highest safe dose according to sound medical judgment. It will be understood by those of ordinary skill in the art, however, that a lower dose or tolerable dose that is effective can be administered for medical reasons, psychological reasons or for virtually any other reason.

In one embodiment, a therapeutically effective amount of a pharmaceutical formulation, or a composition described herein for a method of treating a given disease or disorder is an amount sufficient to reduce the level of at least one symptom of the disease or disorder as compared to the level in the absence of the compound, the combination of compounds, the pharmaceutical composition/formulation of the composition. In other embodiments, the amount of the composition administered is preferably safe and sufficient to treat, delay the development of disease, and/or delay onset of the disease. In some embodiments, the amount can thus cure or result in amelioration of the symptoms of the disease, slow the course of the disease, slow or inhibit a symptom of the disease, or slow or inhibit the establishment or development of secondary symptoms associated with the disease. While effective treatment need not necessarily initiate complete regression of the disease, such effect would be effective treatment. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount." However, for any given case, an appropriate "effective amount" can be determined by a skilled artisan according to established methods in the art using only routine experimentation.

Pharmaceutical Compositions

Provided herein are vector compositions that are useful for treating and preventing a variety of different diseases and/or disorders in a subject. In one embodiment, the composition is a pharmaceutical composition. The composition can comprise a therapeutically or prophylactically effective amount of a vector encoding a polynucleotide or therapeutic agent.

The composition can optionally include a carrier, such as a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions. Formulations suitable for parenteral administration can be formulated, for example, for intravenous, intramuscular, intradermal, intraperitoneal, and subcutaneous routes. Carriers can include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, preservatives, liposomes, microspheres and emulsions.

Therapeutic compositions contain a physiologically tolerable carrier together with the vectors described herein, dissolved or dispersed therein as an active ingredient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmaceutical composition that contains active ingredients dissolved or dispersed therein is understood in the art and need not be limited based on formulation. Typically such compositions are prepared as injectable either as liquid solutions or suspensions; however, solid forms suitable for solution, or suspension in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition for use with the methods described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Examples of such additional liquid phases are glycerin, vegetable oils such as cottonseed oil, and water-oil emulsions. The amount of a vector to be administered herein that will be effective in the treatment of a particular disorder or condition will depend on the nature of the disorder or condition, the expression of the therapeutic agent, and can be determined by standard clinical techniques.

While any suitable carrier known to those of ordinary skill in the art can be employed in the pharmaceutical composition, the type of carrier will vary depending on the mode of administration. Compositions for use as described herein can be formulated for any appropriate manner of administration, including for example, topical, oral, nasal, intravenous, intracranial, intraperitoneal, subcutaneous or intramuscular administration. For parenteral administration, such as intramuscular or subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) can also be employed as carriers for the pharmaceutical compositions. Suitable biodegradable microspheres are disclosed, for example, in U.S. Pat. Nos. 4,897,268 and 5,075,109. Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions as described herein can be formulated as a lyophilizate. Compounds can also be encapsulated within liposomes. The compositions described herein can be administered as part of a sustained release formulation (i.e., a formulation such as a capsule or sponge that affects a slow release of the vectors following administration). Such formulations can generally be prepared using well known technology and administered by, for example, oral, rectal or subcutaneous implantation, or by implantation at the desired target site. Sustained-release formulations can contain a vector, polypeptide, polynucleotide dispersed in a carrier matrix and/or contained within a reservoir surrounded by a rate controlling membrane. Carriers for use within such formulations are biocompatible, and can also be biodegradable; preferably the formulation provides a relatively constant level of active component release. The amount of active compound contained within a sustained release formulation depends upon the site of implantation, the rate and expected duration of release and the nature of the condition to be treated or prevented.

Dosage and Administration

Treatment includes prophylaxis and therapy. Prophylaxis or treatment can be accomplished by a single direct injection at a single time point or multiple time points. Administration can also be nearly simultaneous to multiple sites. Patients or subjects include mammals, such as human, bovine, equine, canine, feline, porcine, and ovine animals as well as other veterinary subjects. Preferably, the patients or subjects are human.

In one aspect, the methods described herein provide a method for treating a disease or disorder in a subject. In one embodiment, the subject can be a mammal. In another embodiment, the mammal can be a human, although the approach is effective with respect to all mammals. The method comprises administering to the subject an effective amount of a pharmaceutical composition comprising a vector as described herein in a pharmaceutically acceptable carrier.

The dosage range for the agent depends upon the potency, the expression level of the therapeutic agent and includes amounts large enough to produce the desired effect, e.g., reduction in at least one symptom of the disease to be treated. The dosage should not be so large as to cause unacceptable adverse side effects. Generally, the dosage will vary with the type of inhibitor expressed from the vector (e.g., an antibody or fragment, small molecule, siRNA, etc.) or activator (e.g., recombinant polypeptide, peptide, peptidomimetic, small molecule, etc.), and with the age, condition, and sex of the patient. The dosage can be determined by one of skill in the art and can also be adjusted by the individual physician in the event of any complication. Typically, the dosage of the therapeutic agent and/or the vector composition ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight.

In some embodiments, the vectors are administered at a multiplicity of infection (MOI) of at least 5, at least 10, at least 20, at least 30, at least 40, at least 50, at least 100, at least 200, at least 500 or more.

In other embodiments, the vectors are administered at a titer of at least $1\times10^5$, $1\times10^6$, $1\times10^7$, $1\times10^8$, $1\times10^9$, $1\times10^{10}$, $1\times10^{11}$, $1\times10^{12}$ or more.

Repeated administration can be performed as necessary to maintain therapeutic efficacy.

A therapeutically effective amount is an amount of a vector or expressed therapeutic agent that is sufficient to produce a statistically significant, measurable change in at least one symptom of a disease (see "Efficacy Measurement" below). Alternatively, a therapeutically effective amount is an amount of an agent that is sufficient to produce a statistically significant, measurable change in the expression level of a biomarker associated with the disease in the subject. Such effective amounts can be gauged in clinical trials as well as animal studies for a given agent.

The vector compositions can be administered directly to a particular site (e.g., intramuscular injection, intravenous, into a specific organ) or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Efficacy Measurement

The efficacy of a given treatment for a disease can be determined by the skilled clinician. However, a treatment is considered "effective treatment," as the term is used herein, if any one or all of the signs or symptoms of the disease to be treated is/are altered in a beneficial manner, other clinically accepted symptoms or markers of disease are improved, or even ameliorated, e.g., by at least 10% following treatment with a vector as described herein. Efficacy can also be measured by failure of an individual to worsen as assessed by stabilization of the disease, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the disease; or (2) relieving the disease, e.g., causing regression of symptoms; and (3) preventing or reducing the likelihood of the development of the disease or preventing secondary issues associated with the disease.

It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The inventors describe herein an approach for identifying chromatin insulators in the human genome that combines genomic informatics and CTCF ChIP-seq to classify the CTCF sites of the human genome according to their CTCF occupancy. The inventors find that only a minority of the CTCF sites of the human genome are occupied by CTCF and that the occupancy frequency determines the probability that the site will function as a enhancer-blocking insulator. All sites with 98% to 100% CTCF occupancy that were functionally analyzed are robust enhancer-blocking insulators. The majority of these insulators exhibit enhancer-blocking activity that is superior to that of the cHS4 insulator. Their sequences are short (119 to 284 bp) and thus can easily be accommodated in gene therapy vectors; furthermore, they have no detrimental effects on the titers of lentiviral vectors. The inventors also provide proof of principle that these elements can decrease the risk of lentiviral vector-mediated carcinogenesis in a murine model.

Mining the Human Genome for Chromatin Insulators

Figure 5A:
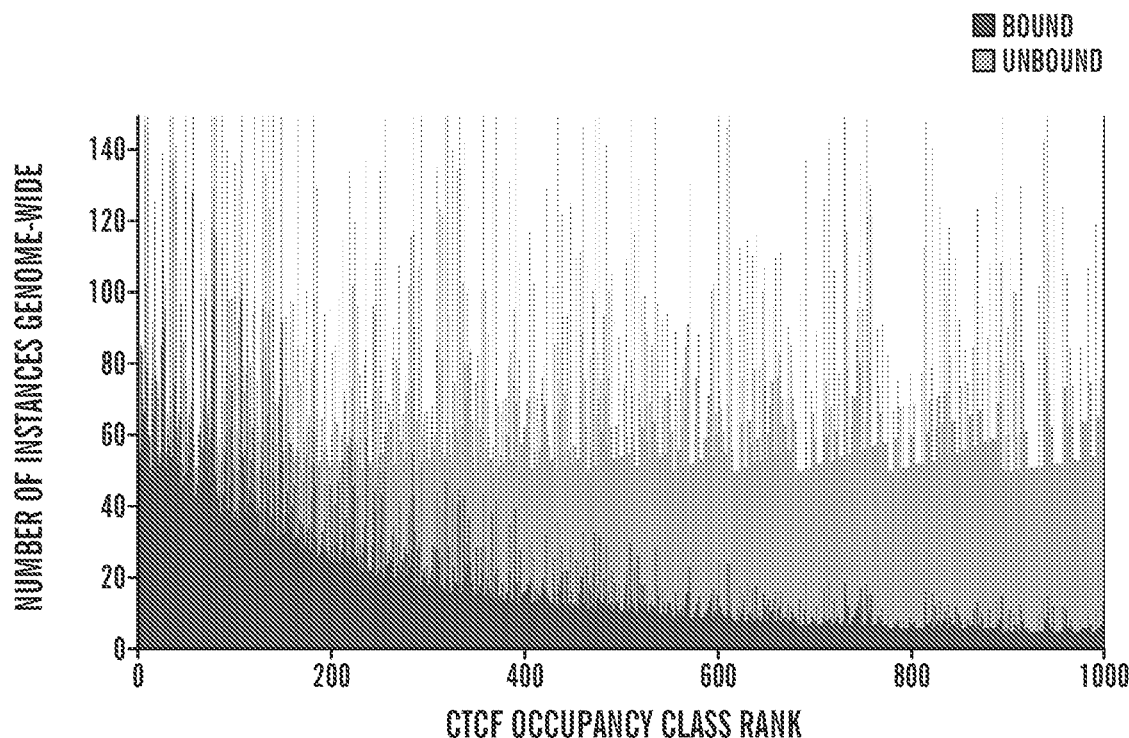
FIGS. 5A-5B Correlation of specific CTCF binding motifs with in vivo occupancy.
Figure 5B:
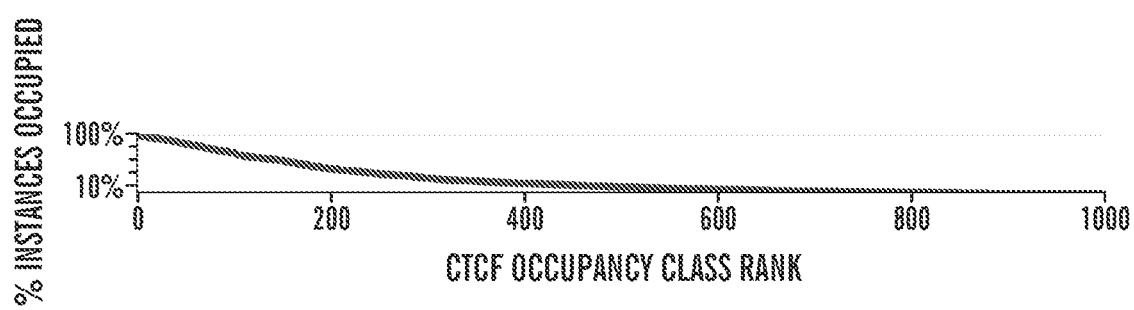

The inventors identified candidate insulator sequences based on genome-wide in vivo occupancy profiling of CTCF in K562 cells (FIG. 1). Although the majority of CTCF binding sites are distinguished by a conserved sequence motif (15), most instances of this sequence genome-wide are not bound by CTCF (FIG. 5). Using an informatics approach to scan the genome, the inventors identified 22,579,591 instances of CTCF motifs ($P<10^{-2}$). Only 205,227 (0.9%) of these overlapped ChIP-seq peaks for CTCF binding, indicating that most sequence elements matching the CTCF motif have a low probability of being bound in vivo.

To identify sequence features associated with a high affinity for CTCF, the inventors grouped these potential recognition sequences genome-wide into classes of exact sequence identity (FIG. 1). The inventors focused on the 14-bp sequence at the high-information core of the CTCF motif, a GC-rich region that has been shown sufficient to engage zinc fingers 4-8 (27). CTCF motifs were grouped into classes of identical 14 bp CTCF core sequences. The inventors found 82,234 classes having >50 instances of the same 14-mer throughout the genome (mean=105 instances).

To assess the inherent affinity of each class, the inventors measured the proportion of its genomic sites that were occupied by CTCF in vivo. Occupancy in K562 cells varied greatly, from 100% (where all the genomic sites of a 14-mer sequence were bound in vivo) to 0% (where no genomic site of a 14-mer sequence was bound in vivo). Genome-wide 159 CTCF sites were identified with 100% CTCF occupancy; 1624 sites with over 95% CTCF occupancy; 3499 sites with over 90% CTCF occupancy; and 77316 sites with CTCF occupancy 1% or higher (data not shown). (CTCF sequences and genomic coordinates of all the sites with CTCF occupancy higher than 1% are listed in Supplementary Table 2 of Liu et al. "Genomic discovery of potent chromatin insulators for human gene therapy" Nature (2015) 33(2): 198-203, which is incorporated herein by reference in its entirety). The classes exhibiting ≥10% CTCF occupancy represented a minority (16%) of genome-wide CTCF binding. Studies summarized in FIG. 6 demonstrated a direct correlation between the top 1000 CTCF occupancy class rankings in K562 cells and occupancy in 18 other cell lines, indicating a ubiquitous activity profile for the high-occupancy CTCF sites.

To determine whether the high-affinity CTCF sites identified through this method function as enhancer-blocking insulators, the inventors selected representative genomic sequences from sites of high or low CTCF occupancy (Tables 1 and 2).

TABLE 1

CTCF classes and sequences used for functional assays

| | Rank | Class | Core Sequence | Number of occurrences in the human genome | CTCF occupancy percent* |
|---|---|---|---|---|---|
| High-affinity | 1 | A | CACCAGGTGGCGCT | 52 | 100.0% |
| | 2 | B | CCACCAGGGGGAGC | 52 | 100.0% |
| | 3 | C | TCAGTAGAGGGCGC | 55 | 100.0% |
| | 4 | D | CCACTAGGGGGCAG | 86 | 98.8% |
| | 5 | E | CAGCAGAGGGCGCT | 84 | 98.8% |
| | 6 | F | CAGTAGAGGGCGCT | 71 | 98.6% |

TABLE 1-continued

CTCF classes and sequences used for functional assays

|  | Rank | Class | Core Sequence | Number of occurrences in the human genome | CTCF occupancy percent* |
|---|---|---|---|---|---|
| Low-affinity | 932 | G | CCCTCTCCTGGGCA | 102 | 9.8% |
|  | 943 | H | GCAGCAGAGAGCAA | 72 | 9.7% |
|  | 950 | J | CCCTCTGCTGACTG | 52 | 9.6% |

*as determined by ChIP-seq in K562 cells.

TABLE 2

Chromosomal hg18 and hg19 coordinates, CTCF sequences, and enhancer blocking activity of the CTCF elements used for functional studies.

| Class/Element | hg18 coordinates | | | CTCF Sequences | Colony Mean ± SD* | hg19 coordinates | | |
|---|---|---|---|---|---|---|---|---|
| A1 | chr1 | 76229933 | 76230115 | CACCAGGTGGCGCT | 0.081 ± 0.041 | chr1 | 76457345 | 76457527 |
| A2 | chr19 | 46342254 | 46342440 | CACCAGGTGGCGCT | 0.022 ± 0.011 | chr19 | 41650414 | 41650600 |
| A3 | chr5 | 90557806 | 90557925 | CACCAGGTGGCGCT | 0.058 ± 0.016 | chr5 | 90522050 | 90522169 |
| A4 | chr7 | 39526144 | 39526307 | CACCAGGTGGCGCT | 0.030 ± 0.022 | chr7 | 39559619 | 39559782 |
| A5 | chr9 | 123122258 | 123122485 | CACCAGGTGGCGCT | 0.087 ± 0.025 | chr9 | 124082437 | 124082664 |
| B1 | chr1 | 57070274 | 57070473 | CCACCAGGGGGAGC | 0.057 ± 0.006 | chr1 | 57297686 | 57297885 |
| B2 | chr12 | 106525547 | 106525690 | CCACCAGGGGGAGC | 0.038 ± 0.010 | chr12 | 108001417 | 108001560 |
| B3 | chr14 | 76320982 | 76321216 | CCACCAGGGGGAGC | 0.215 ± 0.120 | chr14 | 77251229 | 77251463 |
| B4 | chr20 | 61411429 | 61411552 | CCACCAGGGGGAGC | 0.151 ± 0.060 | chr20 | 61940984 | 61941107 |
| B5 | chr22 | 33876597 | 33876817 | CCACCAGGGGGAGC | 0.141 ± 0.042 | chr22 | 35546597 | 35546817 |
| C1 | chr1 | 30038520 | 30038763 | TCAGTAGAGGGCGC | 0.378 ± 0.270 | chr1 | 30265933 | 30266176 |
| C2 | chr16 | 74063175 | 74063459 | TCAGTAGAGGGCGC |  | chr16 | 75505674 | 75505958 |
| C3 | chr2 | 16570154 | 16570340 | TCAGTAGAGGGCGC | 0.040 ± 0.016 | chr2 | 16706673 | 16706859 |
| C4 | chr8 | 10168897 | 10169034 | TCAGTAGAGGGCGC |  | chr8 | 10131487 | 10131624 |
| C5 | chrX | 149602730 | 149602938 | TCAGTAGAGGGCGC | 0.250 ± 0.150 | chrX | 149852072 | 149852280 |
| D1 | chr1 | 161084397 | 161084593 | CCACTAGGGGGCAG | 0.065 ± 0.044 | chr1 | 162817773 | 162817969 |
| D2 | chr11 | 61948886 | 61949071 | CCACTAGGGGGCAG |  | chr11 | 62192310 | 62192495 |
| D3 | chr12 | 121910863 | 121911035 | CCACTAGGGGGCAG | 0.203 ± 0.086 | chr12 | 123344910 | 123345082 |
| D4 | chr17 | 16207878 | 16208078 | CCACTAGGGGGCAG | 0.281 ± 0.149 | chr17 | 16267153 | 16267353 |
| D5 | chr17 | 24468364 | 24468528 | CCACTAGGGGGCAG | 0.256 ± 0.108 | chr17 | 27444238 | 27444402 |
| E1 | chr1 | 176768124 | 176768329 | CAGCAGAGGGCGCT | 0.066 ± 0.016 | chr1 | 178501501 | 178501706 |
| E2 | chr13 | 20397008 | 20397240 | CAGCAGAGGGCGCT | 0.032 ± 0.008 | chr13 | 21499008 | 21499240 |
| E3 | chr14 | 68665824 | 68666051 | CAGCAGAGGGCGCT | 0.140 ± 0.072 | chr14 | 69596071 | 69596298 |
| E4 | chr5 | 64116126 | 64116362 | CAGCAGAGGGCGCT | 0.062 ± 0.022 | chr5 | 64080370 | 64080606 |
| E5 | chr5 | 170702087 | 170702300 | CAGCAGAGGGCGCT | 0.098 ± 0.029 | chr5 | 170769482 | 170769695 |
| F1 | chr12 | 55856009 | 55856202 | CAGTAGAGGGCGCT | 0.053 ± 0.015 | chr12 | 57569742 | 57569935 |
| F2 | chr12 | 57793909 | 57794148 | CAGTAGAGGGCGCT | 0.110 ± 0.106 | chr12 | 59507642 | 59507881 |
| F3 | chr12 | 102550590 | 102550826 | CAGTAGAGGGCGCT | 0.081 ± 0.028 | chr12 | 104026460 | 104026696 |

TABLE 2-continued

Chromosomal hg18 and hg19 coordinates, CTCF sequences, and enhancer blocking activity of the CTCF elements used for functional studies.

| Class/Element | hg18 coordinates | | CTCF Sequences | Colony Mean ± SD* | hg19 coordinates | |
|---|---|---|---|---|---|---|
| F4 | chr7 | 95383976 95384189 | CAGTAGAGGGCGCT | 0.173 ± 0.099 | chr7 | 95546040 95546253 |
| F5 | chr8 | 71163374 71163613 | CAGTAGAGGGCGCT | 0.404 ± 0.111 | chr8 | 71000820 71001059 |
| G1 | chr1 | 149974115 149974543 | CCCTCTCCTGGGCA | 1.000 ± 0.411 | chr1 | 151707491 151707919 |
| G2 | chr10 | 103022102 103022247 | CCCTCTCCTGGGCA | 1.040 ± 0.425 | chr10 | 103032112 103032257 |
| H1 | chr14 | 59501614 59502000 | GCAGCAGAGAGCAA | 0.705 ± 0.341 | chr14 | 60431861 60432247 |
| H2 | chr16 | 6071437 6071557 | GCAGCAGAGAGCAA | 0.382 ± 0.216 | chr16 | 6131436 6131556 |
| H3 | chr16 | 65242354 65242777 | GCAGCAGAGAGCAA | 0.753 ± 0.342 | chr16 | 66684853 66685276 |
| J1 | chr1 | 204477048 204477285 | CCCTCTGCTGACTG | 0.855 ± 0.422 | chr1 | 206310425 206310662 |
| J2 | chr15 | 72402104 72402201 | CCCTCTGCTGACTG | 0.690 ± 0.285 | chr15 | 74615051 74615148 |

*Colony means SD compared to the uninsulated control taken as 1

Figure 6:
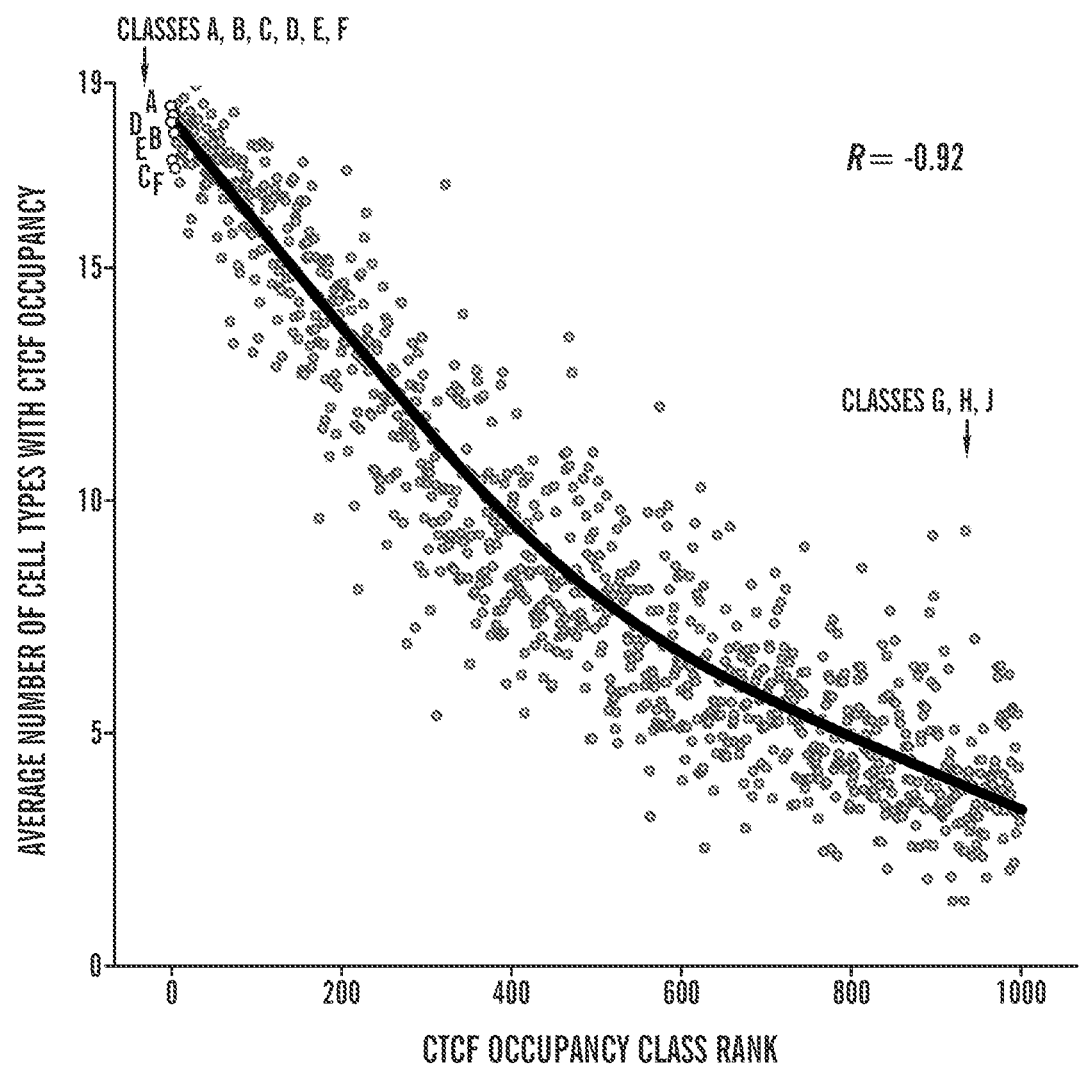
FIG. 6 Correlation between CTCF occupancy class and CTCF occupancy in multiple cell types. The CTCF occupancy of each member of the 1000 CTCF occupancy classes was assessed in 19 different cells types by ChIP-seq, and was then used to determine the average number of cells exhibiting occupancy of each CTCF occupancy class (one data point for each of 1000 classes). See FIG. 7 for the list of cell types. The trend line represents the LOESS fit. The locations of the high-occupancy classes A-F and low-occupancy classes G, H, and J are indicated. The R values are shown for the overall data set.
Figure 7:
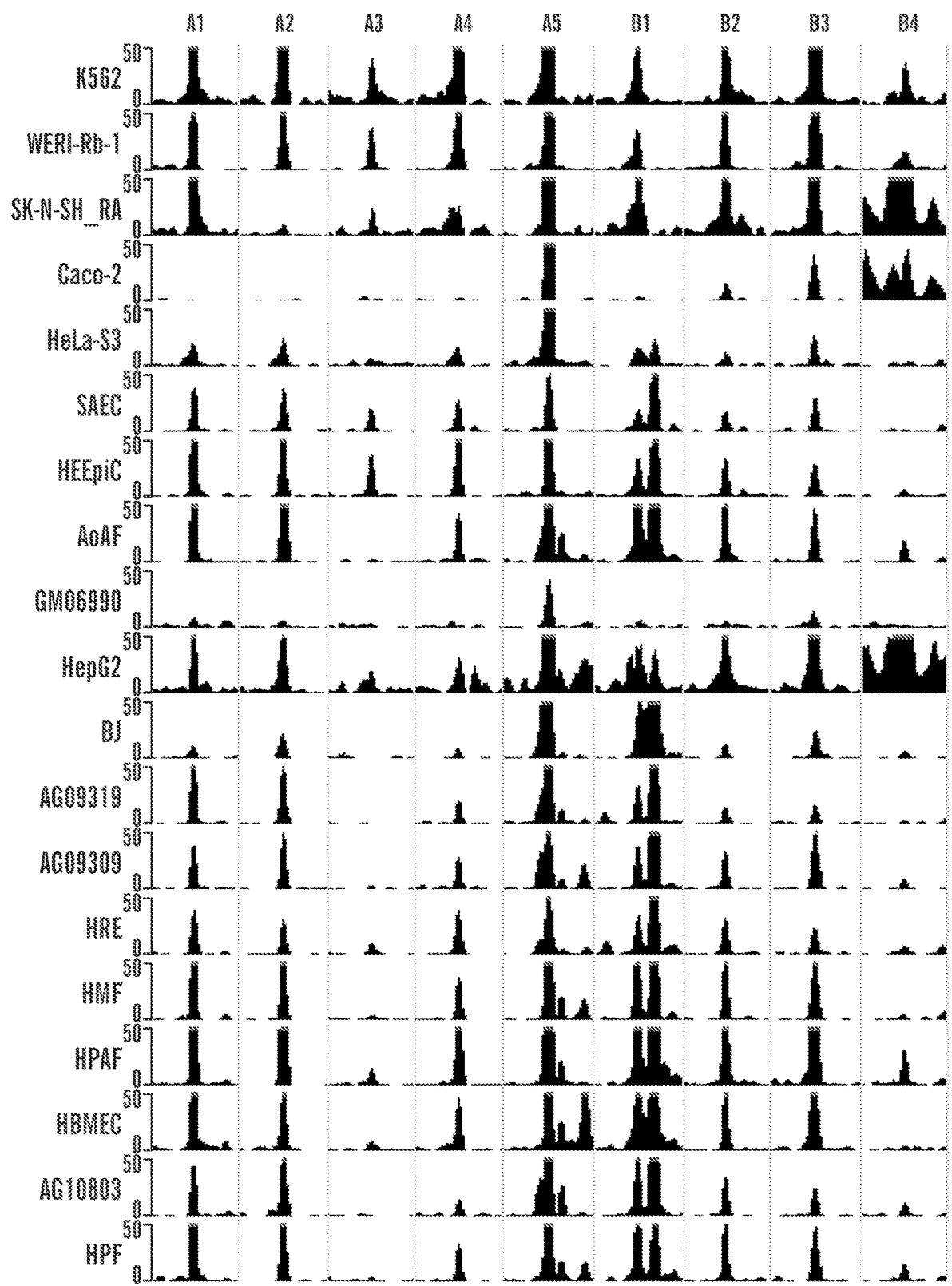
FIG. 7 DNase I hypersensitivity of high-occupancy insulator candidates in multiple cell types. The DNase I hypersensitivity profiles across the genomic regions of the indicated high-occupancy insulator candidates are shown for 19 different cell lines. Y axis: read density tracks based on DNase I-seq analysis; X axis: windows extending 1000 bp on either side of the candidate insulator sequences (see Table 2 for insulator coordinates). DNaseI profiles were derived from ENCODE.
Figure 7:
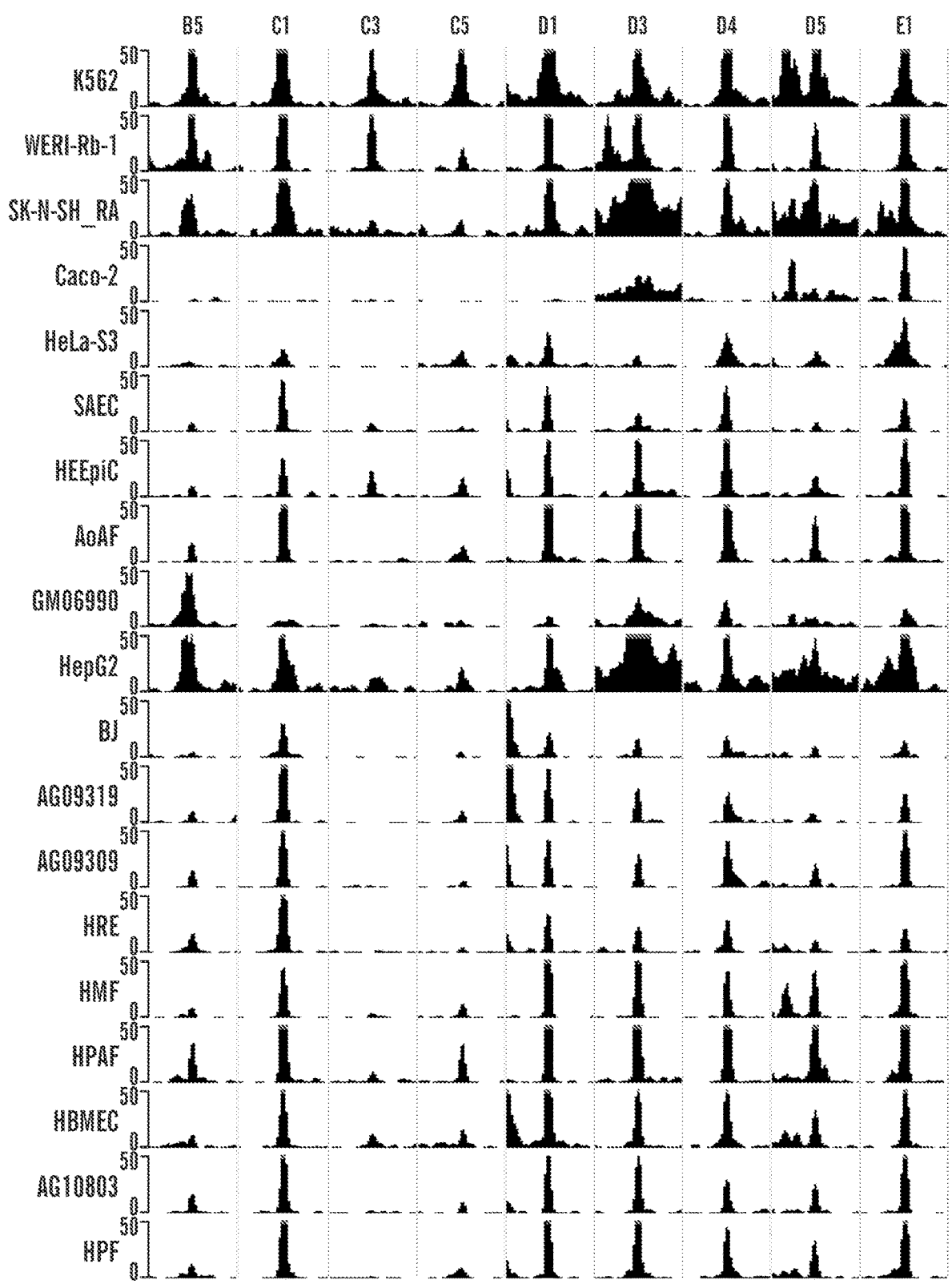
Figure 7:
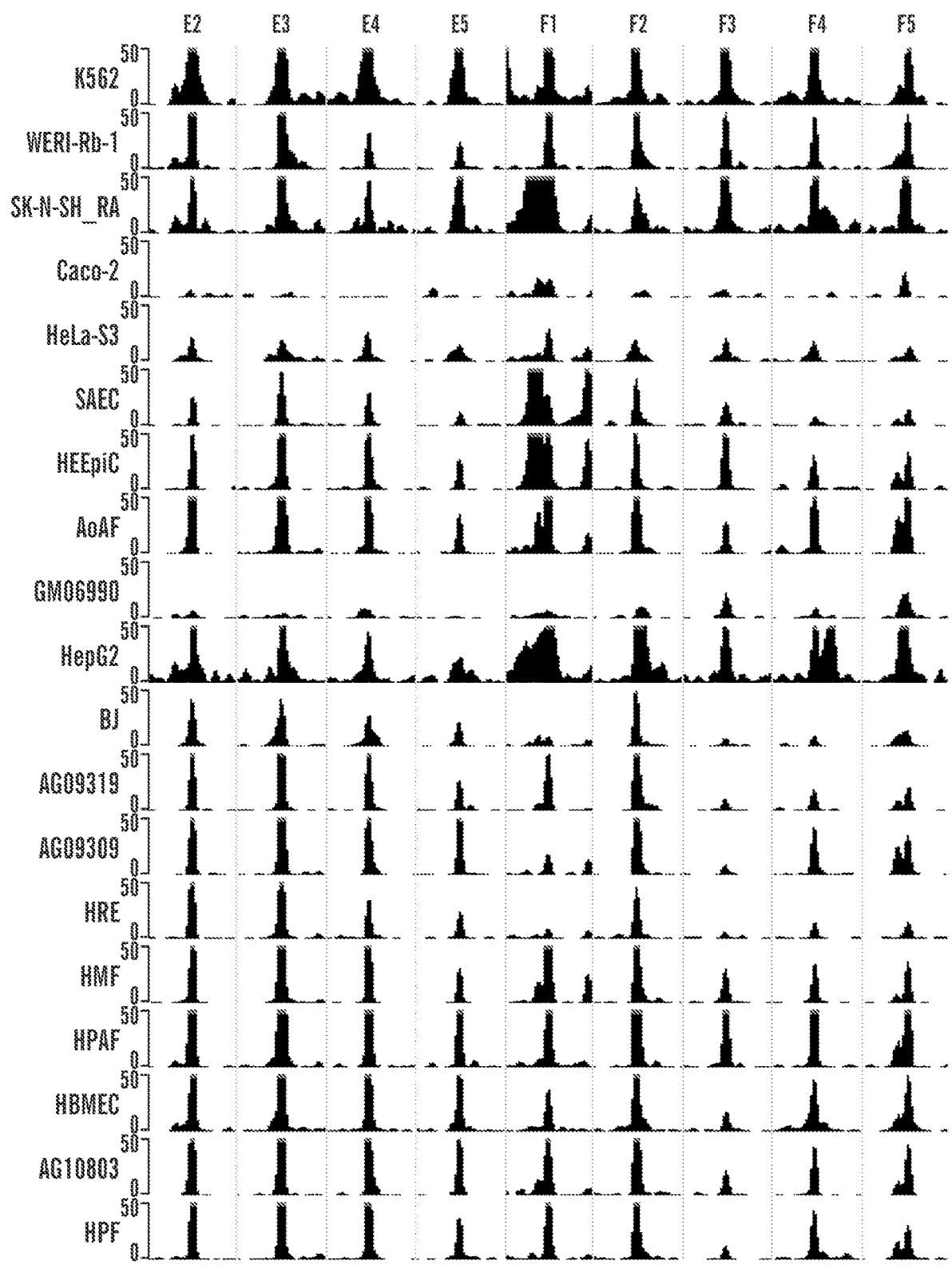

For high affinity sites the inventors selected three CTCF classes with 100% CTCF occupancy, designated as A, B and C, and three classes with 98.6 to 98.8% CTCF occupancy, designated as D, E, F (Tables 1 and 2). Five sequences from each class were selected for functional assays using two additional criteria: (i) The CTCF sites had to coincide with a DNase I Hypersensitive Site (DHS) in K562 cells and other cell types (FIG. 7); and (ii) The CTCF motif had to be occupied by CTCF in 16 of the cell types studied with ChIP-seq in the inventors' laboratory (FIG. 6). The sizes of the sequences corresponding to the DHSs overlapping with the CTCF sites ranged from 119 to 284 nucleotides, and were considered to correspond to the likely size of the insulator elements. As controls, the inventors selected several sequences from classes G, H, and J (Table 1) with a CTCF occupancy of 9.6%, 9.7% and 9.8% respectively.

Discovery of Enhancer-blocking Insulators

Figure 2A:
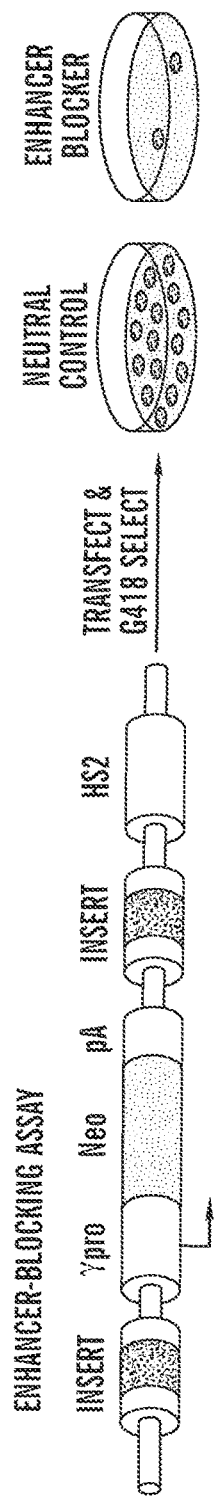
FIGS. 2A-2D Functional identification of enhancer-blocking insulators.

Candidates identified with the above approach were cloned into a plasmid reporter construct in which the drug-resistance neo gene is driven by a γ-globin gene (HBG1) promoter regulated by the enhancer of DNase I hypersensitive site 2 of the β-globin locus (FIG. 2A and Table 3).

TABLE 3

Chromosomal hg19 coordinates and primer sequences used to clone insulator candidates for functional studies.

| | Primers | | Genomic sequences (hg19) | | |
|---|---|---|---|---|---|
| Candidates | Forward | Reverse | Chr | Chr_start | Chr_end |
| A1 | CCAATCGTGGCATATCCTCT | CCTTCCTTTCTAAATGACGAGA | 1 | 76457269 | 76457568 |
| A2 | AGAGCGAGATTCCGTCTCAA | ACAATGGCTGGCCCATAGTA | 19 | 41650330 | 41650595 |
| A3 | AGGGGTTGGTCTCCCTATGT | GGGAGAGGTGGTTCAACAAA | 5 | 90521970 | 90522221 |
| A4 | TGCTTGTCCTTCCTTCCTGT | GAACTCCTGACCCCTCACAA | 7 | 39559582 | 39559824 |
| A5 | CATCCCACTCCATCACCTTC | GTAGAGACGGGGTTTCACCA | 9 | 124082406 | 124082759 |
| B1 | AGGCATGACTGGGAAGAAC | AGCCATGGAATAAAGTGCATC | 1 | 57297616 | 57297963 |
| B2 | CAGGGCTCTCCTGCAAATAG | AAGAGCCCCAAGAAGTGGAT | 12 | 108001333 | 108001655 |
| B3 | CCTCCACAACCCATGAAGTC | CCATCCACCTGCTCTTCATT | 14 | 77251132 | 77251467 |
| B4 | CTCCCGTGTGGTACCTGAG | GGATGCTGGAGGAGGTCAC | 20 | 61940925 | 61941184 |
| B5 | ACAGGGCTGCTTGTACCACT | GCGGAAACTGAACCAAAAGA | 22 | 35546561 | 35546869 |
| C1 | GTCTGAATGGTGGCCGTAGT | AGGATGGGCTATGAGGTGGT | 1 | 30265903 | 30266227 |
| C3 | GTTTCGCATCCACCTTTCAT | GTTAGCCCTGAGTGCCCATA | 2 | 16706630 | 16706937 |
| C4 | TGAGGCAGCAGCTATCCTAA | TGCTCCAAACCTACCCTTCTT | 8 | 10131406 | 10131674 |
| C5 | AGAAGCACTGCCTGGTAGG | TGGGCCTAGCTCAAAAGAAA | X | 149851977 | 149852362 |
| D1 | TCTTTTGCAATGCTCTTTGG | AGTGGTTTTGGGGTTTTCC | 1 | 162817733 | 162818013 |

TABLE 3-continued

Chromosomal hg19 coordinates and primer sequences used to clone insulator candidates for functional studies.

| Candidates | Primers | | Genomic sequences (hg19) | | |
|---|---|---|---|---|---|
| | Forward | Reverse | Chr | Chr_start | Chr_end |
| D3 | GAGACCCTCCACCCCCTAC | CTGTTGAACCCCAAACTGCT | 12 | 123344828 | 123345140 |
| D4 | GGCGTGTTTGATTTGCTTTT | AATGAGGCCTGCCACATAAG | 17 | 16267031 | 16267486 |
| D5 | CCCCTTTCCCTAAACTGGAG | GTTTTCCCCAGTCCTCTTCC | 17 | 27444171 | 27444418 |
| E1 | GCCACCTTTGGTCTTGACAT | ATCAGCGGTGTCAGTCTTCC | 1 | 178501476 | 178501802 |
| E2 | AGTTTGCAGGTGGCTTGACT | TTTGATTTCCTTCACTCTGGAA | 13 | 21498993 | 21499294 |
| E3 | CACCCCCTTACTCCACTCAA | GGCTGGCTTAAATGGTCTGA | 14 | 69596017 | 69596396 |
| E4 | TGGAATTTGTGTTGACATTG | TCAAAAGAATGTGCCAATGC | 5 | 64080190 | 64080657 |
| E5 | TGCATTTCAGGACACAGTGA | ACACTTGGGCTGAGAGTGGT | 5 | 170769377 | 170769887 |
| F1 | CCTTCAAGCCGTTCATCATT | GAACAGAAGTGTGGGGGATG | 12 | 57569695 | 57570014 |
| F2 | TGCCTTTCAGCTCCAAATCT | GGGCCACAGTGAGGTGATTA | 12 | 59507608 | 59507907 |
| F3 | GGTCAGCCACTGAGGAACT | CAATCTCACCCAACCCTTTC | 12 | 104026406 | 104026728 |
| F4 | TCGGACATTTCCCTGTCTCT | TATTGATGCCTTTGGGGAAA | 7 | 95545997 | 95546256 |
| F5 | TGGCTCAGTCATGGCTACTG | TTTCCCTACTTCTCCCACCA | 8 | 71000655 | 71001197 |
| G1 | TGGAATTGCTGCTCAGATTG | AAAATTAGCTGGGCATGGTG | 1 | 151707437 | 151708096 |
| G2 | GCAGCAAAGAAAAGCAAAG | AACCCTGTCACTGCAGCTC | 10 | 103031950 | 103032407 |
| H1 | TACCCATCAGGAAGCTCACC | CCATCCTGAATGTGATCGTG | 14 | 60431707 | 60432274 |
| H2 | TCCGGAGTTCAGGTCTCTGT | CACACGGCTGTTCACTTTGT | 16 | 6131354 | 6131789 |
| H3 | GGAAGCTCATTTACCCAGCA | ATGGAAGCCGTTGTTATTCG | 16 | 66684731 | 66685322 |
| J1 | AAGCCTGGGCTCAGTAACAA | GAGCACCTGGCACTAAAAGC | 1 | 206310373 | 206310770 |
| J2 | GGCAAATCTCTGCACCTCTC | GGGATGCATAGGGGAGGTAT | 15 | 74614873 | 74615392 |

K562 cells transfected with this construct grow in the presence of G418. When an insulator element brackets the γ-neo expression cassette, it disrupts the interaction between the enhancer and the γ promoter, resulting in decreased neo expression and decreased number of colonies in the G418 cultures. The rate of decrease in colony numbers corresponds to the efficiency with which the insulator element blocks the interaction between the enhancer and γ promoter. Negative controls included a reporter construct with no inserts, as well as reporter constructs in which functionally neutral DNA was used to bracket the γ-neo expression cassette. As a positive control, the γ-neo cassette was bracketed with the cHS4 insulator.

Figure 2B:
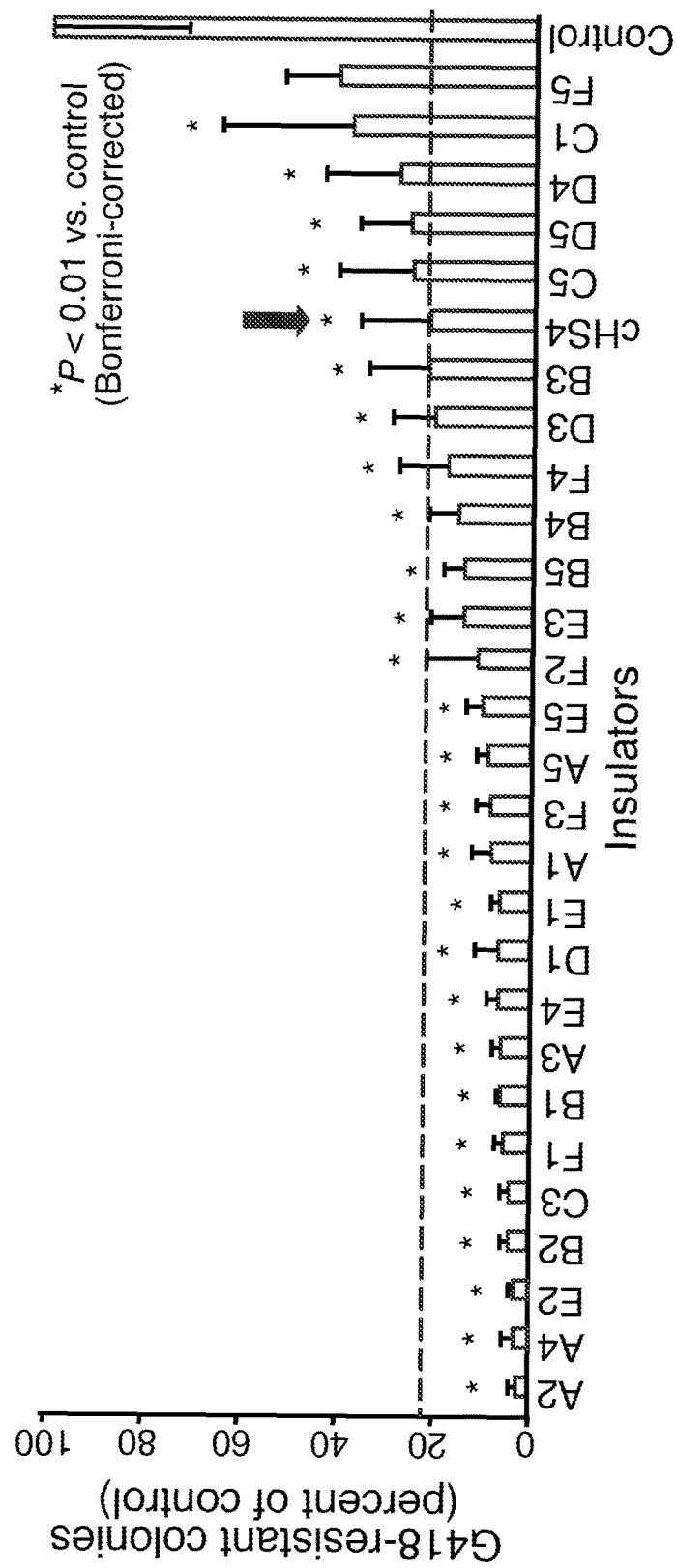
Figure 2C:
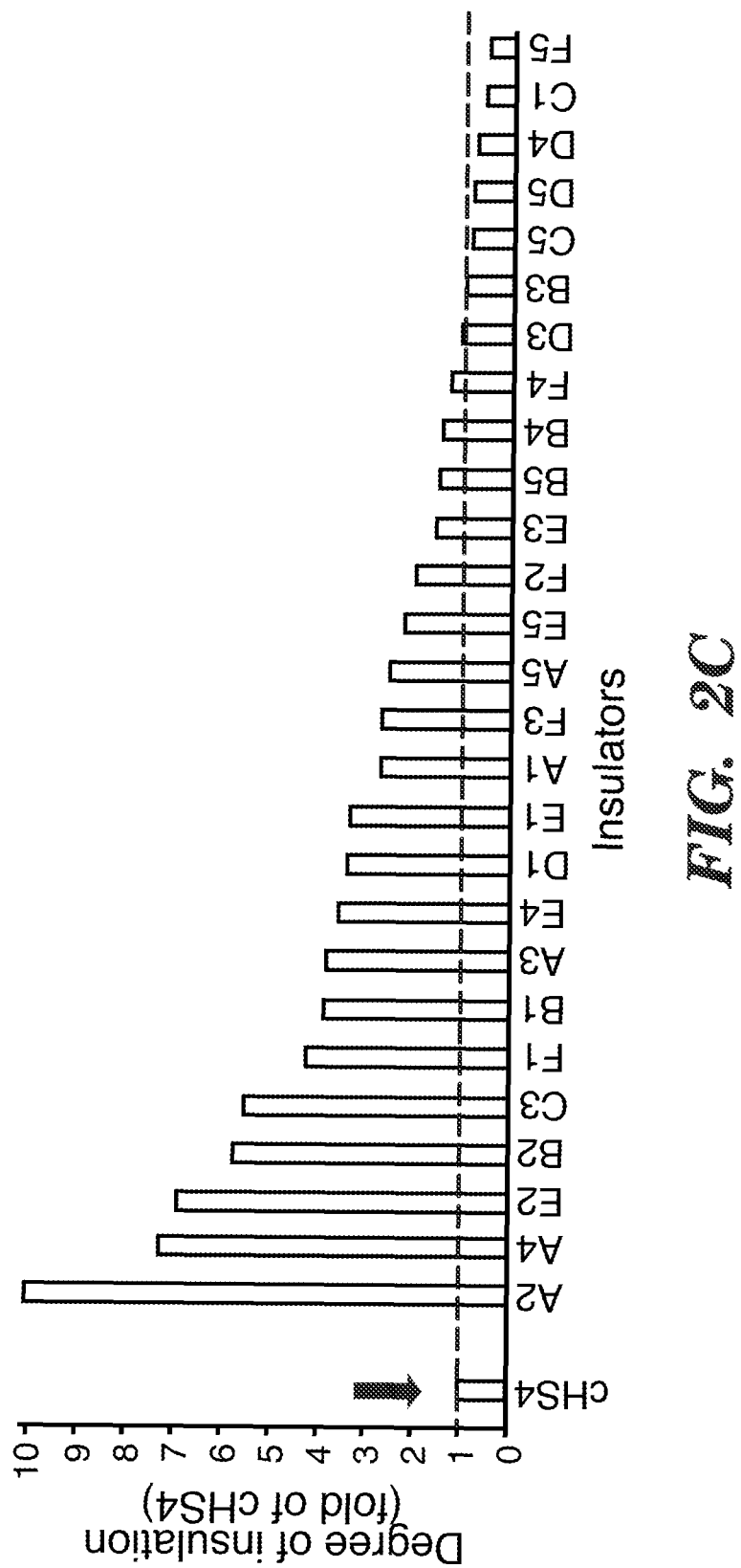
Figure 8:
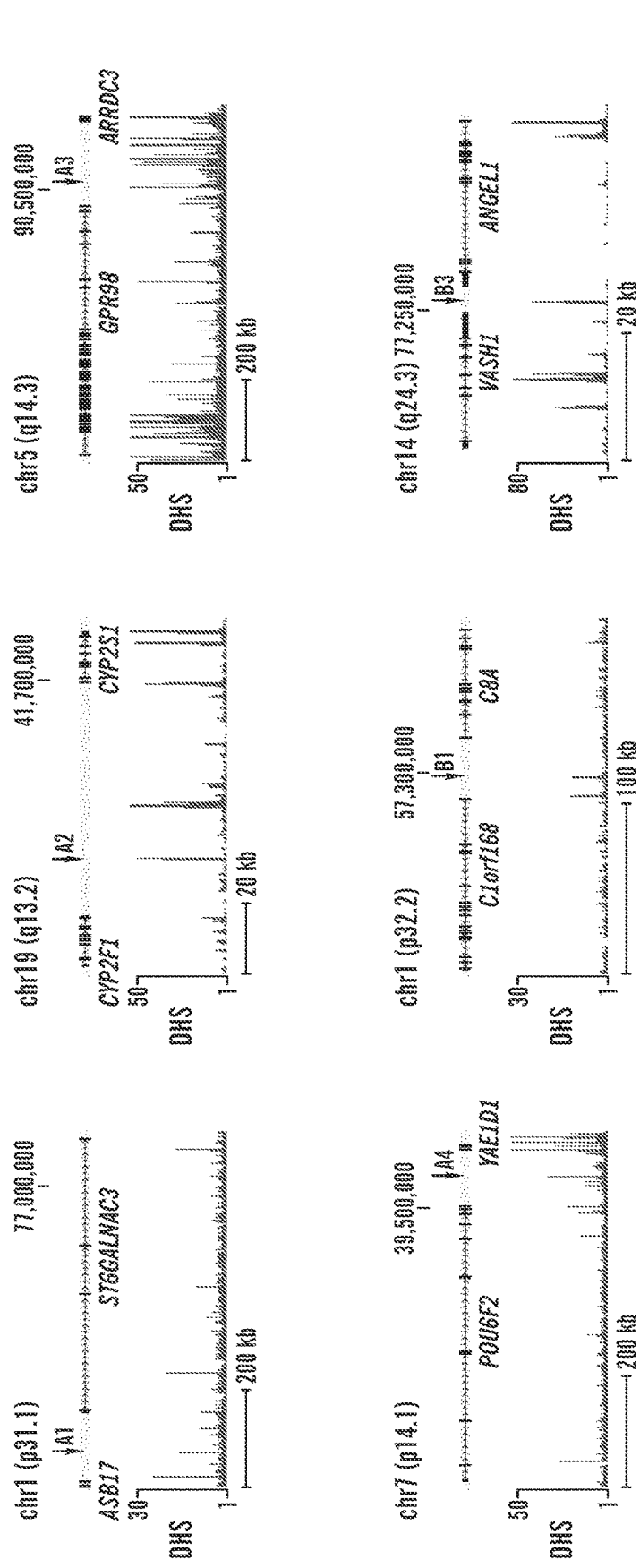
FIG. 8 Genomic organization of intergenic insulators. The upper graph of each panel shows the genomic organization of candidate insulators located between two genes. The chromosome numbers and hg19-based coordinates for each insulator are provided at the top, while the locations of the insulators relative to the surrounding genes are indicated by arrows adjacent to the insulator IDs. Also displayed are the genomic configurations of the flanking genes with the gene symbols listed below. The lower graph of each panel shows the DNase I hypersensitivity profiles across the corresponding genomic regions based on DNase I-seq studies in K562 cells.
Figure 8:
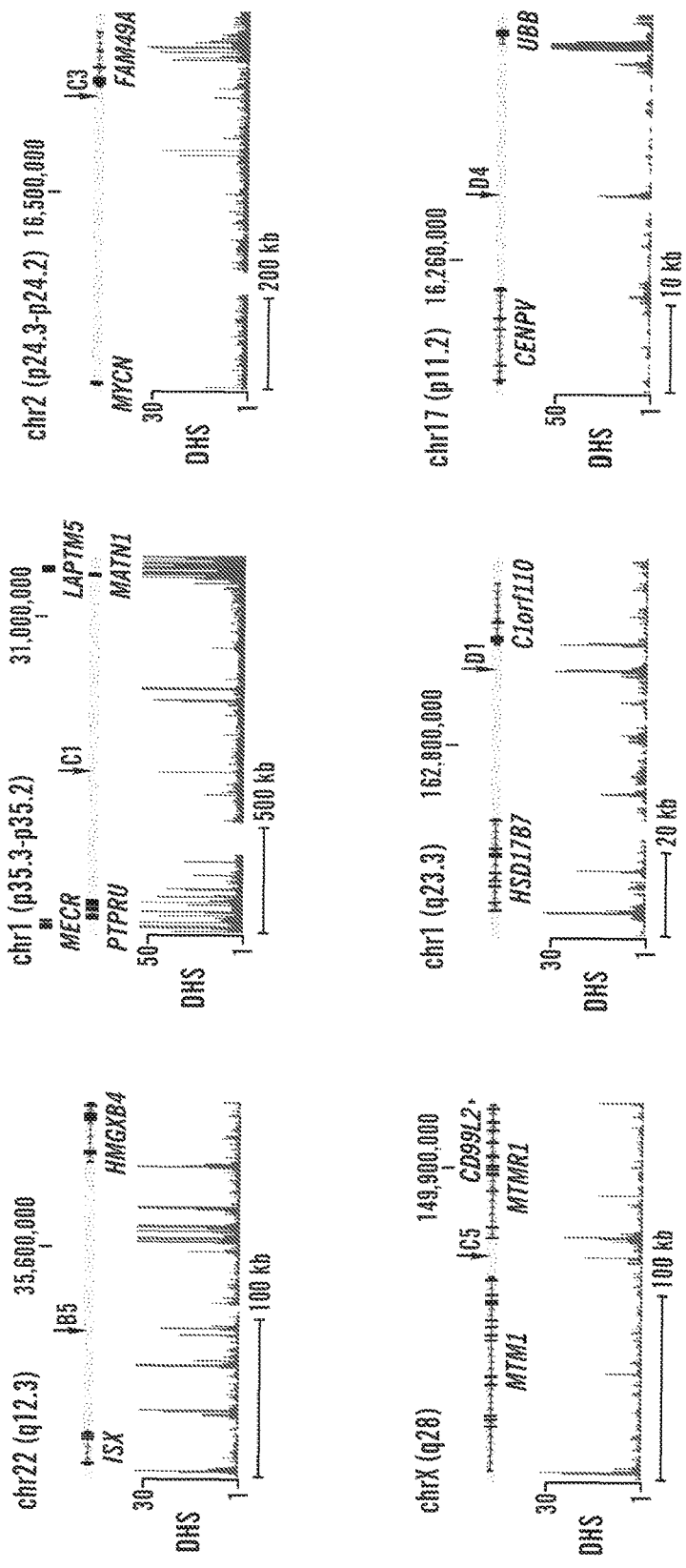
Figure 8:
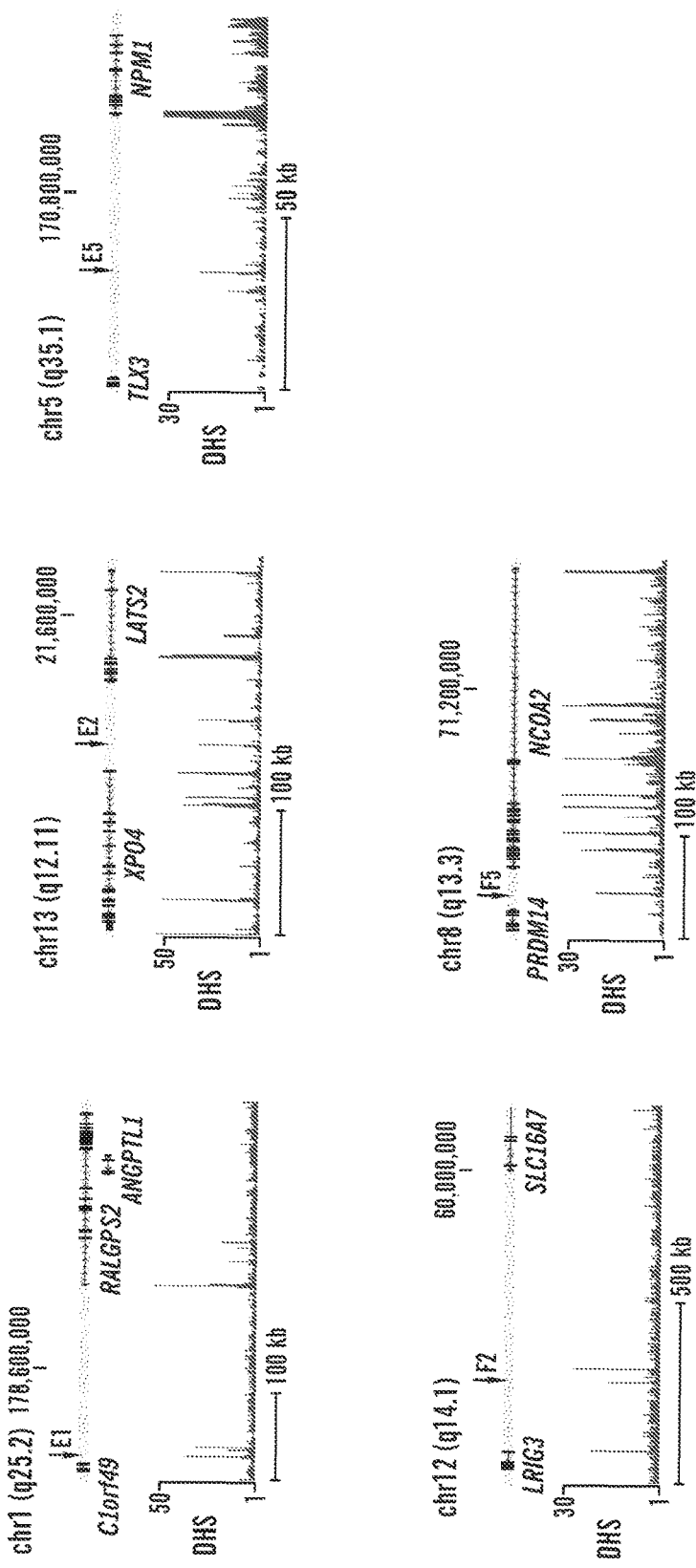
Figure 9:
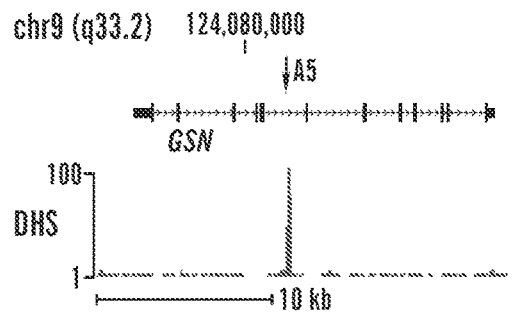
FIG. 9 Genomic organization of intragenic insulators. The upper graph of each panel shows the genomic organization of candidate insulators located within gene bodies. The chromosome numbers and hg19-based coordinates for each insulator are provided at the top, while the locations of the insulators relative to the specific genes are indicated by arrows adjacent to the insulator IDs. Also displayed are the genomic configurations of the specific genes with the gene symbols listed below. The lower graph of each panel shows the DNase I hypersensitivity profiles across the corresponding genomic regions based on DNase I-seq studies in K562 cells.
Figure 9:
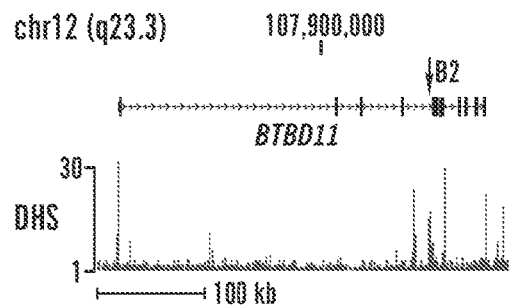
Figure 9:
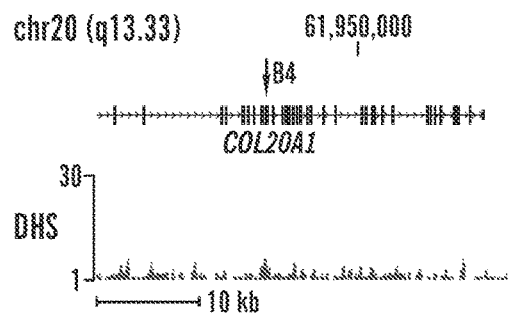
Figure 9:
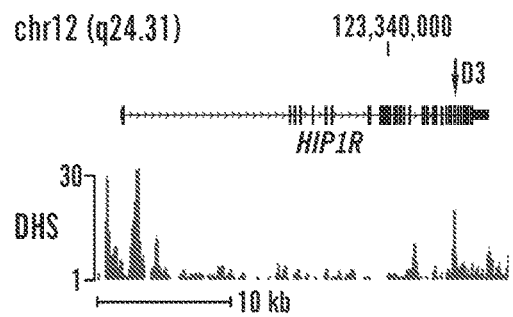
Figure 9:
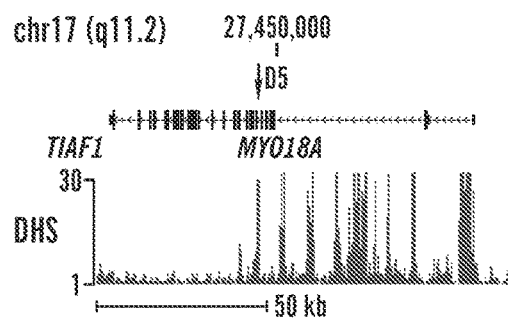
Figure 9:
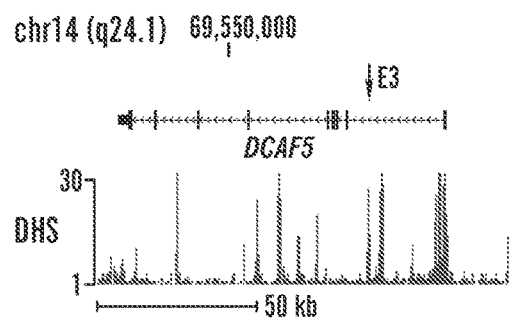
Figure 9:
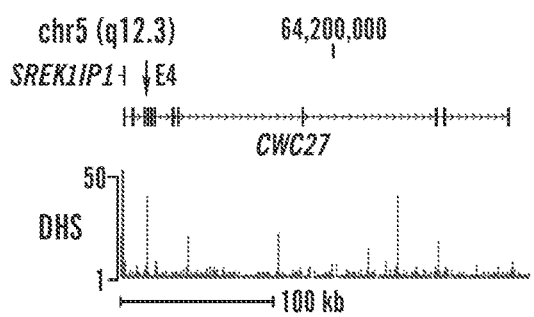
Figure 9:
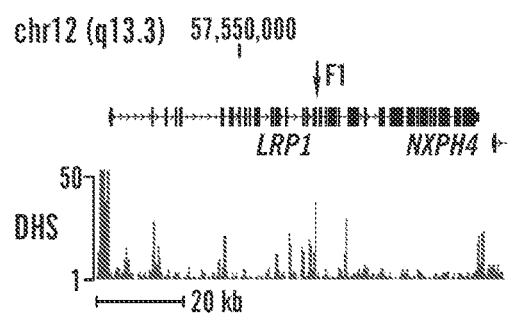
Figure 9:
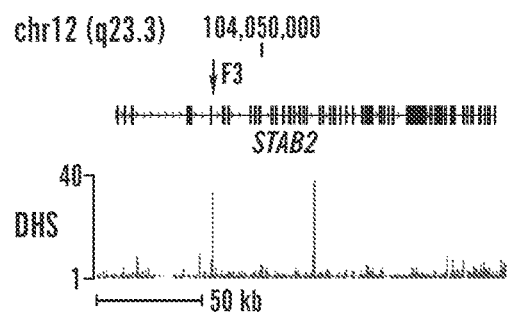
Figure 9:
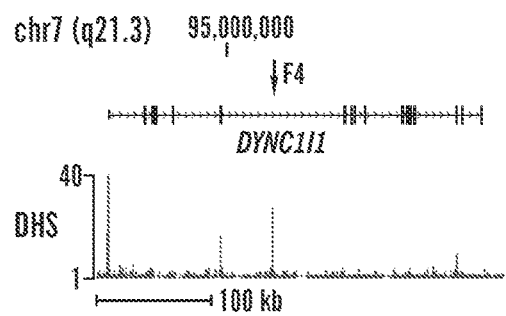

Of the 30 potential insulators selected from classes A to F, 27 were successfully cloned and analyzed in the enhancer-blocking assay; 17 sequences were located intergenically and ten in introns (FIGS. 8 and 9). All exhibited enhancer-blocking activity (FIG. 2B and Table 2). Twenty of the 27 displayed enhancer-blocking activity that was superior to that of cHS4 (FIG. 2C). The enhancer-blocking activity of element A2 was 10-fold stronger than cHS4 while fifteen other elements displayed from two- to seven-fold stronger enhancer-blocking activity compared to cHS4 (FIG. 2C). These results showed that the genomic approach described herein identified enhancer-blocking insulators with 100% accuracy among the high occupancy CTCF sites.

Figure 3A:
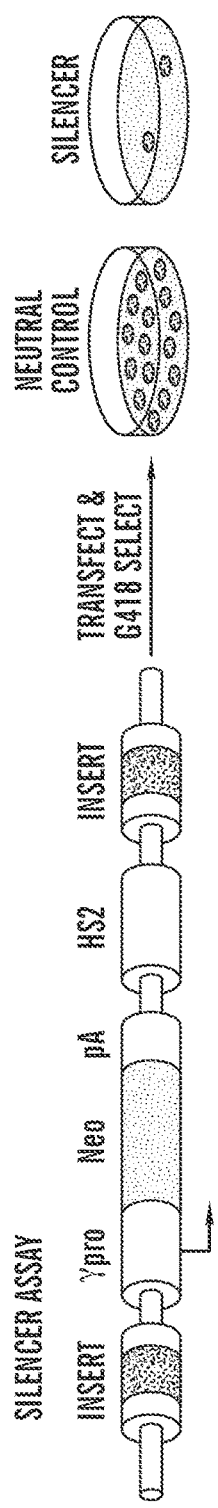
FIGS. 3A-3D Assessing the enhancer-blocking insulators for silencer activity and effects on lentiviral vector titers.
Figure 3B:
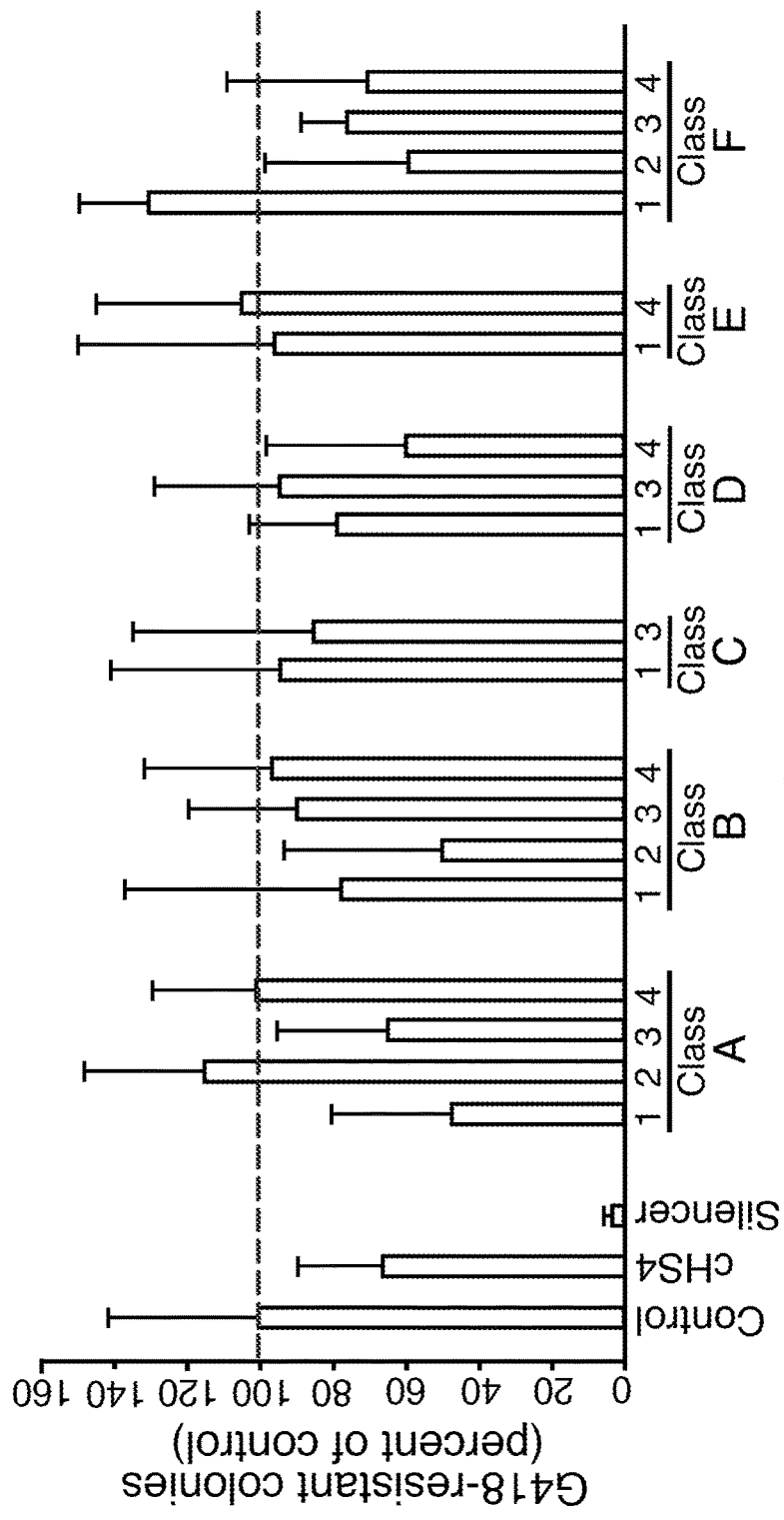

To exclude the possibility that these elements were silencers rather than enhancer-blocking insulators, the inventors used a silencer assay in which the element under study is placed outside the enhancer-promoter cassette. Silencers are expected to suppress promoter activity or inhibit the formation of the enhancer/promoter complex thus resulting in decreased neo expression and decreased colony numbers (FIG. 3A). Silencer assays were performed using 19 elements with enhancer-blocking activities equal to or higher than cHS4 (FIG. 3B and Table 4). The positive silencer control in these assays decreased colony formation 23-fold, while in no cases were colony numbers statistically different from the negative control, indicating that none of the 19 elements carried silencer activity.

TABLE 4

Testing insulator elements for silencer activity.

| Insulator | Colony Yields[a] Mean ± s.d. |
|---|---|
| Control | 1.000 ± 0.411 |
| cHS4 | 0.657 ± 0.286 |
| Silencer T39 | 0.044 ± 0.020 |
| A1 | 0.474 ± 0.326 |

TABLE 4-continued

Testing insulator elements for silencer activity.

| Insulator | Colony Yields[a] Mean ± s.d. |
|---|---|
| A2 | 1.154 ± 0.329 |
| A3 | 0.649 ± 0.301 |
| A4 | 1.009 ± 0.283 |
| B1 | 0.773 ± 0.593 |
| B2 | 0.505 ± 0.435 |
| B3 | 0.896 ± 0.293 |
| B4 | 0.972 ± 0.354 |
| C1 | 0.947 ± 0.461 |
| C3 | 0.856 ± 0.497 |
| D1 | 0.792 ± 0.238 |
| D3 | 0.942 ± 0.340 |
| D4 | 0.602 ± 0.387 |
| E1 | 0.964 ± 0.534 |
| E4 | 1.052 ± 0.398 |
| F1 | 1.305 ± 0.193 |
| F2 | 0.588 ± 0.390 |
| F3 | 0.762 ± 0.149 |
| F4 | 0.700 ± 0.388 |

[a]Mean ± standard deviation compared to the neutral spacer control in the outside "silencer" position taken as 1 (100%). None of these values differed statistically from the control.

Only a Minority of the CTCF Sites are Insulators

Figure 2D:
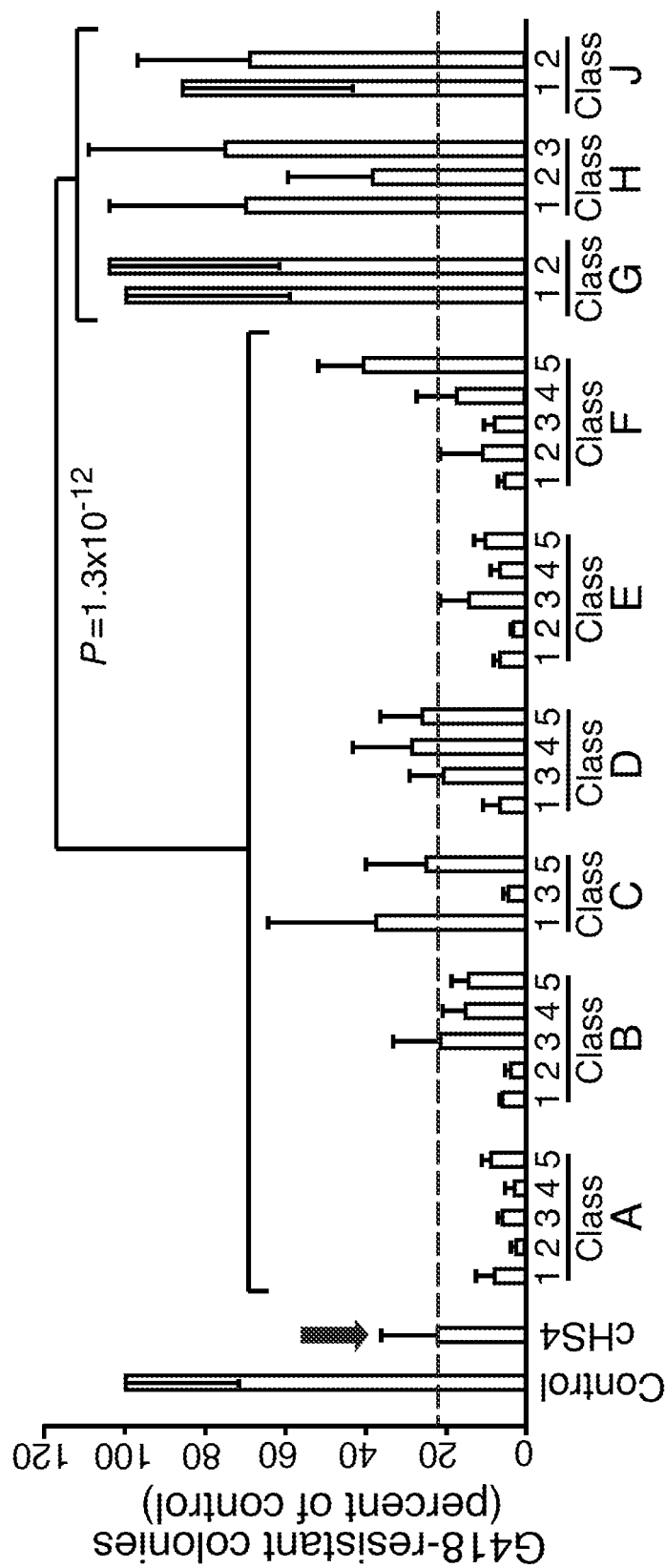

To further test the relationship between CTCF occupancy and enhancer-blocking function, seven elements from three low CTCF occupancy classes G, H, and J with CTCF occupancy 9.6%, 9.7% and 9.8% (Tables 1, 2, and 3) were used for enhancer-blocker assays. Only one displayed a moderate degree of enhancer-blocking activity, and decreased the number of colonies to 38.1% of the level of the un-insulated control (FIG. 2D). These results provide further evidence that it is both the structure of the CTCF motifs and the degree of CTCF occupancy that determine the function of a CTCF element as an enhancer blocker. Since the greatest majority of CTCF sites have low CTCF occupancy (data not shown), the inventors conclude that only a small minority of the CTCF sites of the human genome function as enhancer-blocking insulators.

Chromatin Context of Enhancer-blocking Insulators

Figure 10:
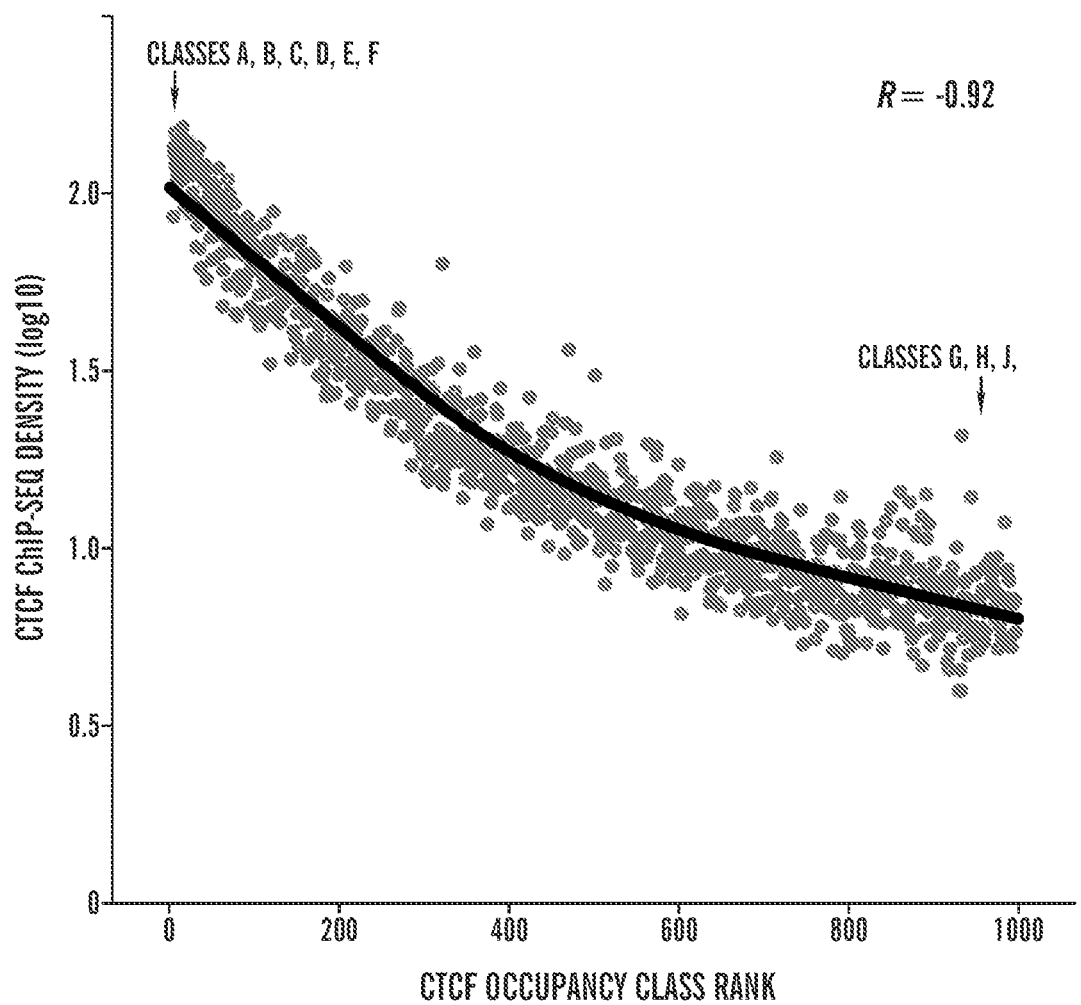
FIG. 10 Relationship between CTCF occupancy class and CTCF density. The average density of CTCF binding is shown for each CTCF occupancy class based on ChIP-seq studies in K562 cells (one data point for each of 1000 classes). The trend line represents LOESS fit. The locations of the high-occupancy classes A-F, and the low-occupancy classes G, H, and J are indicated by arrows. Note that the higher-occupancy insulators tend to exhibit a higher density of CTCF binding. R, Pearson correlation.
Figure 11:
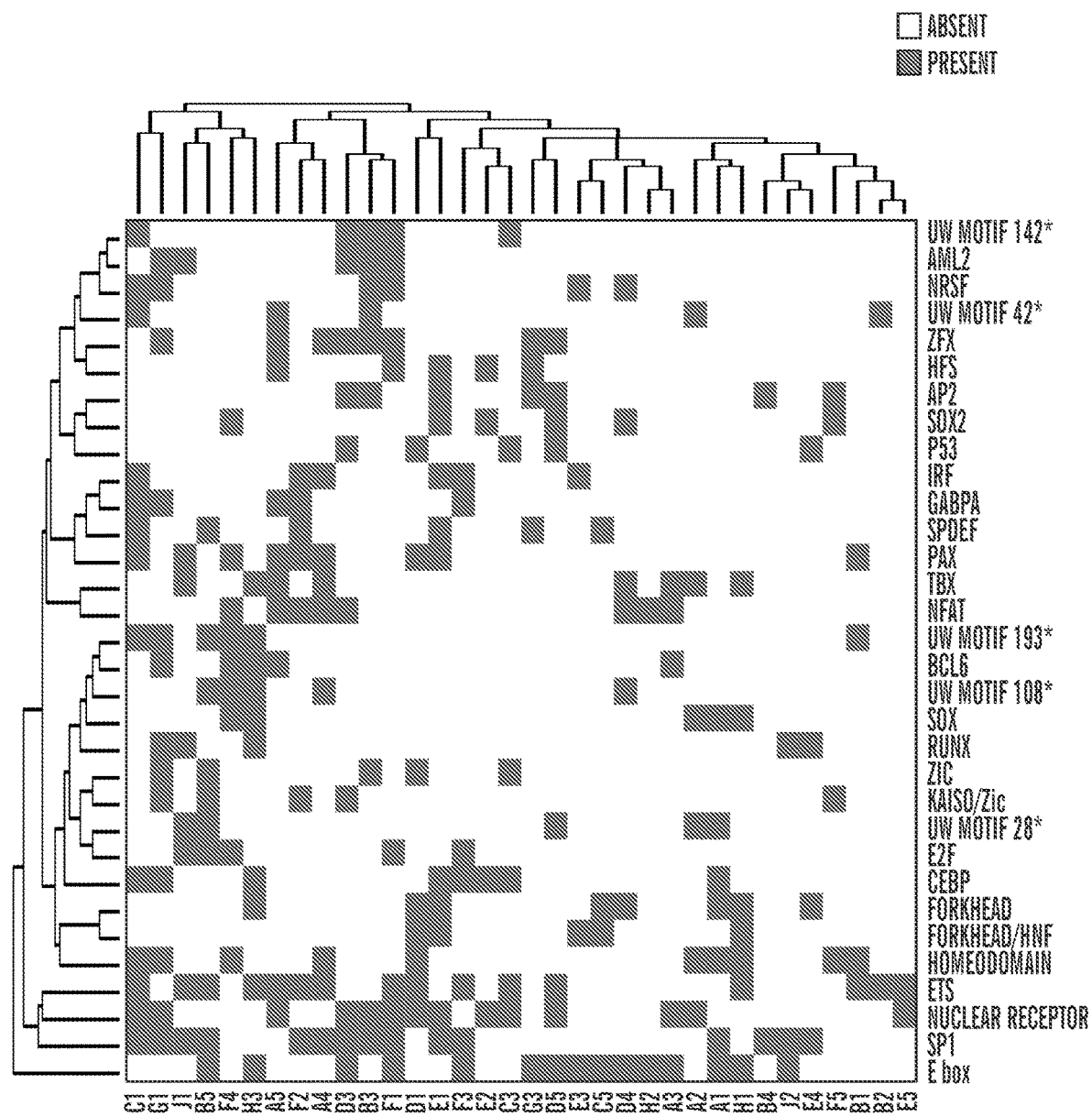
FIG. 11 Transcription factor recognition sequences associated with high occupancy insulator candidates. Potential sites of transcription factor binding were identified by scanning the sequences of candidate insulator elements cloned for functional studies (see Table 3) for recognition sequence matches with a threshold $P \leq 10^{-4}$ using the program FIMO (Grant et al. 2011). Position weight matrices were obtained from four major transcription factor binding motif collections: TRANSFAC (Matys et al. 2006); JASPAR (Portales-Casamar et al. 2010); UniPROBE (Newburger et al. 2009); and a published SELEX dataset (Jolma et al. 2013). Similar motifs were then clustered into families. Position weight matrices were also included that were derived de novo from genome-wide DNase I footprinting across 41 human cell types; only those not matching any other motifs were included (*) (Neph et al. 2012). Transcription factor recognition sequences were required to overlap a DNase I footprint by at least 3 bp in K562 cells with a footprint occupancy score less than 0.95 (i.e., stronger) (Neph et al. 2012) and were excluded if they overlapped a CTCF recognition sequence. Data are shown for transcription factor recognition sequences present in 5 or more elements. Presence of at least one recognition motif is indicated by gray, while absence of a recognition motif is indicated by white. Recognition sequences and insulator elements are ordered by hierarchical clustering. Note the absence of correlation between transcription factor recognition sequences and specific CTCF occupancy classes or potent insulator function.
Figure 12A:
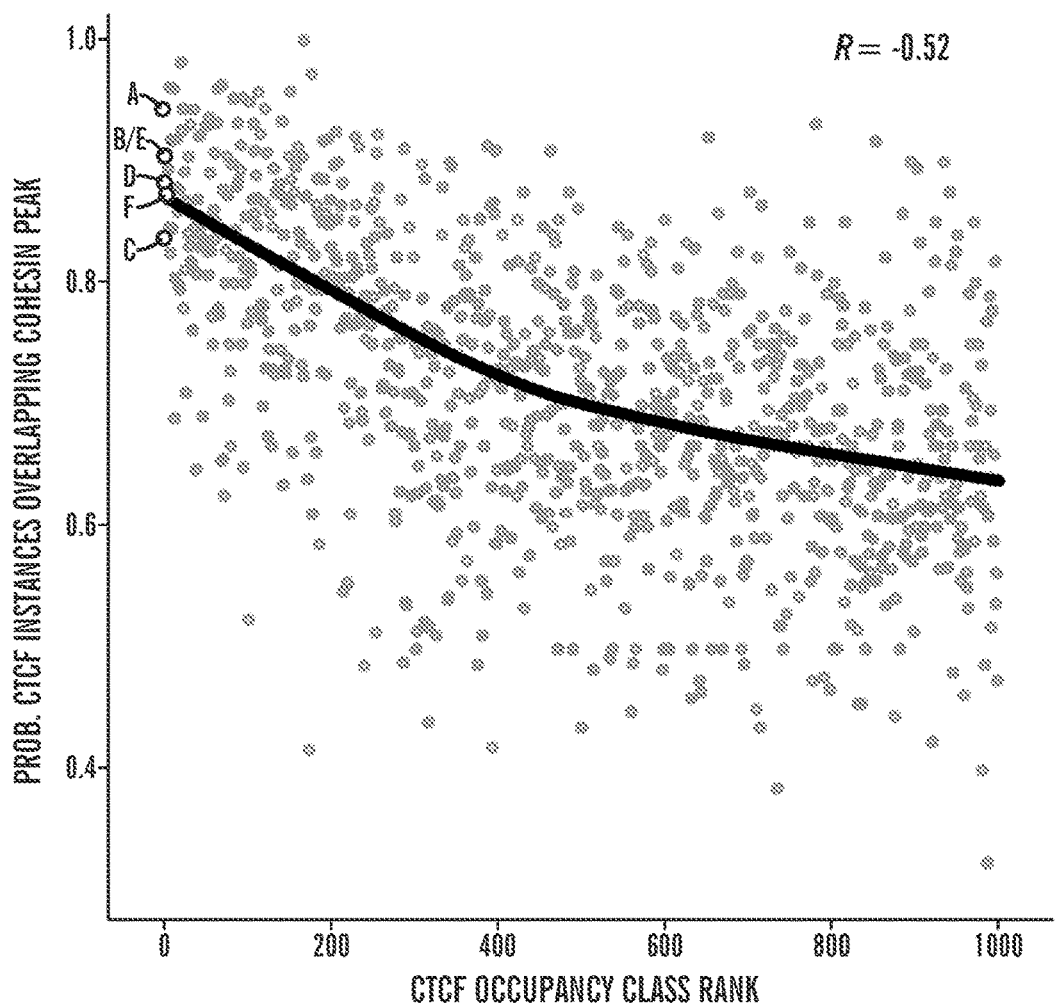
FIGS. 12A-12C Correlation between CTCF occupancy class and cohesin.
Figure 12B:
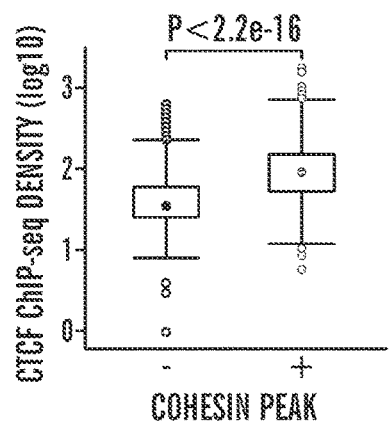
Figure 12C:
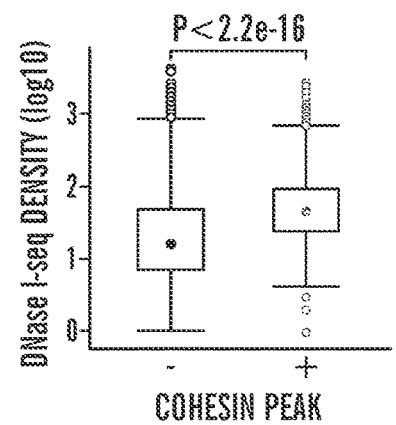
Figure 13A:
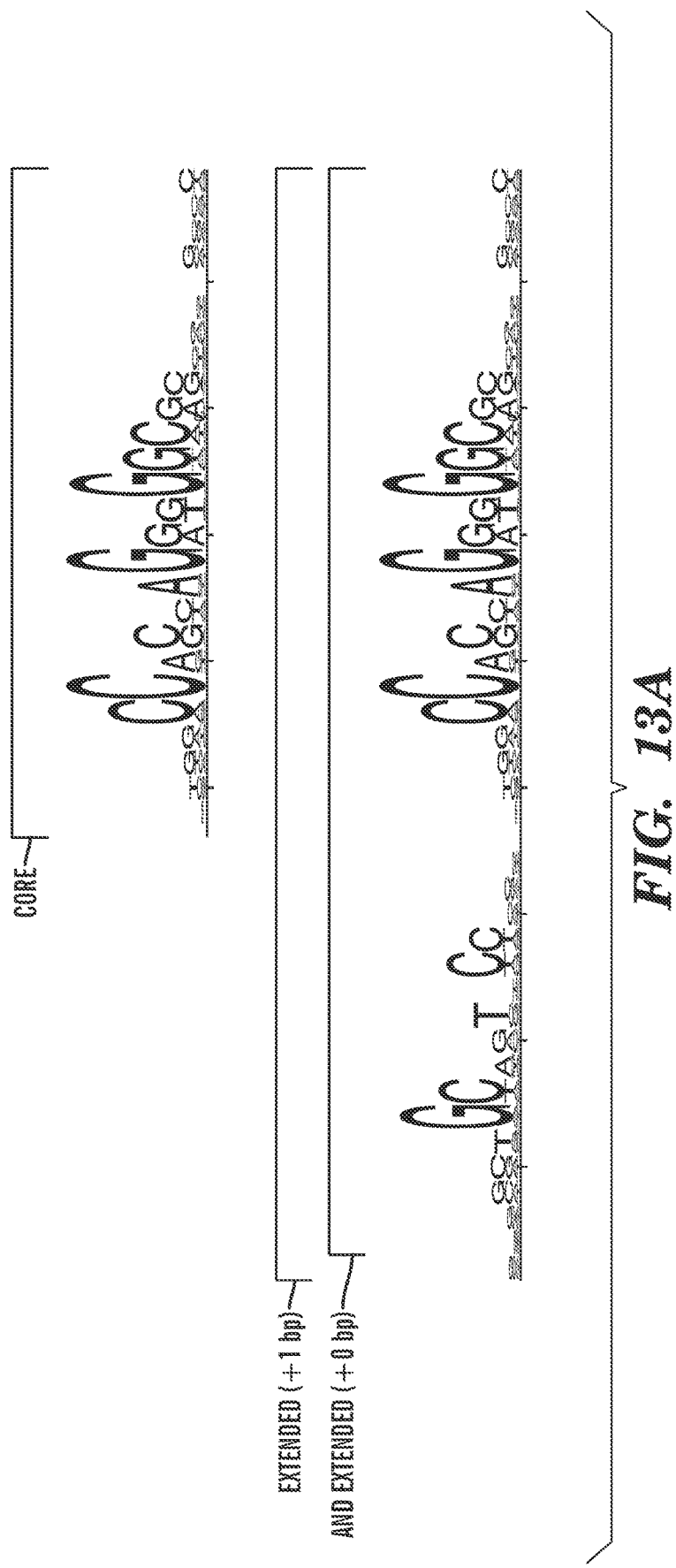
FIGS. 13A-13B Relationship between CTCF occupancy class and CTCF binding mode.
Figure 13B:
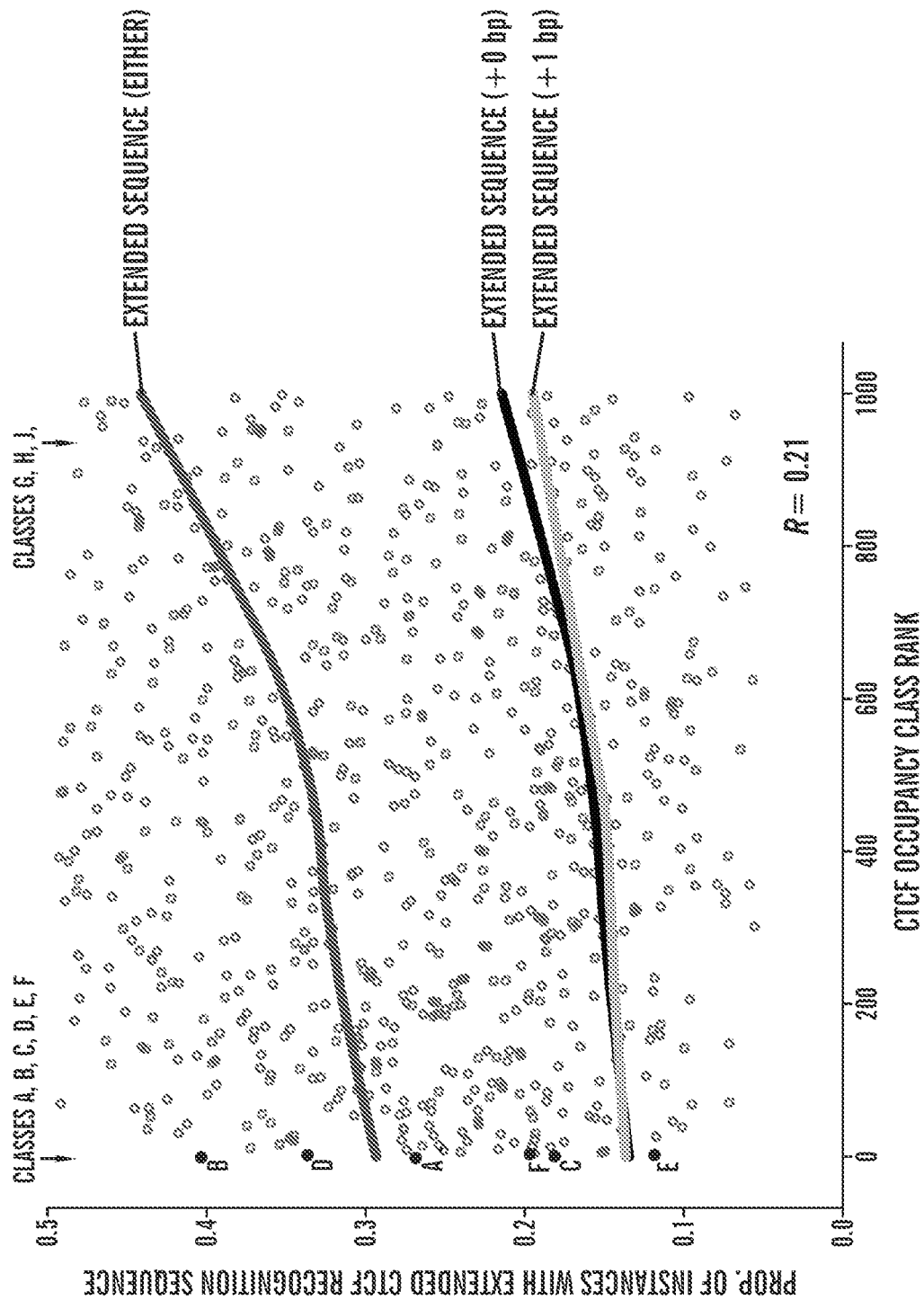
Figure 14A:
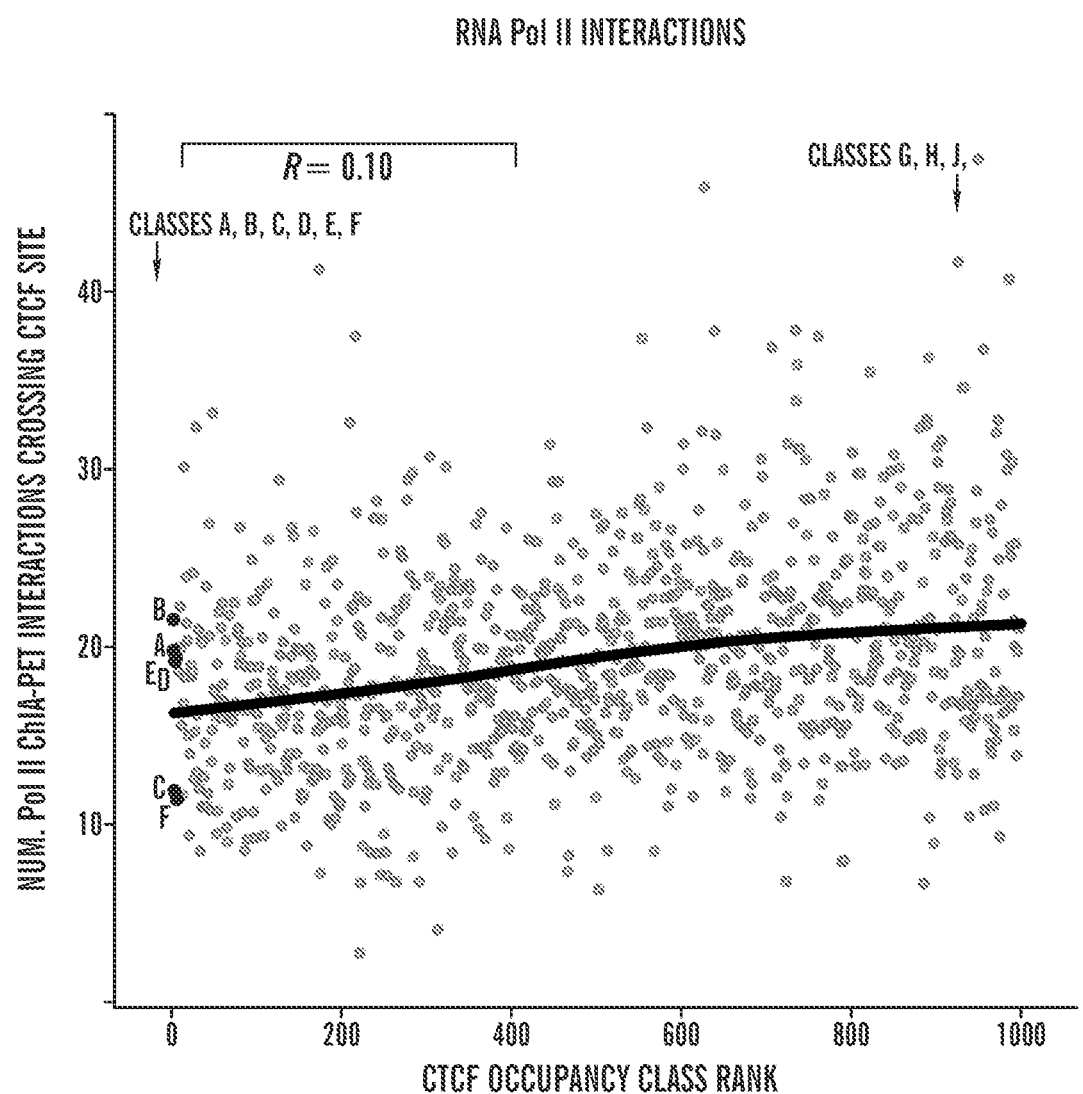
FIGS. 14A-14C Relation of CTCF occupancy class and long-range genomic interactions.
Figure 14B:
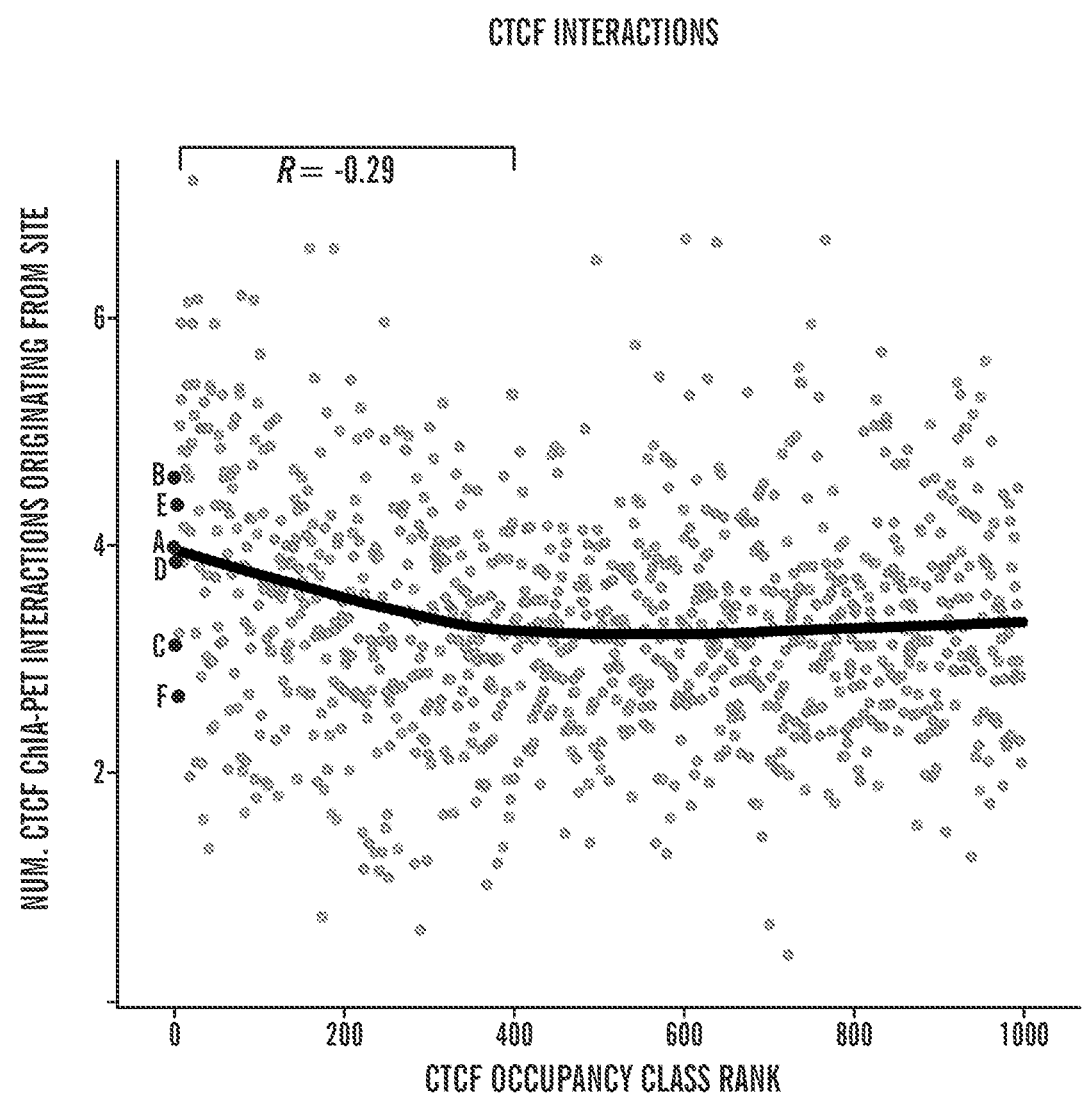
Figure 14C:
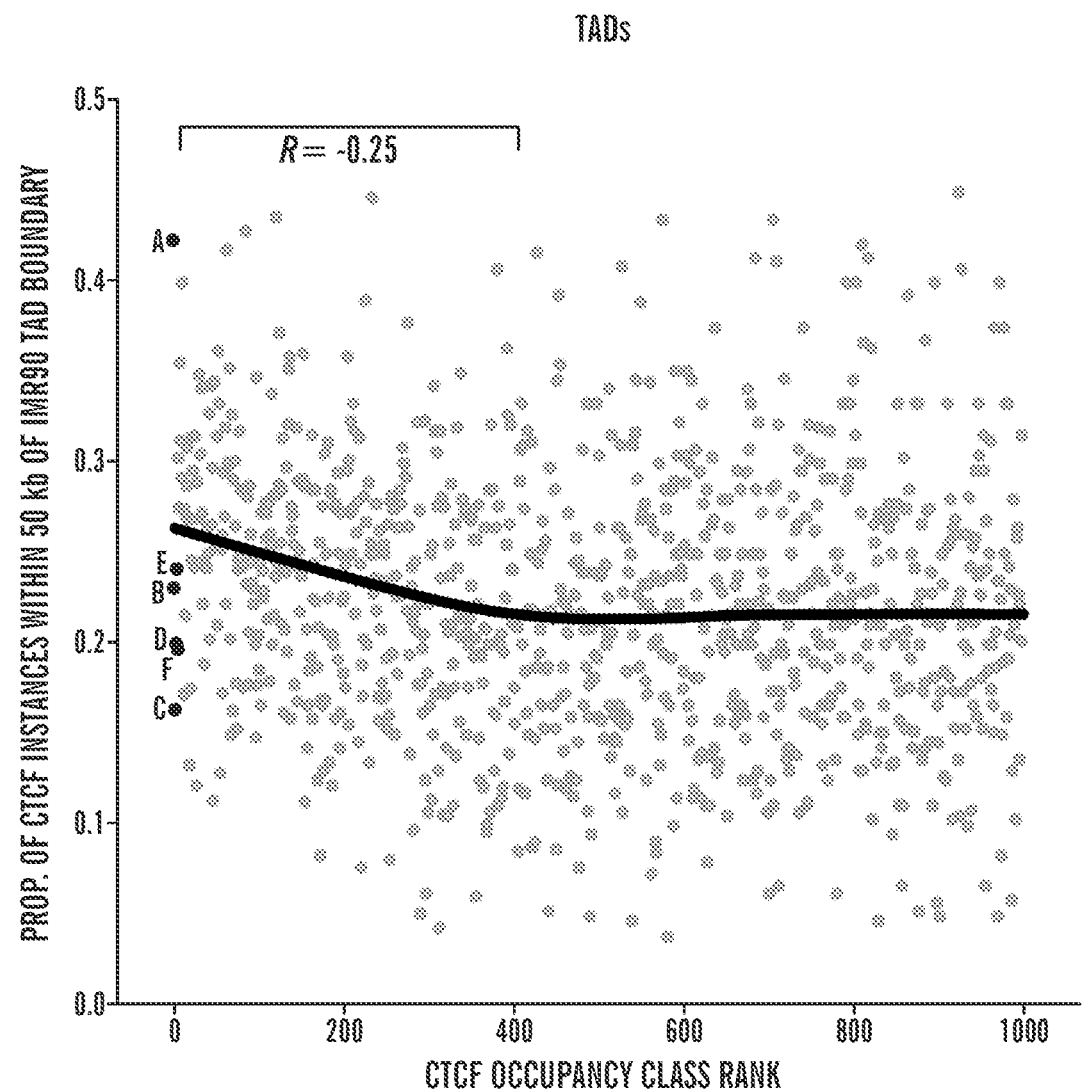
Figure 15:
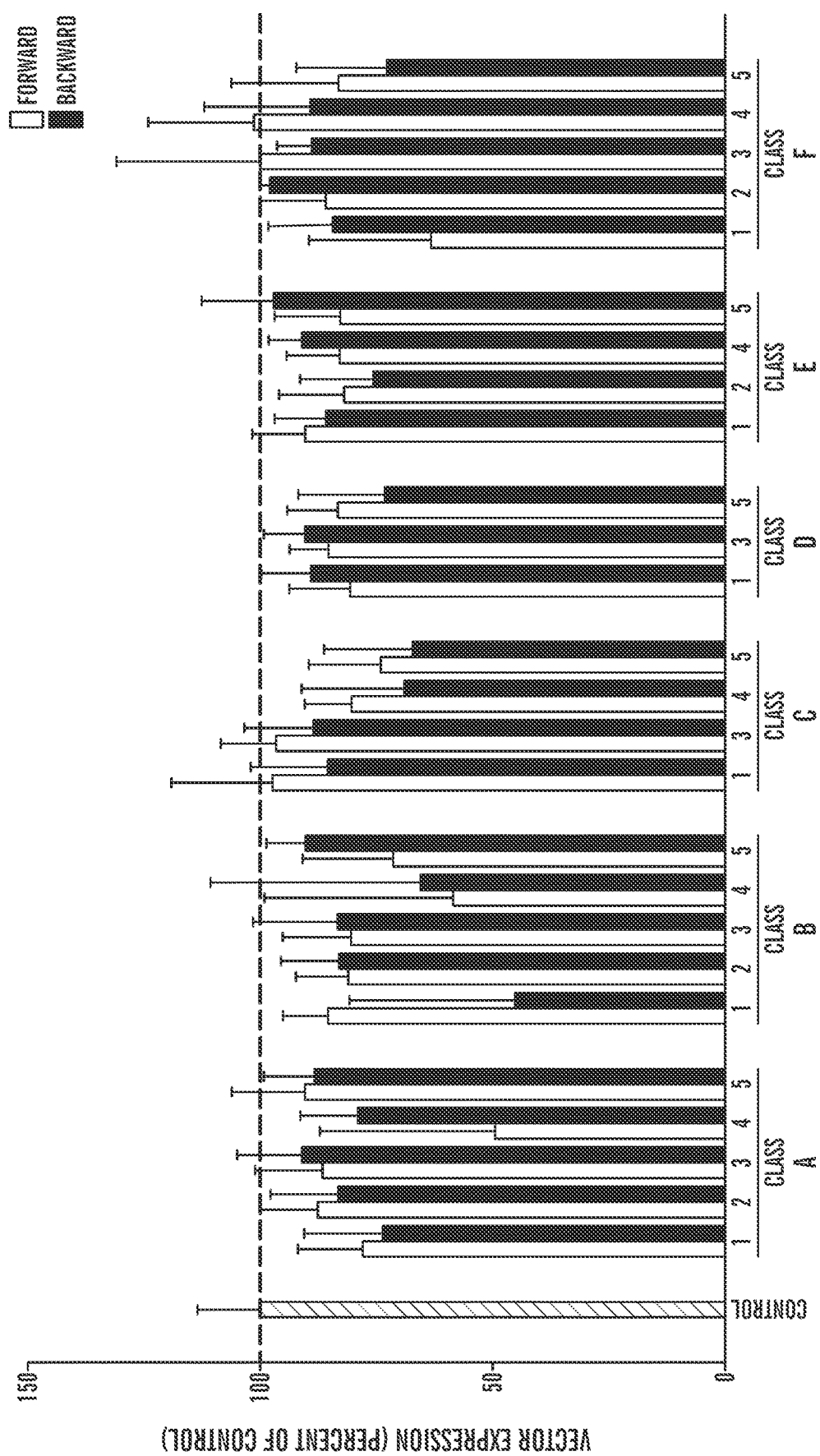
FIG. 15 Effects of insulators on GFP expression of lentiviral vectors. Insulator elements were inserted into the "double-copy" position of a lentiviral vector expressing GFP, and used to transduce human HT1080 cells. After 3 days, cultures were analyzed by flow cytometry to determine the amount of vector GFP expression in the GFP-positive cells. Cultures with low transduction rates (12.4±9.2 percent GFP-positive) were used to assure that most of the GFP-positive cells had one or a few vector copies. Expression data are shown as a percentage of the no-insert control. Histograms represent the mean±standard deviation from 4 independent experiments, and are reported as a percentage of the expression (mean fluorescent units of the GFP-positive cells) determined of the no-insert control (set at 100%). No samples were statistically different from the control after Bonferroni correction for multiple testing.

There are considerable differences in the degree of enhancer-blocking activities between the insulator elements of FIG. 2D, both among elements belonging to the same classes and across different classes. This variation cannot likely be attributed to differences in CTCF occupancy class because occupancy in classes A to F ranges from 100% to 98.6%. Variation in enhancer-blocking activity is also characteristic of elements belonging to the same class (compare elements D1 to D4 or F1 to F5 in FIG. 2D). The CTCF occupancy class is directly correlated with the density of CTCF binding (FIG. 10). Elements of the same class contain the same 14 bp CTCF core sequence but may exhibit additional functional properties conferred by the 100-200 bp flanking sequence included in the fragments cloned for the functional assays (Table 3). Indeed, the fragments used to assess the insulator activity of the high- and low-occupancy class CTCF sites also include several other transcription factor recognition sequences in DNase I footprints in K562 cells, notably including E box, Sp1, and nuclear hormone receptor sequences (FIG. 11). However, the inventors did not observe a direct correlation between any specific transcription factor recognition sequence or pattern of sequences and either a specific CTCF occupancy rank or insulator activity level. The inventors did note a direct correlation between CTCF occupancy and overlap with binding of Rad21 (FIG. 12A), a subunit of cohesin that is thought to play an important role in insulator function (28). Overlap with cohesin was also correlated with increased CTCF binding and accessibility to DNase I (FIG. 12B, 12C). It has been suggested that the multivalent nature of CTCF permits regulation of binding site function by differential recruitment of zinc fingers to a combination of core and upstream sequences (29, 30). It was found that the high-occupancy CTCF classes preferentially lack the extended recognition sequence, potentially freeing zinc fingers 8-11 for interaction with other proteins or DNA sequence (FIG. 13). Based on published chromatin interaction analysis data, the inventors noted a slight depletion of Pol II interactions crossing the high-occupancy CTCF sites (31), and a small correlation between the high-occupancy CTCF sites and both interactions with other CTCF sites and associations with topologically associated domains (TADs) (19) (FIG. 14). These latter findings are consistent with models for enhancer-blocking insulators, but do not point to a specific chromatin context that can help identify highly efficient chromatin insulators better than the CTCF occupancy class.

The New Insulators do not Affect Viral Vector Stability

Figure 3C:
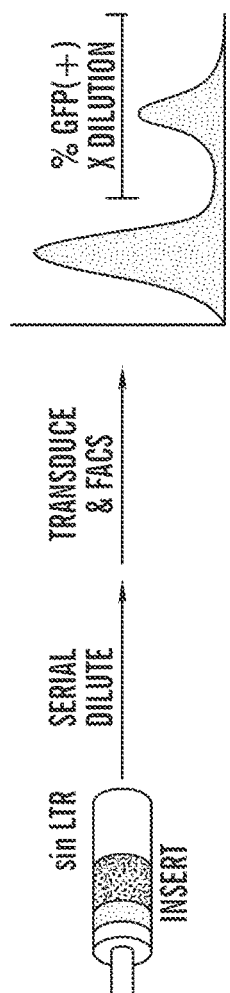
Figure 3D:
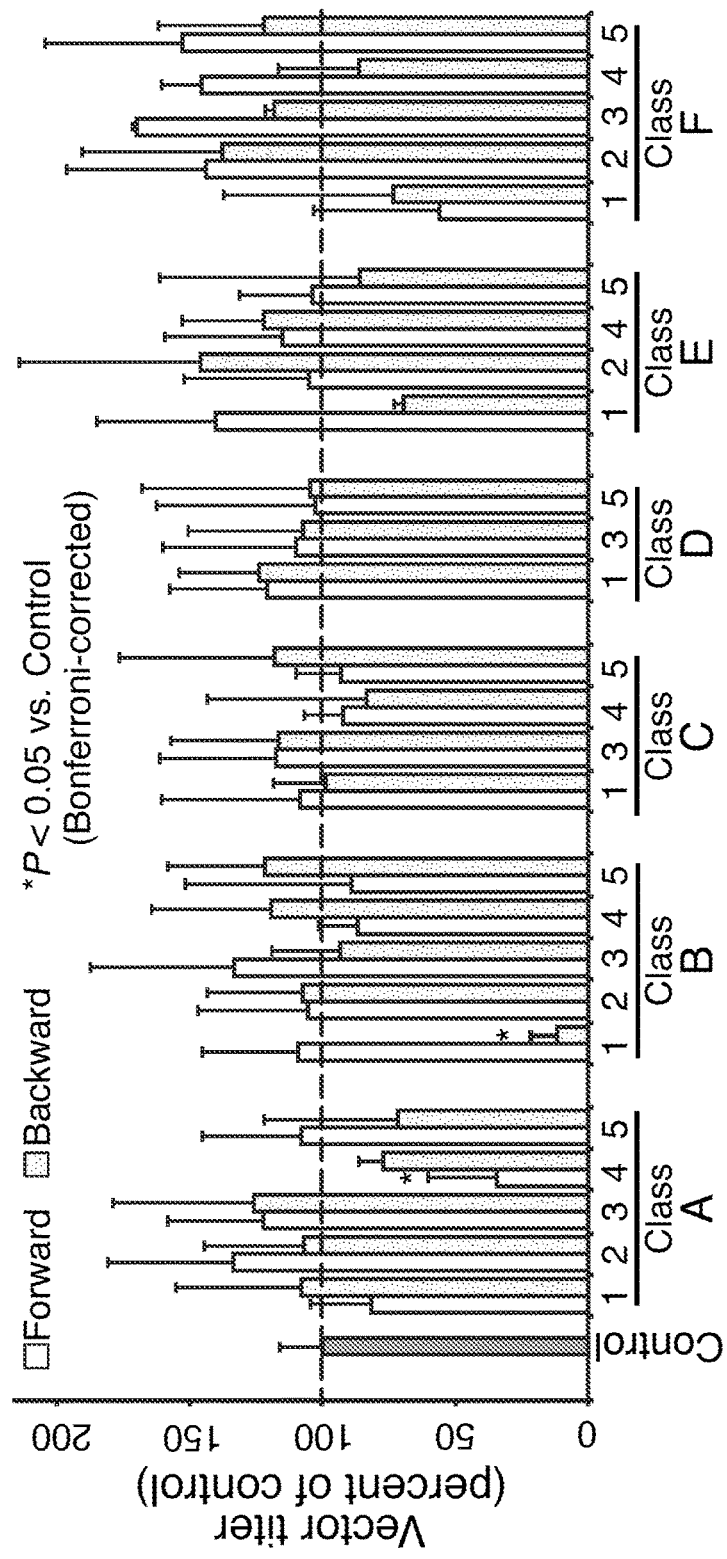
Figure 16:
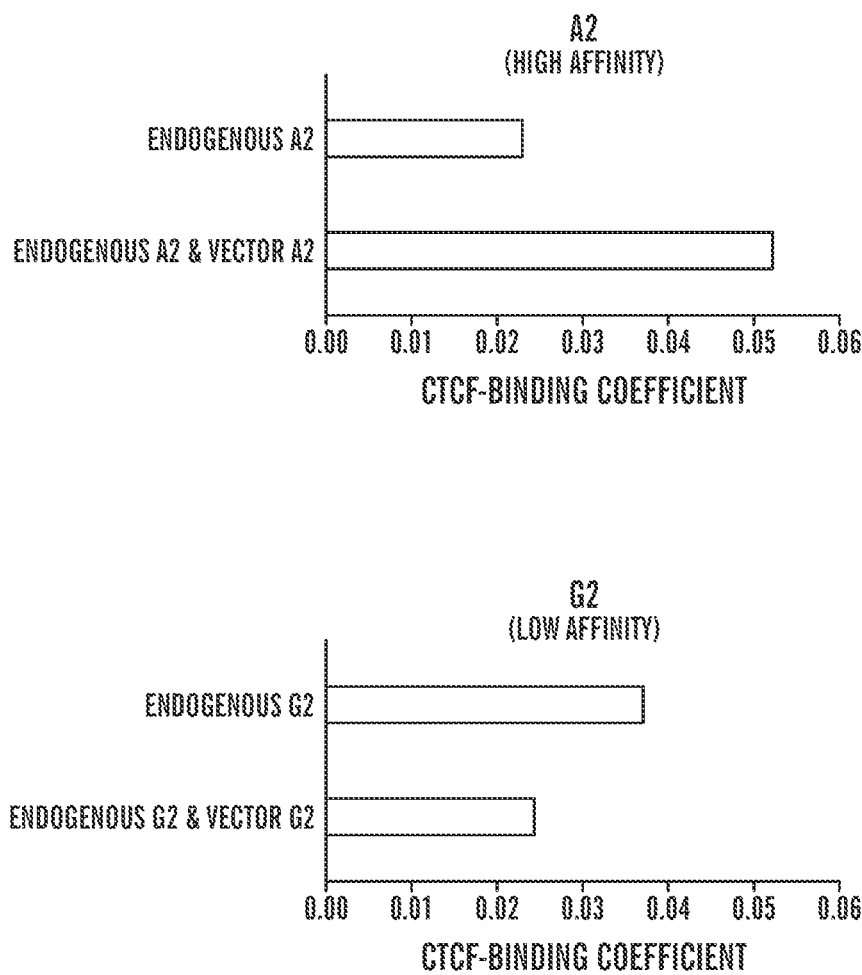
FIG. 16 Capacity of insulator elements to bind CTCF in the context of lentiviral vectors. Insulator candidates A2 (high-affinity) and G2 (low affinity) were inserted into the long-terminal repeats of a lentiviral reporter vector using the double-copy arrangement. K562 cells were transduced with the resulting vectors at a low multiplicity of infection (5% GFP(+) cells) in order to target only one vector provirus per cell, and a pool of transduced cells were selected by cell sorting for GFP. The resulting pools (~98% GFP(+), approximately one vector provirus per cell) were then analyzed by conventional chromatin immunoprecipitation (ChIP) for CTCF binding at A2 or G2. The CTCF-binding coefficient k was calculated as follows: k=[x1/x2]2^[Ctin−Ctch], where x1 is the DNA amount for the input sample, x2 is the DNA amount used for the generation of the ChIP product, Ctin is the threshold cycle for the input DNA, and Ctch is the threshold cycle for the ChIP DNA. In these studies, the ratio of x1/x2 was set to be the same for the vector-transduced and control cells so that the CTCF-binding coefficient can be estimated by k=2^[Ctin−Ctch]. Ct values were averaged from duplicate determinations. Data are presented for CTCF binding at the endogenous loci alone (using K562 cells not transduced with the specific candidate) compared to the sum of binding at both the endogenous loci plus the loci transferred with the lentiviral vector. Note that high-affinity insulator candidate A2 appears to bind CTCF more efficiently in the context of the lentiviral vector than in the context of its native locus, while low-affinity insulator candidate G2 appears to bind CTCF less efficiently in the context of the lentiviral vector than in the context of its native locus.

To assess the effects of these insulator elements on vector titers, the inventors introduced each insulator into the double-copy region of a third-generation lentiviral vector expressing GFP from a constitutive Pgk promoter and measured viral titers and GFP expression (FIG. 3C). Only two of the 26 insulators tested significantly affected the vector titers either in the forward or in the reverse orientation (FIG. 3D, Table 5). None of the elements affected adversely vector GFP expression (FIG. 16 and Table 6). In addition, chromatin immunoprecipitation studies demonstrated the ability of a high-occupancy class insulator to efficiently bind CTCF in this lentiviral vector context in K562 cells (FIG. 16). Considering orientation then, greater than 95% (50 out of 52) of the high efficiency insulators tested had little or no negative effect on viral titers. Where biological systems are widely regarded as unpredictable, this is a surprisingly high degree of predictability. For clinical use, one would typically confirm minimal effect on viral titer and efficiency as an insulator for any given element as described herein.

TABLE 5

Effects of insulator elements on lentiviral vector titers.

| | Lentiviral Vector Titer [a,b] | |
|---|---|---|
| Insulator | Forward [c] Mean ± s.d. | Reverse [c] Mean ± s.d. |
| Control | 1.000 ± 0.161 | |
| A1 | 0.817 ± 0.227 | 1.080 ± 0.472 |
| A2 | 1.335 ± 0.472 | 1.071 ± 0.371 |
| A3 | 1.223 ± 0.364 | 1.258 ± 0.533 |
| A4 | * 0.343 ± 0.258 | 0.772 ± 0.090 |
| A5 | 1.080 ± 0.373 | 0.717 ± 0.503 |
| B1 | 1.092 ± 0.358 | * 0.116 ± 0.100 |
| B2 | 1.055 ± 0.414 | 1.075 ± 0.359 |
| B3 | 1.333 ± 0.544 | 0.934 ± 0.257 |
| B4 | 0.868 ± 0.150 | 1.193 ± 0.450 |
| B5 | 0.891 ± 0.629 | 1.217 ± 0.367 |
| C1 | 1.085 ± 0.525 | 0.989 ± 0.193 |
| C3 | 1.175 ± 0.438 | 1.165 ± 0.409 |
| C4 | 0.923 ± 0.149 | 0.835 ± 0.600 |
| C5 | 0.931 ± 0.167 | 1.181 ± 0.587 |
| D1 | 1.209 ± 0.372 | 1.239 ± 0.301 |
| D3 | 1.100 ± 0.505 | 1.074 ± 0.434 |
| D5 | 1.027 ± 0.602 | 1.047 ± 0.636 |
| E1 | 1.402 ± 0.448 | 0.696 ± 0.034 |
| E2 | 1.051 ± 0.474 | 1.459 ± 0.685 |
| E4 | 1.151 ± 0.447 | 1.221 ± 0.308 |
| E5 | 1.038 ± 0.272 | 0.860 ± 0.755 |

TABLE 5-continued

Effects of insulator elements on lentiviral vector titers.

| Insulator | Lentiviral Vector Titer [a,b] | |
|---|---|---|
| | Forward [c] Mean ± s.d. | Reverse [c] Mean ± s.d. |
| F1 | 0.561 ± 0.471 | 0.734 ± 0.639 |
| F2 | 1.438 ± 0.530 | 1.377 ± 0.528 |
| F3 | 1.701 ± 0.019 | 1.182 ± 0.032 |
| F4 | 1.455 ± 0.152 | 0.863 ± 0.302 |
| F5 | 1.529 ± 0.513 | 1.221 ± 0.399 |

[a] Means ± standard deviation compared to uninsulated lentiviral vector taken as 1 (100%).
[b] Titers based on % of GFP(+) cells transduced with titrated vector.
[c] All values are not statistically different from control except where indicated by an asterisk.

TABLE 6

Effects of the novel insulator elements on lentiviral vector expression.

| Insulator | Lentiviral Vector Expression (a, b) | |
|---|---|---|
| | Forward [c] Mean ± s.d. | Reverse [c] Mean ± s.d. |
| Control | 1.000 ± 0.134 | |
| A1 | 0.780 ± 0.140 | 0.734 ± 0.171 |
| A2 | 0.875 ± 0.113 | 0.833 ± 0.145 |
| A3 | 0.866 ± 0.145 | 0.910 ± 0.143 |
| A4 | 0.494 ± 0.378 | 0.790 ± 0.127 |
| A5 | 0.905 ± 0.155 | 0.883 ± 0.108 |
| B1 | 0.853 ± 0.099 | 0.452 ± 0.358 |
| B2 | 0.811 ± 0.112 | 0.830 ± 0.127 |
| B3 | 0.804 ± 0.148 | 0.834 ± 0.182 |
| B4 | 0.585 ± 0.410 | 0.654 ± 0.453 |
| B5 | 0.713 ± 0.196 | 0.903 ± 0.085 |
| C1 | 0.974 ± 0.219 | 0.855 ± 0.167 |
| C3 | 0.966 ± 0.118 | 0.884 ± 0.151 |
| C4 | 0.803 ± 0.103 | 0.689 ± 0.219 |
| C5 | 0.742 ± 0.153 | 0.673 ± 0.190 |
| D1 | 0.808 ± 0.128 | 0.891 ± 0.118 |
| D3 | 0.855 ± 0.082 | 0.905 ± 0.088 |
| D5 | 0.834 ± 0.109 | 0.731 ± 0.188 |
| E1 | 0.902 ± 0.113 | 0.859 ± 0.113 |
| E2 | 0.820 ± 0.141 | 0.757 ± 0.156 |
| E4 | 0.829 ± 0.117 | 0.910 ± 0.073 |
| E5 | 0.830 ± 0.141 | 0.971 ± 0.154 |
| F1 | 0.633 ± 0.261 | 0.844 ± 0.142 |
| F2 | 0.860 ± 0.149 | 0.979 ± 0.021 |
| F3 | 1.002 ± 0.307 | 0.889 ± 0.077 |
| F4 | 1.013 ± 0.227 | 0.893 ± 0.231 |
| F5 | 0.832 ± 0.234 | 0.726 ± 0.198 |

(a) Means ± standard deviation compared to uninsulated lentiviral vector taken as 1 (100%).
(b) Expression based on mean fluorescence of GFP(+) cells transduced with titrated vector.
[c] All values are not statistically different from control.

Reduction of Vector-Mediated Genotoxicity

Figure 4A:
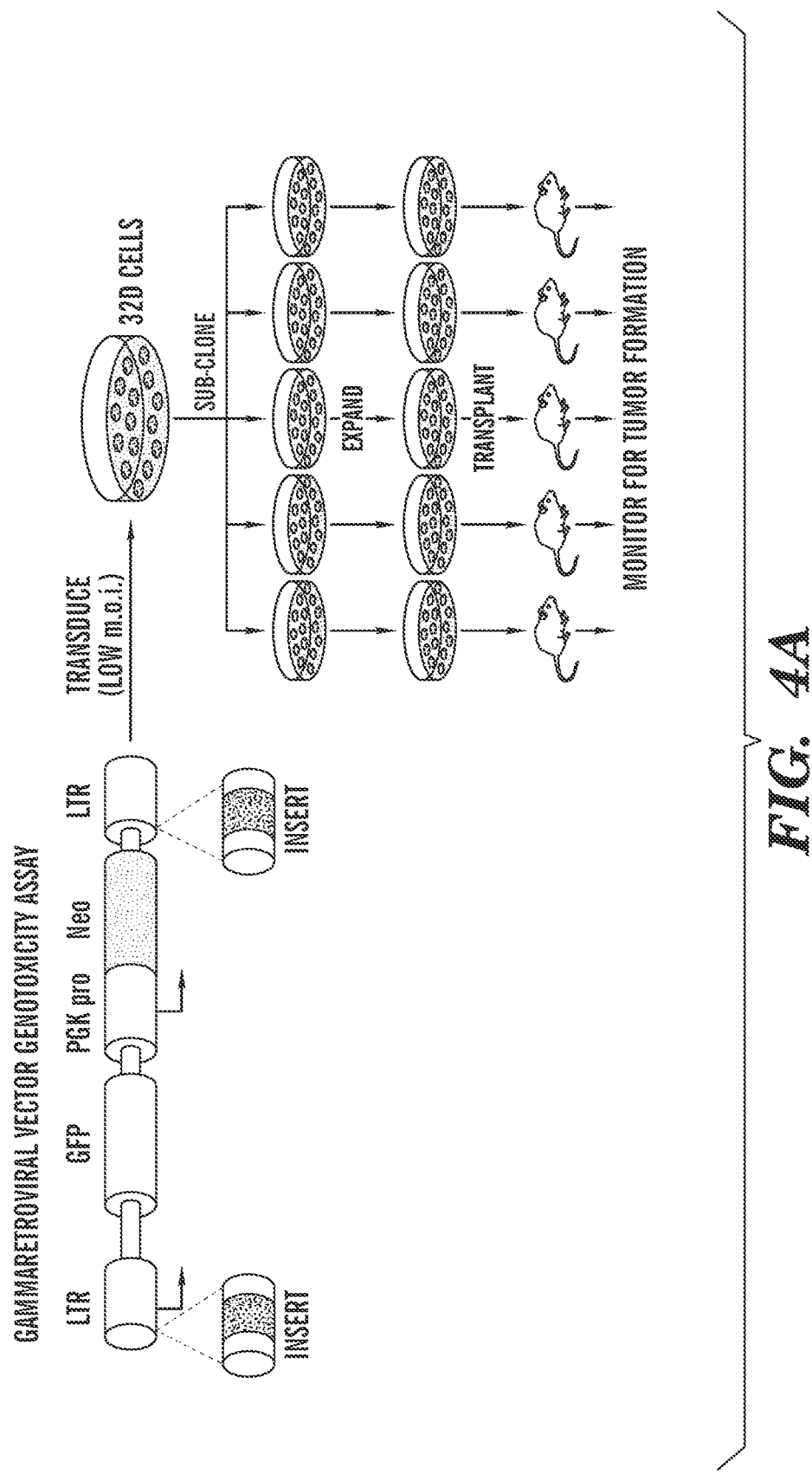
Figure 4B:
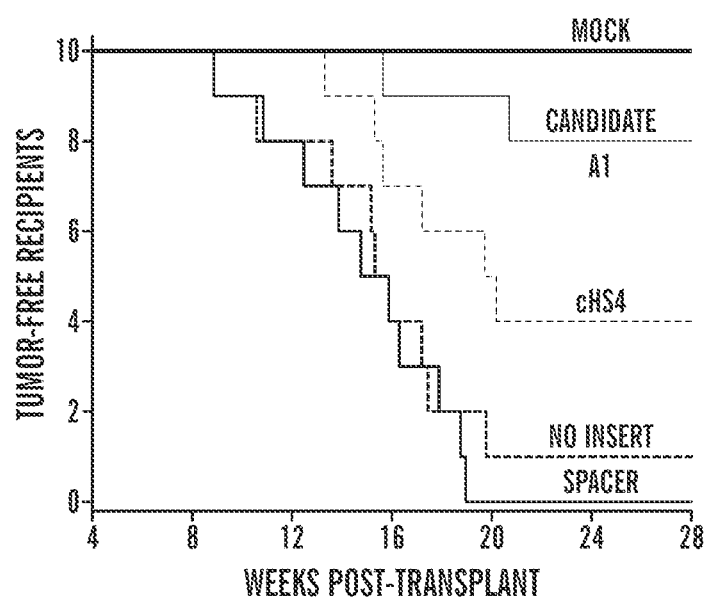

The inventors used insulator A1 to test possible effects on vector-mediated genotoxicity in a tumor transplant genotoxicity assay (24). In this assay a cell line transduced with gamma retroviral vectors produces tumors after transplantation in mice and allows quantitation of genotoxic effects by measuring rates of tumor free survival. Insulator A1 was inserted in the proximal portion of the 3' LTR, from which it is copied into the 5' LTR during reverse transcription and vector integration. The resulting topology (FIG. 4A) is expected to decrease genotoxicity by placing the insulator at both ends of the vector pro-virus, thereby preventing the 5' LTR fully and the 3' LTR partially from interacting with the surrounding genomic region. Vectors flanked with the A1 insulator or control fragments were used to transduce the growth factor-dependent cell line 32D, and 10 independent sub-clones for each vector were transplanted into syngeneic C3H/HeJ mice. All 10 mice transplanted with mock-transduced cells remained free of tumors, while nearly all mice transplanted with 32D cells transduced with vectors containing no inserts or a 790 bp neutral spacer developed tumors within a median of 16 weeks (FIG. 4B). Flanking this vector with the cHS4 insulator delayed the onset of tumor formation by several weeks, and reduced the frequency of animals that developed tumors to 6 of 10. In contrast, only two of 10 animals developed tumors following transplantation with 32D cells transduced with the vector flanked with the insulator A1 (FIG. 4B). Based on the frequency of animals with tumors and the number of vector transduction events in the original sub-pools, the inventors estimate that flanking the vector with insulator A1 reduced the overall rate of tumor formation 15.7-fold, from nearly 47 tumors per $10^5$ provirus to under 3 tumors per $10^5$ provirus (FIG. 4C). In comparison, the cHS4 insulator reduced the overall rate of tumor formation 2.8-fold (to about 17 tumors per $10^5$ provirus), while the neutral spacer had no statistically discernable effect on the rate of tumor formation.

Genotoxicity caused by insertional activation of proto-oncogenes and expressed as hematopoietic malignancy has occurred in several immunodeficient patients treated with gammaretroviral vectors (1,2,32-36). Insights on the mechanisms of genotoxicity were obtained from the extensive analyses of genomic integration patterns in the lymphoid and other hematopoietic cells of SCID-X1 and ADA patients (37-41). It is now clear that the first step in the oncogenic process is the activation of proto-oncogenes and other cellular growth genes by the strong enhancer/promoters of the vectors (37-41). This first step provides the growth advantage to the affected cells leading to clonal expansion. Prevention of this first step is necessary for decreasing the risk of genotoxicity and this can be accomplished by the use of chromatin insulators (6,7). Placement of a chromatin insulator in the LTR of self-inactivating gammaretroviral or lentiviral vectors will bracket the regulatory elements of the vector thus decreasing the probability of activation of nearby genes. The inventors have shown here that all the insulators the inventors identified can block the interactions between enhancers and promoters. The significant reduction of tumors when a gammaretroviral vector was insulated by insulator A1 (FIG. 4) indicates that these insulators will decrease the risks of genotoxicity in the clinical setting. Most studies to date suggest the CTCF gene is expressed very broadly (ENCODE expression data, UCSC Genome Browser), including all hematopoietic stem/progenitor sub-populations analyzed from mice (42, probe set 1418330_at). As such, CTCF-based insulators should be active and provide protection in most stages of hematopoiesis.

Since the pioneering studies by Felsenfeld and his colleagues (8-12) considerable literature has pointed to the role of transcriptional factor CTCF in the function of insulator elements in the genome (43,44). CTCF is a multifunctional genome regulator (13), and one of its functions is the interruption of long-distance interactions. The inventors' study clarifies the relationship between CTCF and its function as insulator. The inventors provide evidence that the frequency with which a CTCF site is occupied by CTCF genome-wide determines the probability that the site will function as an insulator, and that only a minority of CTCF sites function as insulators. Similar approaches can be used to dissect the relationships between other transcriptional factor motifs and their biological functions at the genomic level.

These data can serve as a resource for discovery of potent insulators in the human genome. It is unlikely that the 27 elements functionally analyzed were the most powerful insulators among the 400 elements of the high occupancy classes A to F. Although CTCF is the only known vertebrate enhancer-blocker protein, the binding of other factors is also important for the function of insulator elements (19,45). While not wishing to be bound by theory, co-binding of factors that modulate insulator function may explain the variation in enhancer-blocker potency despite identical CTCF sequence described herein. Thus, the chromatin context of a CTCF site also contributes to its insulating potency.

TABLE 7

Full sequences of the genomic insulator elements

| # | SEQ ID NO. | Sequence | Chr | Chr_start | Chr_end |
|---|---|---|---|---|---|
| A1 | 10 | CTGGTTCTACTCATTACATTCCAATCGTGGCATATCCTCTAAACTTTCTTTTCCCTTCATAAATCCTCTTTCTTTTTTTTCCCCCTCACAGTTTTCCTGAACAGGTTGACTATTAATTGTGTCTGCTTGATGTGGACACCAGGTGGCGCTGGACATCAGATTTGGAGAGGCAGTTGTCTAGGGAACCGGGCTCTGTGCCAGCGCAGGAGGCAGGCTGGCTCTCCTATTCCAGGGATGCTCATCCAGGAAGGAAAGGTTGCATGCTGGACACACTAACCTTGAAGAATTCTTCTGTCTCTCGTCATTTAGAAAGGAAGG | 1 | 75991564 | 75991883 |
| A2 | 11 | AGAGCGAGATTCCGTCTCAAAGAAAAAAAAAGTAATGAAATGAATAAAATGAGTCCTAGAGCCAGTAAATGTCGTAAATGTCTCAGCTAGTCAGGTAGTAAAAGGTCTCAACTAGGCAGTGGCAGAGCAGGATTCAAATTCAGGGCTGTTGTGATGCCTCCGCAGACTCTGAGCGCCACCTGGTGGTAATTTGTCTGTGCCTCTTCTGACGTGGAAGAACAGCAACTAACACACTAACACGGCATTTACTATGGGCCAGCCATTGT | 19 | 41144425 | 41144690 |
| A3 | 12 | AGGGGTTGGTCTCCCTATGTTCCCCAGGCTGGTCTCCAACCCCTGGGCTCAAGCAATGCTCCTGCCTCAACCACCCAAAGTGCTGAGATTACAGGTGTGAACCACTGCGCCCGGCTTCAGAGGAGTTTTGATGCACCAGGTGGCGCTGGTAATTTAAGGTTCTCTCGTGAAATTGGTCTTTTCACCTGGCCAGCATCTTATTCCTTCTTCTGGTAACAGCATCCCATTGTTCTTTGTTGAACCACCTCTCCC | 5 | 91226153 | 91226404 |
| A4 | 13 | TGCTTGTCCTTCCTTCCTGTAACACAGCCATTAAACCAGGAGCATCGCCCTTCCCCGGCCCTCAGGTAAGAGGACCAAATACCGTAGCCGTTTCCAATTTCAGTCCTTTAGCGCCACCTGGTGCTAACTACTCTATCACGCTTTTATCCAATAACTACCTTTGTAAATTTCCTTTCAAAAGTTCTGGCCGGGCGCGGTGGCTCACGCTTGTAATCCCAGCACTTTGTGAGGGGTCAGGAGTTC | 7 | 39519983 | 39520225 |
| A5 | 14 | TCCCACTCCATCACCTTCAAGAATGTTCAAAATCCAGAGATTCTAGGATTCTGTTTCCCAGGACTTGGACGACTCCGTGTCTCCATAGCTCCACCAGGTGGCGCTGCCGGGCCTCGTGACCACTTGGAAAAAGCAGTGTCACCAGAACGCTGCGGAGACCTGCCAGCAGGGGTCACACTGAGGTTGCCTCGTGGTGTCCCTGCCTCTGCAGGTGACCTATGAAATTCCTGGCAGGCCCAGCACAGTGGCTCACGCCTGTAATCCCAGCACTTTGGGTGGCCGAGGCGGGTGGATCACCTGAGGTCAGGAGTTCGAGACCAGCCTGGCCAACATGGTGAAACCCCGTCTCTAC | 9 | 121320130 | 121320481 |
| B1 | 15 | AGGCATGACTGGGAAGAACAAATCACATTTCTCTGTGTACTTAGGGGAGAAAGAATTAATTCAAATGCAGGGTCTGCCGCTTCAGGTCCATTTACGGAAGCCGCAATCCTGCACTATGACCACCAGGGGGAGCGCTAGGCCCATCCCTGCACAGGTAGCTATTTTTAGAGGTTGCTTCTAGCCTGGAGGAAGAAACGAAAGAAATAAAAGACTATGATACTTTTTTTTTTTAACCGGACCAACTTATAAATTATTTGTAAGTCCAATAAAAGGCAATTATCAACATTTCCTACTATTTCAGGAGTAATATATTCTATGTTAGAAAAAGATGCACTTTATTCCATGGCT | 1 | 56831943 | 56832290 |
| B2 | 16 | CAGGGCTCTCCTGCAAATAGGCCCTTGGAGGCCTGGCCTGACGTTTAGGTCCTGAGACAGGTGTGCAGATCAGACCCCTCATGGCAACACCAGGCTTCTGGCTCCAGTCCTTGGAGTCCGTCTGCGTCCCAGCAGCTCCCCCTGGTGGCCAGAAGCAAACGCTTCATGTCTTGCATCTAGAGCCAAAGCATCTCCTACCCCTGGATTCCCATTCCGGAATAGTTTTCAGACCAAGGCTCCTCCGCAAATATGAGTGATGTGTCAGATGAGTGATGAGGGACAGGCCAGGGGCACACACGTCGCATCCACTTCTTGGGGCTCTT | 12 | 107607556 | 107607878 |
| B3 | 17 | CCTCCACAACCCATGAAGTCCACATTCTCTTGCTTCCAGCAGATCTGCACCCTCACCACCATGCTGCCATCTGGCTGGCCCATACCTGGAACAGTCTTGTCTAGCACATTTGCTCAGGAGGGAGAGGAGAGGGGATGGACCAGAGTGATGGGAGCCCAGGGCTGCAGGGCAGCTCCCCCTGGTGGACCCTAGAGGTGGCCCCTCCCACTCCTGGGAGAAGAGAAGCCACACTGTGCATTTCGCAGCCAATCAAAACACAACCCTCCAATAGAGGGCGGAATGGGGTTACCAGAAGCTGGGAAAAGCAGGGGAGGAAATGAAGAGCAGGTGGATGG | 14 | 76784789 | 76785124 |
| B4 | 18 | CTCCCGTGTGGTACCTGAGGCCGGCTCCTGTGGCTCTGAGGGGTCTGCAGCACCCCCTTACATCTGTCCACAGAAGGGCTGGGGAGCAGCTTTCCTGTCCCTCCTGTGAGTGGCCACCAGGGGGAGCGTGGACACAGCTGCCCGTGCAGTGACCACCTGCCCCCCACTCCCGCTACTCCAGCAGCAGCGGCTCCAGCCCTGGACACCCTCCCTGCCCCCACCAGCCTGGTCCTGAGCCAGGTGACCTCCTCCAGCATCC | 20 | 63309573 | 63309832 |

TABLE 7-continued

Full sequences of the genomic insulator elements

| # | SEQ ID NO. | Sequence | Chr | Chr_start | Chr_end |
|---|---|---|---|---|---|
| B5 | 19 | ACAGGGCTGCTTGTACCACTCTGCTGCCTCTGAACTGGGGTCCTGGATTTGT GCCAGTGACCGGGTGGGAAGCCCCTGGCTTGCCCCAGCAGGTCTGGCTTCCT GCAGTGGGGCCAGAAATATGAGCTCTGGCTCCCCCTGGTGGCAAGACCAGAA ACGAGCTCAGCGTGACTGTCCAGTGTCAAAGATGTGGGAGGAAGCAGCGGAG AAACCAAAGGAGGAGGAAGACGCCACCATCACTGTCCCCAGCCATGCAGCCT AAAAGTCACTATCCCTTCCTCTCTTAGAGTCTTTTGGTTCAGTTTCCGC | 22 | 35150568 | 35150876 |
| C1 | 20 | GTCTGAATGGTGGCCGTAGTTTGCAGAGCCCTGGTTTCTTCTTGCCTCTCAG CTTCCAACTTCCCCGTGAGTGCCTGCTCCTTGATGGACTGGACTCTAAGCCC TTCTTTGCAGCAAGCACGATATCAAGCTTTGTCAGTAGAGGGCGCCGGAGGG ACACTGTGGAGGAAGGGGCCTTTTCATGGTCCACAGAGCTCTGTTGTGCAAT TTCTTGTTCCTGTTGCATCTTCTCTTAGGGTATGAACGCGGGGGGACATTC CTGGGGCTTTTCCTCAGCTGTGCACCCAGAATGCATGGTCCCTCGACCACCT CATAGCCCATCCT | 1 | 29793056 | 29793380 |
| C3 | 21 | GTTTCGCATCCACCTTTCATTGCTTGCTCTGTGATAATGGAGAGGGACCCTG TAAACGTGTCCGCCTTGCCACTTTGTGCAATATTTAGCTCCTTCAGTAGAGG GCGCTGCAGGAACATGTCAGGAGGGGGCCTTCTCTTCCGGATTCTGGATTCT GGTATACACTTGGAGCGTGGCATTTGGGGACAGCCACTGGTGCGCAGCCCC ATCAAGTTTTGGTGGCATCCCTGTGGACCATATTCTATTAATCTTCAGTGGT ACCCCTGTGGCAGATCCCCAGTGATTCTTATGGGCACTCAGGGCTAAC | 2 | 16525362 | 16525669 |
| C5 | 22 | AGAAGCACTGCCTGGTAGGATTTCGTAGGAGGAATTCAATCATCAAGTGGGA TGTGGATTGGAAATAGGAAGACATTAGATTAGCGTTTCTTTCAACCCAGTAA GTCTGTGAGTGTCCACGCCACTTATCAATGCATTCTCAGCTCCAAAGGCATC CTCCTTTAACTGCTCTGTGATAATGGAGATGGGCTTTGTAAATATTTCTTAC CAGCTGGCATAATGTAAATCCTTGTCAGTAGAGGGCGCTAGAGAGAGAGAGA CCAGAGGAGAAAAAGTTTTATCTTCCAGATTCTGGGGTGCCTCATCTTTTT GCCTCCTCCAGAGCACAGCTTGCTTTCTCTGTTGCTGGGCTCCTATGCACAT GCTTTCTTTTGAGCTAGGCCCA | X | 150683504 | 150683889 |
| D1 | 23 | TCTTTTGCAATGCTCTTTGGGAAATTATATTAGCCTAATTACTAATTTCCTG GCCCTCAAGGTGACTTGCTTGAACTTGCCACCTTCGCCACTAGGGGGCAGCA TTGGTTTACACAGGGTGAACAAACGTTCAATTCTAAACTAATATTCTTTGGT GGGAAAGTGTGTTCATTTTGGTTTGTTTTGAAGAAGTCACTTCATACCTTTG AACTGGGGTTAAGCTGGTAAAAAATCCACCAGTTCCAATATCCTA TGGAAAAACCCCAAAACCACT | 1 | 162847943 | 162848223 |
| D3 | 24 | GAGACCCTCCACCCCCTACCACAGGGAGGCCTCAGGGATGCGCCCTATGGCC AGAGTGAGGGGAGAGGGCCCTTGAGGGCCACTTTCCACCTTTGGTGTCCTT GACTGGCATGTCCTGCCCTGTTCTCCCGTCGCCACTAGGGGGCAGCCACGCA GCAGGAATTTTACGCCAAGAACTCGCGCTGGACCGAAGGCCTCATCTCGGCC TCCAAGGCTGTGGGCTGGGGAGCCACACAGCTGGTGTAGGTTGCCCTGGGTG GGGGGGGGCAGGGGGCTGCTTCCTGCCAGTTGGAGCAGTTTGGGGTTCAACA G | 12 | 122860281 | 122860593 |
| D4 | 25 | GGCGTGTTTGATTTGCTTTTCTCTAAAGCACTGCTCTGTAAGTTCCTATGGG GGGGGCGGGCAGAGCTGCTAGAAATACAGAAGCATAAGAGAGTAAATAATGG TACCTTCATATGCAAATGTGCTTTTCAGATTGGATCTGTCTGTGCTTGTTTT GAGCTATACCCGGTAAGGCTCCCTCCAGAAACAGAATTCTTGTTTAGCTCCT GGGAGTGTGCAGAATCCACAACAGCCACTAGGGGGCAGGAGGCATGTGTCAT ATATACCGGGCAGTGAGAAAGAGTTAATGCAATTAACTAAGGGGCACTATTT TGTACCCTCAGGCTTGAGAGGCCGCCAAGCTACTCCAGCCTCATACAAGTGG GGAAAGACTTTGACGGAGTTTAGGGTGGACTGGCAGGCTCTCAACCATAGCA GGAGCACTCAAATTTCTCAGCTTATGTGGCAGGCCTCATT | 17 | 16363717 | 16364172 |
| D5 | 26 | CCCCTTTCCCTAAACTGGAGAAAAAGGGGGTGAAGAGGTGCTCGAATCGCCA TCCTCCAACGTAAGTCATCTTGAAGGATGGAGCAGAGCTCCTCCAAGCCAGG CCAAGTCCCCGAGCGCAAGTGCCAAAGCTGCAGCCCATTCGTTACCACGGTG CCTGCTGCCCCCTAGTGGCCGCCACCCTGACATGCAAGAGGAAGATACGGAG CTACCCAACCAGTGGAGAAGGGAAGAGGACTGGGGAAAAC | 17 | 29117153 | 29117400 |
| E1 | 27 | GCCACCTTTGGTCTTGACATTCACTAAGGAGTGGGCCTGGAATAAAACCAGA AATCCCATTCTCAGTCTGCCCCAAGCCCTCCAATTCCGAGGAGCCTGTATG TATAAGCTCGGGCAGGCAAAAGTCGACTGTGAGAACACGCCAGCAGAGGGCG CTGTGGCCCCATCAGTCCCTGCCCACTGAACTCTCCAGAAGGAAAAGCGGCA AGGATGCAAACAAGAAAATCAGACCAGACTGGGAGTCTAGACCCTGCGTCCC ACGCGGTCCCACCATGGCTTCCTCTTTGGAATTTTCAGGGGACCCAGGAAG ACTGACACCGCTGAT | 1 | 178532341 | 178532667 |
| E2 | 28 | AGTTTGCAGGTGGCTTGACTGAAAAAAAAAAAGAAAAAGAAAACACCTACTT TCCTCTCCATGGAAACAGCATGCCAGAAAATTTTGTGGACCCTTGAAATGAG CACACATCTCACTTGCAAAAGCACAGCACCAGCGCCCTCTGCTGTTTCCTGG | 13 | 20924854 | 20925155 |

TABLE 7-continued

Full sequences of the genomic insulator elements

| # | SEQ ID NO. | Sequence | Chr | Chr_start | Chr_end |
|---|---|---|---|---|---|
| | | TTTGATTTAGAACTCAGAGAAGCTACAGTACTTTCTAGACTAAAATACCATG<br>TAGAGTTCAAAATTAATTCTAGATTAGACATAGGCAAGCACATTTATA<br>TTAGTACATTCTGTAGTATATTCCAGAGTGAAGGAAATCAAA | | | |
| E3 | 29 | CACCCCCTTACTCCACTCAACCCCTCATTCCTTTAGGCAAGGTATTAAGAGC<br>CCTATGCAAAGGCAATCTTCAAGTATGCGTTGGCAGAAAAACAACCAGTACA<br>AATTGAGGCATAATGTAAAACCGTTAGGCTGCTTTTCACCCAGCAGAGGGCG<br>CTAAACAGCTGTGCCCAAGCCTCTGATTCAACAAAGCAAACGAGGGCTGGTG<br>AAGCAAGGGAAAGTCAGTTCAGACGCAAAAGCAGCTCTACAATTGTCTCCCT<br>TAATCTCCTAGTCAGTTCAGAAAGGCAGAGATTTATTGTTTAGTTCCACAGA<br>GAGAGACTGACCTAAAAACCAAGTGAAGAATATTTAGGATCATTTCAG<br>ACCATTTAAGCCAGCC | 14 | 69129300 | 69129679 |
| E4 | 30 | TGGAATTTGTGTTGACATTGAAACTTCTTACTGTAAATATTACTTTGAATAG<br>TACCTATTTAATCCTGCTCACATTTAATGTCATATTAGGGAACGTCCTTTCT<br>ATAGAATTTTTAACAATTCCCTTTAAAAAGGGATTCTGAAGGTTTTCTTCTC<br>TCACTCTTCTCCATTCTCATAAATATGTTTCTATATGTTTTAAGTCTTAGGC<br>ATATCGGACATCACTAGTGCATCAGCGCCCTCTGCTGGTTCAGTAAGAATGG<br>TTTCCCCATATACTGGGCAAAACTGGATTTTTGTGGTGATGAAAGGGAAAAA<br>AACAAATTCAGTACAATTGGAAAGCTGGTGTTGTTTTAAAACTCTTGAAAAA<br>CACTGAATAAAAGGAATCACACTAAAACTATATGTTGCAATGTTGTTGGTTA<br>AACTTATTAATAACAGTGGGTTAGGAAATATGCATTGGCACATTCTTTTGA | 5 | 64784363 | 64784830 |
| E5 | 31 | TGCATTTCAGGACACAGTGATATTTCAAGGTAAAATATTACAGATTCTGTTT<br>TATTTCAGGTTATAAGCCAAGATATGGTGTAGACCCTTTCTCAATTATTTTA<br>CTATGTTTTAAGCTGAAATCCACCCAGCATATCACAAACCTTTCCTGCGCTT<br>TAGGACTTTAGATTGACAGCGCCCTCTGCTGTAACTCTGAGTTTGTCACACT<br>ATTCTAAACCTCACTAAGAGTCAGCACGGAGACAGACACATCCCTGCTGAAA<br>CGGATCTCCAGGTCAGGATCAGCTCCTCAGCTTTTAGGGTTTGAACCCAAAT<br>ACTGACAGTAACTCAAATCCGGGCAGGCTCTGGGGACCAGTGTTCACTGACT<br>GACTGCCAGGATTTTTCTTTCCATCCCACCCTCTCCCCTGAGTTCCTGGGCG<br>CCTGCATTCAGACCCTTAGACGATATATAATGGGCATTTTAAATTTAGCACT<br>TCCCAACCCGACCTCTTGACTCCACCACTCTCAGCCCAAGTGT | 5 | 171342373 | 171342883 |
| F1 | 32 | CCTTCAAGCCGTTCATCATTTTCTCCAACCGCCATGAAATCCGGCGCATCGA<br>TCTTCACAAAGGAGACTACAGCGTCCTGGTGCCCGGCCTGCGCAACACCATC<br>GCCCTGGACTTCCACCTCAGCCAGAGCGCCCTCTACTGGACCGACGTGGTGG<br>AGGACAAGATCTACCGCGGGAAGCTGCTGGACAACGGAGGTGACCACCGATT<br>GCTGCCAGGCAGGATGCACACAGGCGGAGCGCTCAGGCGCTAGGGGCCACAG<br>GTCCCATCCAAGTGGCCCCAAAGCAGAGGCTTGGCTCCCCCATCCCCCACAC<br>TTCTGTTC | 12 | 57175912 | 57176231 |
| F2 | 33 | TGCCTTTCAGCTCCAAATCTACCCTTATATTACCTGTTCTGAAATAACAGAC<br>AAGACTCTTTGAAGTCTTTCCTCTGTAGTAAGCATGATGCTAAGTTTGTCAG<br>TAGAGGGCGCTGGAGGGCCGTGGCAGGAGGAAGGAGTTTCCTTTCACGGTTC<br>CAGTAAGTTGCAGGTTTTTTGCTTCTTGCTCTTTCTGCGTTGCTGCCAAACT<br>GCACTGTCCCAGCCATGCACCCAGACTGTGCTGCCTGACTTCCTGCAAACTC<br>AAGGCCCCATCTTAGCTCAGTAATCACCTCACTGTGGCCC | 12 | 59113827 | 59114126 |
| F3 | 34 | GGTCAGCCACTGAGGAACTCTGGGTGCACCGCTGGGGCAGAGCATCCCTGAA<br>CAGACCCTGCAGCAGCAGCAAAGGAACACGCAGCAGCAGCAGCACACTGCAC<br>CCTGGAGGCAGAAAGAGGAGTTCCCGCCTCCCACCGTGTCCCGCCAGCGCCC<br>TCTACTGGCAAAACTTAACATCGACCTGTGAAGGAGAAACTCACAGGATGGC<br>AGAGCCGGGGAGCTGAGATGTTAAGAAATCGACCATTCTGCCTCTGCCACTA<br>GCCTCATTTAACTTATCCTCGGGACTTTAGTCTCCTGTAAAATGAAAGGGTT<br>GGGTGAGATTG | 12 | 103632628 | 103632950 |
| F4 | 35 | TCGGACATTTCCCTGTCTCTTAAACCCAGTTTTGCCGCTTTGTCCTGTCTTG<br>GATTCCGCACGCTGCACAAAAAATGGCCAGTAGAGGGCGCTGCTGGCTTACT<br>TTTTAGAAAACTGCTCACAGCCTGATTTCAGCACTTTCAAAAACATGGAAAT<br>TATCTTAATTCAGTCAAAGCAATCAGAACGAGAAAACTGTCTTAAATTCATC<br>AAAGTTGTTTCTTTGTGTCTTTTTCTATTTCGTTTCCCCAAAGGCATCAATA | 7 | 95916685 | 95916944 |
| F5 | 36 | TGGCTCAGTCATGGCTACTGAACGGCGGACAAGTTGCTGTGATGCCATAATG<br>GTGAAACTTGCTAGAAATCAGTCCTGTAGGGTGCTGGGGAAAGCTGTTTATG<br>GGAAGATGTCTCACTACCGCGCCTTGGCTACAAACCACCTTAGGAGGTTGCA<br>GGGGAAAGCCACTGGCCACTGAGTGTTGCTGGCTGTGTATGGCAGCAGGAGG<br>GCCCTGGAGAACCTGTGAGCCAAAGGCGCTGGGGGCAGCGAAACCACGCGC<br>CCCTGCCAACCCCGCTGAGACTCACCGAGCCGGAGGCAAAACTCTTTCTCC | 8 | 70088420 | 70088962 |

TABLE 7-continued

Full sequences of the genomic insulator elements

| SEQ ID NO. | Sequence | Genomic sequences |  |  |
|---|---|---|---|---|
| # |  | Chr | Chr_start | Chr_end |
|  | TGCAATGTTTCTCGAGCGCCCTCTACTGGCAAAACTTCGGTGCCAACGGCAA ATTCTTGAAAAGGTTCAGATTTATTTTCGCAAAGCAGTCAAATAAGGTGAAT TCAGAGGTGAGAGGCAATAAATCAATAACTGGTATAGAGTCCAACAGGTAAA TAAACCCAAACCTTTTATTCTTGCAAATCTAGGCTTCGTTTCCTTGTTTTTA AAATGGTGGGAGAAGTAGGGAAA |  |  |  |

REFERENCES

1. Hacein-Bey-Abina, S. et al. Efficacy of Gene therapy for X-linked severe combined immunodeficiency. N. Engl. J. Med. 363, 355-364 (2010).
2. Aiuti, A. et al. Gene therapy for immunodeficiency due to adenosine deaminase deficiency. N. Engl. J. Med. 360, 447-458 (2009).
3. Cartier, N. et al. Hematopoietic stem cell gene therapy with a lentiviral vector in X-linked adrenoleu-kodystrophy. Science. 326, 818-823 (2009).
4. Cavazzana-Calvo, M. et al. Transfusion independence and HMGA2 activation after gene therapy of human β-thalassaemia. Nature. 467, 318-322 (2010).
5. Baum, C., Modlich, U., Göhring, G. & Schlegelberger, B. Concise review: managing genotoxicity in the therapeutic modification of stem cells. Stem Cells. 29, 1479-1484 (2011).
6. Nienhuis, A. W., Dunbar, C. E. & Sorrentino, B. P. Genotoxicity of retroviral integration in hematopoietic cells. Mol. Ther. 13, 1031-1049 (2006).
7. Emery, D. W. The use of chromatin insulators to improve the expression and safety of integrating gene transfer vectors. Hum. Gene Ther. 22, 761-774 (2011).
8. Gaszner, M. & Felsenfeld, G. Insulators: exploiting transcriptional and epigenetic mechanisms. Nat. Rev. Genet. 7, 703-713 (2006).
9. Chung, J. H., Bell, A. C. & Felsenfeld, G. Characterization of the chicken beta-globin insulator. Proc. Natl. Acad. Sci. USA. 94, 575-580 (1997).
10. Chung, J. H., Whiteley, M. & Felsenfeld, G. A 5' element of the chicken beta-globin domain serves as an insulator in human erythroid cells and protects against position effect in Drosophila. Cell. 74, 505-514 (1993).
10. Bell, A. C., West, A. G. & Felsenfeld, G. The protein CTCF is required for the enhancer blocking activity of vertebrate insulators. Cell. 98, 387-396 (1999).
11. Burgess-Beusse, B. et al. The insulation of genes from external enhancers and silencing chromatin. Proc. Natl. Acad. Sci. USA. 99, 16433-16437 (2002).
12. Phillips, J. E. & Corces, V. G. CTCF: master weaver of the genome. Cell. 137, 1194-1211 (2009).
13. Giles, K. E., Gowher, H., Ghirlando, R., Jin, C. & Felsenfeld, G. Chromatin boundaries, insulators, and long-range interactions in the nucleus. Cold Spring Harb. Sym. 75, 79-85 (2010).
14. Kim, T. H. et al. Analysis of the vertebrate insulator protein CTCF-binding sites in the human genome. Cell. 128, 1231-1245 (2007).
15. Wang, H. et al. Widespread plasticity in CTCF occupancy linked to DNA methylation. Genome Res. 22, 1680-1688 (2012).
16. Schmidt, D. et al. Waves of retrotransposon expansion remodel genome organization and CTCF binding in multiple mammalian lineages. Cell. 148, 335-348 (2012).
17. Parelho, V. et al. Cohesins functionally associate with CTCF on mammalian chromosome arms. Cell. 132, 422-433 (2008).
18. Dixon, J. R. et al. Topological domains in mammalian genomes identified by analysis of chromatin interactions. Nature. 485, 376-380 (2012).
19. Emery, D. W., Yannaki, E., Tubb, J. & Stamatoyannopoulos, G. A chromatin insulator protects retro-virus vectors from chromosomal position effects. Proc. Natl. Acad. Sci. USA. 97, 9150-9155 (2000).
20. Arumugam, P. I. et al. Improved human β-globin expression from self-inactivating lentiviral vectors carrying the chicken hypersensitive site-4 (cHS4) insulator element. Mol. Ther. 15, 1863-1871 (2007).
21. Ryu, B. Y., Persons, D. A., Evans-Galea, M. V., Gray, J. T. & Nienhuis, A. W. A chromatin insulator blocks interactions between globin regulatory elements and cellular promoters in erythroid cells. Blood Cell. Mol. Dis. 39, 221-228 (2007).
22. Uchida, N, Hanawa, H, Yamamoto, M., & Shimada, T. The chicken hypersensitivity site 4 core insulator blocks promoter interference in lentiviral vectors. Hum. Gene. Ther. Meth. 24, 117-124 (2013).
23. Li, C. L., Xiong, D., Stamatoyannopoulos, G., & Emery, D. W. Genomic and functional assays demonstrate reduced gammaretroviral vector genotoxicity associated with use of the cHS4 chromatin insulator. Mol. Ther. 17, 716-724 (2009).
24. Ryu, B. Y. et al. An experimental system for the evaluation of retroviral vector design to diminish the risk for proto-oncogene activation. Blood. 111, 1866-1875 (2008).
25. Evans-Galea, M. V. et al. Suppression of clonal dominance in cultured human lymphoid cells by addition of the cHS4 insulator to a lentiviral vector. Mol. Ther. 15, 801-809 (2007).
26. Renda, M. et al. Critical DNA binding interactions of the insulator protein CTCF: a small number of zinc fingers mediate strong binding, and a single finger-DNA interaction controls binding at imprinted loci. J. Biol. Chem. 282, 33336-33345 (2007).
27. Wendt, K. S. et al. Cohesin mediates transcriptional insulation by CCCTC-binding factor. Nature. 451, 796-801 (2008).
28. Ohlsson, R., Renkawitz, R. & Lobanenkov, V. CTCF is a uniquely versatile transcription regulator linked to epigenetics and disease. Trends Genet. 17, 520-527 (2001).
29. Nakahashi, H. et al. A genome-wide map of CTCF multivalency redefines the CTCF code. Cell Rep. 3, 1678-1698 (2013).

30. Li, G. et al. Extensive promoter-centered chromatin interactions provide a topological basis for transcription regulation. *Cell.* 148, 84-98 (2012).
31. Baum, C. Gene therapy for SCID-X1: focus on clinical data. *Mol. Ther.* 19, 2013-2014 (2011).
32. Kohn, D. B. & Candotti, F. Gene therapy fulfilling its promise. *N. Engl. J. Med.* 360, 518-521 (2009).
33. Stein, S. et al. Genomic instability and myelodysplasia with monosomy 7 consequent to EVI1 activation after gene therapy for chronic granulomatous disease. *Nat. Med.* 16, 198-204 (2010).
34. Dunbar, C. E. & Larochelle, A. Gene therapy activates EVI1, destabilizes chromosomes. *Nat. Med.* 16, 163-165 (2010).
35. Galy, A. & Thrasher, A. J. Gene therapy for the Wiskott-Aldrich syndrome. *Curr. Opin. Allergy CL.* 11, 545-550 (2011).
36. Schwarzwaelder, K. et al. Gammaretrovirus-mediated correction of SCID-X1 is associated with skewed vector integration site distribution in vivo. *J. Clin. Invest.* 117, 2241-2249 (2007).
37. Deichmann, A et al. Vector integration is nonrandom and clustered and influences the fate of lymphopoiesis in SCID-X1 gene therapy. *J. Clin. Invest.* 117, 2225-2232 (2007).
38. Aitui, A. et al. Multilineage hematopoietic reconstitution without clonal selection in ADA-SCID patients treated with stem cell gene therapy. *J. Clin. Invest.* 117, 2233-2240 (2007).
39. Howe, S. J. et al. Insertional mutagenesis combined with acquired somatic mutations causes leukemogenesis following gene therapy of SCID-X1 patients. *J. Clin. Invest.* 118, 3143-3150 (2008).
40. Hacein-Bay-Abina, S. H. et al. Insertional oncogenesis in 4 patients after retrovirus-mediated gene therapy of SCID-X1. *J. Clin. Invest.* 118, 3132-3142 (2008).
41. Seita. J. et al. Gene Expression Commons: an open platform for absolute gene expression profiling. *PLoS One.* 7, e40321 (2012).
42. Song, L. et al. Open chromatin defined by DNaseI and FAIRE identifies regulatory elements that shape cell-type identity. *Genome Res.* 21, 1757-1767 (2011).
43. Xi, H. et al. Identification and characterization of cell type-specific and ubiquitous chromatin regulatory structures in the human genome. *PLoS Genet.* 3, 1377-1388 (2007).
44. Dickson, J. et al. VEZF1 elements mediate protection from DNA methylation. *PLoS Genet.* 6, e1000804 (2010).
45. Kharchenko, P. V., Tolstorukov, M. Y., Park. P. J. Design and analysis of ChIP-seq experiments for DNA-binding proteins. *Nat. Biotechnol.* 26, 1351-1359 (2008).
46. Neph, S. et al. BEDOPS: high-performance genomic feature operations. *Bioinformatics.* 28, 1919-1920 (2012).
47. Thurman, R. E. et al. The accessible chromatin landscape of the human genome. *Nature.* 489, 75-82 (2012).
48. Tubb, J., Groth, A. C., Leong, L., Emery, D. W. Simultaneous sequence transfer into two independent locations of a reporter vector using MultiSite Gateway technology. *Biotechniques.* 39, 553-557 (2005).
49. Aker, M. et al. Core sequences from the cHS4 insulator are necessary for protecting retroviral vectors from silencing position effects. *Hum. Gene. Ther.* 18, 333-343 (2007).
50. Grant, C. E., Bailey, T. L., Noble, W. S. FIMO: scanning for occurrences of a given motif. *Bioinformatics.* 27, 1017-1018 (2011).
51. Jolma, A. et al. DNA-binding specificities of human transcription factors. Cell. 152, 327-339 (2013). Matys, V. et al. TRANSFAC and its module TRANSCompel: transcriptional gene regulation in eukaryotes. *Nucleic Acids Res.* 34, D108-110 (2006).
52. Nakahashi, H. et al. A genome-wide map of CTCF multivalency redefines the CTCF code. *Cell Rep.* 3, 1678-1698 (2013).
53. Neph, S. et al. An expansive human regulatory lexicon encoded in transcription factor footprints. *Nature.* 489, 83-90 (2012).
54. Newburger, D. E. & Bulyk, M. L. UniPROBE: an online database of protein binding microarray data on protein-DNA interactions. *Nucleic Acids Res.* 37, D77-82 (2009).
55. Portales-Casamar, E. et al. JASPAR 2010: the greatly expanded open-access database of transcription factor binding profiles. *Nucleic Acids Res.* 38, D105-110 (2010).

The invention claimed is:

1. A viral vector comprising: a cassette comprising a nucleic acid sequence encoding a therapeutic agent driven by a promoter regulated by an enhancer,
wherein the cassette is bracketed by genomic insulator elements,
wherein each of the genomic insulator elements comprises a CTCF binding site core sequence selected from the group consisting of:

```
                            (SEQ ID NO.: 2)
CCACCAGGGGGAGC, (SEQ ID NO.: 3)
TCAGTAGAGGGCGC, (SEQ ID NO.: 4)
CCACTAGGGGGCAG, (SEQ ID NO.: 5)
CAGCAGAGGGCGCT,
and (SEQ ID NO.: 6)
CAGTAGAGGGCGCT.
```

2. The viral vector of claim 1, wherein the viral vector is a retroviral vector or a lentiviral vector.

3. The viral vector of claim 1, wherein the CTCF binding site core sequence is CCACCAGGGGGAGC (SEQ ID NO: 2).

4. The viral vector of claim 1, wherein the CTCF binding site core sequence is TCAGTAGAGGGCGC (SEQ ID NO: 3).

5. The viral vector of claim 1, wherein the CTCF binding site core sequence is CCACTAGGGGGCAG (SEQ ID NO: 4).

6. The viral vector of claim 1, wherein the CTCF binding site core sequence is CAGCAGAGGGCGCT (SEQ ID NO: 5).

7. The viral vector of claim 1, wherein the CTCF binding site core sequence is CAGTAGAGGGCGCT (SEQ ID NO.: 6).

8. The viral vector of claim 1, wherein each of the genomic insulator elements comprises 150 to 250 nucleotides.

9. The viral vector of claim 1, wherein each of the genomic insulator elements comprises 119 to 284 nucleotides.

10. A method for administering the therapeutic agent, the method comprising administering the viral vector of claim 1 to a subject in need thereof.

11. The method of claim 10, wherein the viral vector is a retroviral vector or a lentiviral vector.

12. The method of claim 10, wherein the CTCF binding site core sequence is CCACCAGGGGGAGC (SEQ ID NO: 2).

13. The method of claim 10, wherein the CTCF binding site core sequence is TCAGTAGAGGGCGC (SEQ ID NO: 3).

14. The method of claim 10, wherein the CTCF binding site core sequence is CCACTAGGGGGCAG (SEQ ID NO: 4).

15. The method of claim 10, wherein the CTCF binding site core sequence is CAGCAGAGGGCGCT (SEQ ID NO: 5).

16. The method of claim 10, wherein the CTCF binding site core sequence is CAGTAGAGGGCGCT (SEQ ID NO: 6).

17. The method of claim 10, wherein each of the genomic insulator elements comprises 150 to 250 nucleotides.

18. The method of claim 10, wherein each of the genomic insulator elements comprises 119 to 284 nucleotides.

19. A viral vector comprising a cassette comprising a nucleic acid sequence encoding a therapeutic agent driven by a promoter regulated by an enhancer, wherein the cassette is bracketed by genomic insulator elements, and wherein each of the genomic insulator elements comprises a CTCF binding site core sequence of SEQ

```
                            (SEQ ID NO.: 1)
CACCAGGTGGCGCT.
```

20. The viral vector of claim 19, wherein the viral vector is a retroviral vector or a lentiviral vector.

21. The viral vector of claim 19, wherein each of the genomic insulator elements comprises 150 to 250 nucleotides.

22. The viral vector of claim 19, wherein each of the genomic insulator elements comprises 119 to 284 nucleotides.

23. A method for administering the therapeutic agent, the method comprising administering the viral vector of claim 19 to a subject in need thereof.

24. The method of claim 23, wherein the viral vector is a retroviral vector or lentiviral vector.

25. The method of claim 23, wherein each of the genomic insulator elements comprises 150 to 250 nucleotides.

26. The method of claim 23, wherein each of the genomic insulator elements comprises 119 to 284 nucleotides.

* * * * *

SEQUENCE LISTING

```
<160> NUMBER OF SEQ ID NOS: 110

<210> SEQ ID NO 1
<211> LENGTH: 14
<212> TYPE: DNA
<213> ORGANISM: Homo sapiens

<400> SEQUENCE: 1
caccaggtgg cgct                                                        14

<210> SEQ ID NO 2
<211> LENGTH: 14
<212> TYPE: DNA
<213> ORGANISM: Homo sapiens

<400> SEQUENCE: 2
ccaccagggg gagc                                                        14

<210> SEQ ID NO 3
<211> LENGTH: 14
<212> TYPE: DNA
```

<213> ORGANISM: Homo sapiens

<400> SEQUENCE: 3
tcagtagagg gcgc                                                        14

<210> SEQ ID NO 4
<211> LENGTH: 14
<212> TYPE: DNA
<213> ORGANISM: Homo sapiens

<400> SEQUENCE: 4
ccactagggg gcag                                                        14

<210> SEQ ID NO 5
<211> LENGTH: 14
<212> TYPE: DNA
<213> ORGANISM: Homo sapiens

<400> SEQUENCE: 5
cagcagaggg cgct                                                        14

<210> SEQ ID NO 6
<211> LENGTH: 14
<212> TYPE: DNA
<213> ORGANISM: Homo sapiens

<400> SEQUENCE: 6
cagtagaggg cgct                                                        14

<210> SEQ ID NO 7
<211> LENGTH: 14
<212> TYPE: DNA
<213> ORGANISM: Homo sapiens

<400> SEQUENCE: 7
ccctctcctg ggca                                                        14

<210> SEQ ID NO 8
<211> LENGTH: 14
<212> TYPE: DNA
<213> ORGANISM: Homo sapiens

<400> SEQUENCE: 8
gcagcagaga gcaa                                                        14

<210> SEQ ID NO 9
<211> LENGTH: 14
<212> TYPE: DNA
<213> ORGANISM: Homo sapiens

<400> SEQUENCE: 9
ccctctgctg actg                                                        14

<210> SEQ ID NO 10
<211> LENGTH: 320
<212> TYPE: DNA
<213> ORGANISM: Homo sapiens

<400> SEQUENCE: 10
ctggttctac tcattacatt ccaatcgtgg catatcctct aaactttctt ttcccttcat      60
aaatcctctt tctttttttt cccctcaca gtttcctga acaggttgac tattaattgt       120
gtctgcttga tgtggacacc aggtggcgct ggacatcaga tttggagagg cagttgtcta     180

| | |
|---|---|
| gggaaccggg ctctgtgcca gcgcaggagg caggctggct ctcctattcc agggatgctc | 240 |
| atccaggaag gaaaggttgc atgctggaca cactaacctt gaagaattct tctgtctctc | 300 |
| tcgtcattta gaaaggaagg | 320 |

<210> SEQ ID NO 11
<211> LENGTH: 266
<212> TYPE: DNA
<213> ORGANISM: Homo sapiens

<400> SEQUENCE: 11

| | |
|---|---|
| agagcgagat tccgtctcaa agaaaaaaaa agtaatgaaa tgaataaaat gagtcctaga | 60 |
| gccagtaaat gtcgtaaatg tctcagctag tcaggtagta aaaggtctca actaggcagt | 120 |
| ggcagagcag gattcaaatt cagggctgtt gtgatgcctc cgcagactct gagcgccacc | 180 |
| tggtggtaat ttgtctgtgc ctcttctgac gtggaagaac agcaactaac acactaacac | 240 |
| ggcatttact atgggccagc cattgt | 266 |

<210> SEQ ID NO 12
<211> LENGTH: 252
<212> TYPE: DNA
<213> ORGANISM: Homo sapiens

<400> SEQUENCE: 12

| | |
|---|---|
| aggggttggt ctccctatgt tccccaggct ggtctccaac ccctgggctc aagcaatgct | 60 |
| cctgcctcaa ccacccaaag tgctgagatt acaggtgtga accactgcgc ccggcttcag | 120 |
| aggagttttg atgcaccagg tggcgctggt aatttaaggt tctctcgtga aattggtctt | 180 |
| ttcacctggc cagcatctta ttccttcttc tggtaacagc atcccattgt tctttgttga | 240 |
| accacctctc cc | 252 |

<210> SEQ ID NO 13
<211> LENGTH: 243
<212> TYPE: DNA
<213> ORGANISM: Homo sapiens

<400> SEQUENCE: 13

| | |
|---|---|
| tgcttgtcct tccttcctgt aacacagcca ttaaaccagg agcatcgccc ttccccggcc | 60 |
| ctcaggtaag aggaccaaat accgtagccg tttccaattt cagtccttta gcgccacctg | 120 |
| gtgctaacta ctctatcacg cttttatcca ataactacct ttgtaaattt cctttcaaaa | 180 |
| gttctggccg ggcgcggtgg ctcacgcttg taatcccagc actttgtgag gggtcaggag | 240 |
| ttc | 243 |

<210> SEQ ID NO 14
<211> LENGTH: 352
<212> TYPE: DNA
<213> ORGANISM: Homo sapiens

<400> SEQUENCE: 14

| | |
|---|---|
| tcccactcca tcaccttcaa gaatgttcaa aatccagaga ttctaggatt ctgtttccca | 60 |
| ggacttggac gactccgtgt ctccatagct ccaccaggtg gcgctgccgg gcctcgtgac | 120 |
| cacttggaaa aagcagtgtc accagaacgc tgcggagacc tgccagcagg ggtcacactg | 180 |
| aggttgcctc gtggtgtccc tgcctctgca ggtgacctat gaaattcctg gcaggcccag | 240 |
| cacagtggct cacgcctgta atcccagcac tttgggtggc cgaggcgggt ggatcacctg | 300 |

```
aggtcaggag ttcgagacca gcctggccaa catggtgaaa ccccgtctct ac            352
```

<210> SEQ ID NO 15
<211> LENGTH: 348
<212> TYPE: DNA
<213> ORGANISM: Homo sapiens

<400> SEQUENCE: 15

```
aggcatgact gggaagaaca aatcacattt ctctgtgtac ttaggggaga aagaattaat    60
tcaaatgcag ggtctgccgc ttcaggtcca tttacggaag ccgcaatcct gcactatgac   120
caccaggggg agcgctaggc ccatccctgc acaggtagct attttagag gttgcttcta    180
gcctggagga agaaacgaaa gaaataaaag actatgatac ttttttttt taaccggacc    240
aacttataaa ttatttgtaa gtccaataaa aggcaattat caacatttcc tactatttca   300
ggagtaatat attctatgtt agaaaaagat gcactttatt ccatggct                348
```

<210> SEQ ID NO 16
<211> LENGTH: 323
<212> TYPE: DNA
<213> ORGANISM: Homo sapiens

<400> SEQUENCE: 16

```
cagggctctc ctgcaaatag gcccttggag gcctggcctg acgtttaggt cctgagacag    60
gtgtgcagat cagacccctc atggcaacac caggcttctg gctccagtcc ttggagtccg   120
tctgcgtccc agcagctccc cctggtggcc agaagcaaac gcttcatgtc ttgcatctag   180
agccaaagca tctcctaccc ctggattccc attccggaat agttttcaga ccaaggctcc   240
tccgcaaata tgagtgatgt gtcagatgag tgatgaggga caggccaggg gcacacacgt   300
cgcatccact tcttggggct ctt                                            323
```

<210> SEQ ID NO 17
<211> LENGTH: 336
<212> TYPE: DNA
<213> ORGANISM: Homo sapiens

<400> SEQUENCE: 17

```
cctccacaac ccatgaagtc cacattctct tgcttccagc agatctgcac cctcaccacc    60
atgctgccat ctggctggcc catacctgga acagtcttgt ctagcacatt tgctcaggag   120
ggagaggaga gggatggac cagagtgatg ggagcccagg gctgcagggc agctccccct   180
ggtggaccct agaggtggcc cctcccactc ctgggagaag agaagccaca ctgtgcattt    240
cgcagccaat caaaacacaa ccctccaata gagggcggaa tggggttacc agaagctggg   300
aaaagcaggg gaggagaatg aagagcaggt ggatgg                             336
```

<210> SEQ ID NO 18
<211> LENGTH: 260
<212> TYPE: DNA
<213> ORGANISM: Homo sapiens

<400> SEQUENCE: 18

```
ctcccgtgtg gtacctgagg ccggctcctg tggctctgag ggggtctgca gcaccccctt    60
acatctgtcc acagaagggc tggggagcag ctttcctgtc cctcctgtga gtggccacca   120
gggggagcgt ggacacagct gcccgtgcag tgaccacctg cccccactc ccgctactcc    180
agcagcagcg gctccagccc tggacaccct ccctgccccc accagcctgg tcctgagcca   240
ggtgacctcc tccagcatcc                                                260
```

<210> SEQ ID NO 19
<211> LENGTH: 309
<212> TYPE: DNA
<213> ORGANISM: Homo sapiens

<400> SEQUENCE: 19

```
acagggctgc ttgtaccact ctgctgcctc tgaactgggg tcctggattt gtgccagtga      60
ccgggtggga agccctggc ttgccccagc aggtctggct tcctgcagtg gggcagaaa      120
tatgagctct ggctcccct ggtggcaaga ccagaaacga gctcagcgtg actgtccagt      180
gtcaaagatg tgggaggaag cagcggagaa accaaaggag gaggaagacg ccaccatcac      240
tgtccccagc catgcagcct aaaagtcact atcccttcct ctcttagagt cttttggttc      300
agtttccgc                                                               309
```

<210> SEQ ID NO 20
<211> LENGTH: 325
<212> TYPE: DNA
<213> ORGANISM: Homo sapiens

<400> SEQUENCE: 20

```
gtctgaatgg tggccgtagt ttgcagagcc ctggtttctt cttgcctctc agcttccaac      60
ttccccgtga gtgcctgctc cttgatggac tggactctaa gcccttcttt gcagcaagca      120
cgatatcaag ctttgtcagt agagggcgcc ggagggacac tgtggaggaa ggggcctttt      180
catggtccac agagctctgt tgtgcaattt cttgttcctg ttgcatcttc tcttagggta      240
tgaacgcggg gggacatcct ctggggcttt tcctcagctg tgcacccaga atgcatggtc      300
cctcgaccac ctcatagccc atcct                                             325
```

<210> SEQ ID NO 21
<211> LENGTH: 308
<212> TYPE: DNA
<213> ORGANISM: Homo sapiens

<400> SEQUENCE: 21

```
gtttcgcatc cacctttcat tgcttgctct gtgataatgg agagggaccc tgtaaacgtg      60
tccgccttgc cactttgtgc aatatttagc tccttcagta gagggcgctg caggaacatg      120
tcaggagggg gccttctctt ccggattctg gattctggta tacacttgga gcgtggcatt      180
tgggggacag ccactggtgc gcagccccat caagttttgg tggcatccct gtggaccata      240
ttctattaat cttcagtggt acccctgtgg cagatcccca gtgattctta tgggcactca      300
gggctaac                                                                308
```

<210> SEQ ID NO 22
<211> LENGTH: 386
<212> TYPE: DNA
<213> ORGANISM: Homo sapiens

<400> SEQUENCE: 22

```
agaagcactg cctggtagga tttcgtagga ggaattcaat catcaagtgg gatgtggatt      60
ggaaatagga agacattaga ttagcgtttc tttcaaccca gtaagtctgt gagtgtccac      120
gccacttatc aatgcattct cagctccaaa ggcatcctcc tttaactgct ctgtgataat      180
ggagatgggc tttgtaaata tttcttacca gctggcataa tgtaaatcct tgtcagtaga      240
gggcgctaga gagagagaga ccagaggaga aaaaagtttt atcttccaga ttctggggtg      300
```

```
cctcatctttt tgcctcctc cagagcacag cttgctttct ctgttgctgg gctcctatgc    360
acatgctttc ttttgagcta ggccca                                        386

<210> SEQ ID NO 23
<211> LENGTH: 281
<212> TYPE: DNA
<213> ORGANISM: Homo sapiens

<400> SEQUENCE: 23
tcttttgcaa tgctctttgg gaaattatat tagcctaatt actaatttcc tggccctcaa    60
ggtgacttgc ttgaacttgc caccttcgcc actaggggc agcattggtt tacacagggt    120
gaacaaacgt tcaattctaa actaatattc tttggtggga aagtgtgttc attttggttt    180
gttttgaaga agtcacttca tacctttgaa ctggggttaa gctggttaac tcccaaaatt    240
ccaccagttc caatatccta tggaaaaacc ccaaaaccac t                       281

<210> SEQ ID NO 24
<211> LENGTH: 313
<212> TYPE: DNA
<213> ORGANISM: Homo sapiens

<400> SEQUENCE: 24
gagaccctcc accccctacc acagggaggc ctcaggatg cgccctatgg ccagagtgag     60
ggggagaggg cccttgaggg ccactttcca cctttggtgt ccttgactgg catgtcctgc   120
cctgttctcc cgtcgccact agggggcagc cacgcagcag gaattttacg ccaagaactc   180
gcgctggacc gaaggcctca tctcggcctc caaggctgtg ggctggggag ccacacagct   240
ggtgtaggtt gccctgggtg ggggggggca ggggctgct tcctgccagt tggagcagtt   300
tggggttcaa cag                                                      313

<210> SEQ ID NO 25
<211> LENGTH: 456
<212> TYPE: DNA
<213> ORGANISM: Homo sapiens

<400> SEQUENCE: 25
ggcgtgtttg atttgctttt ctctaaagca ctgctctgta agttcctatg ggggggggcgg   60 gcagagctgc tagaaataca gaagcataag agagtaaata atggtacctt catatgcaaa   120
tgtgcttttc agattggatc tgtctgtgct tgttttgagc tatacccggt aaggctccct   180
ccagaaacag aattcttgtt tagctcctgg gagtgtgcag aatccacaac agccactagg   240
gggcaggagg catgtgtcat ataccccggg cagtgagaaa gagttaatgc aattaactaa   300
ggggcactat tttgtacccct caggcttgag aggccgccaa gctactccag cctcatacaa   360
gtggggaaag actttgacgg agtttagggt ggactggcag gctctcaacc atagcaggag   420
cactcaaatt tctcagctta tgtggcaggc ctcatt                             456

<210> SEQ ID NO 26
<211> LENGTH: 248
<212> TYPE: DNA
<213> ORGANISM: Homo sapiens

<400> SEQUENCE: 26
cccctttccc taaactggag aaaaaggggg tgaagaggtg ctcgaatcgc catcctccaa    60
cgtaagtcat cttgaaggat ggagcagagc tcctccaagc caggccaagt ccccgagcgc   120
aagtgccaaa gctgcagccc attcgttacc acggtgcctg ctgccccta gtggccgcca   180
```

```
ccctgacatg caagaggaag atacggagct acccaaccag tggagaaggg aagaggactg      240
gggaaaac                                                              248

<210> SEQ ID NO 27
<211> LENGTH: 327
<212> TYPE: DNA
<213> ORGANISM: Homo sapiens

<400> SEQUENCE: 27
gccacctttg gtcttgacat tcactaagga gtgggcctgg aataaaacca gaaatcccca      60
ttctcagtct gccccaagcc ctccaattcc gagggcgctg tatgtataag ctcgggcagg     120
caaaagtcga ctgtgagaac acgccagcag agggcgctgt ggccccatca gtccctgccc     180
actgaactct ccagaaggaa aagcggcaag gatgcaaaca agaaaatcag accagactgg     240
gagtctagac cctgcgtccc acgcggtccc accatggctt cctctttgga attttcaggg     300
ggacccagga agactgacac cgctgat                                         327

<210> SEQ ID NO 28
<211> LENGTH: 302
<212> TYPE: DNA
<213> ORGANISM: Homo sapiens

<400> SEQUENCE: 28
agtttgcagg tggcttgact gaaaaaaaaa aagaaaaaga aaacacctac tttcctctcc      60
atggaaacag catgccagaa aattttgtgg acccttgaaa tgagcacaca tctcacttgc     120
aaaagcacag caccagcgcc ctctgctgtt tcctggtttg atttagaact cagagaagct     180
acagtacttt ctagactaaa ataccatgta gagttcagga taattatatt ctagattaga     240
cataggcaag cacatttata ttagtacatt ctgtagtata ttccagagtg aaggaaatca     300
aa                                                                    302

<210> SEQ ID NO 29
<211> LENGTH: 380
<212> TYPE: DNA
<213> ORGANISM: Homo sapiens

<400> SEQUENCE: 29
caccccctta ctccactcaa ccccctcattc ctttaggcaa ggtattaaga gccctatgca     60
aaggcaatct tcaagtatgc gttggcagaa aaacaaccag tacaaattga ggcataatgt    120
aaaaccgtta ggctgctttt cacccagcag agggcgctaa acagctgtgc ccaagcctct    180
gattcaacaa agcaaacgag ggctggtgaa gcaagggaaa gtcagttcag acgcaaaagc    240
agctctacaa ttgtctccct taatctccta gtcagttcag aaaggcagag atttattgtt    300
tagttccaca gagagagact gacctgcaaa taatccaagt gaagaatatt taggatcatt    360
tcagaccatt taagccagcc                                                380

<210> SEQ ID NO 30
<211> LENGTH: 468
<212> TYPE: DNA
<213> ORGANISM: Homo sapiens

<400> SEQUENCE: 30
tggaatttgt gttgacattg aaacttctta ctgtaaatat tactttgaat agtacctatt      60
taatcctgct cacatttaat gtcatattag ggaacgtcct ttctatagaa ttttttaacaa    120
```

```
ttcccttta aaagggattc tgaaggtttt cttctctcac tcttctccat tctcataaat    180
atgtttctat atgttttaag tcttaggcat atcggacatc actagtgcat cagcgccctc    240
tgctggttca gtaagaatgg tttccccata tactgggcaa aactggattt ttgtggtgat    300
gaaagggaaa aaaacaaatt cagtacaatt ggaaagctgg tgttgtttta aaactcttga    360
aaaacactga atgaaaggaa tcacactaaa actatatgtt gcaatgttgt tggttaatac    420
ttattaataa cagtgggtta ggaaatatgc attggcacat tcttttga                468

<210> SEQ ID NO 31
<211> LENGTH: 511
<212> TYPE: DNA
<213> ORGANISM: Homo sapiens

<400> SEQUENCE: 31
tgcatttcag gacacagtga tatttcaagg taaaatatta cagattctgt tttatttcag     60
gttataagcc aagatatggt gtagacccett tctcaattat tttactatgt tttaagctga    120 aatccacca gcatatcaca aacctttcct gcgctttagg actttagatt gacagcgccc     180
tctgctgtaa ctctgagttt gtcacactat tctaaacctc actaagagtc agcacggaga    240
cagacacatc cctgctgaaa cggatctcca ggtcaggatc agctcctcag cttttagggt    300
ttgaacccaa atactgacag taactcaaat ccgggcaggc tctggggacc agtgttcact    360
gactgactgc caggattttt cttteccatcc caccctctcc cctgagttcc tgggcgcctg    420
cattcagacc cttagacgat atataatggg catttttaaat ttagcacttc ccaacccgac    480
ctcttgactc caccactctc agcccaagtg t                                    511

<210> SEQ ID NO 32
<211> LENGTH: 320
<212> TYPE: DNA
<213> ORGANISM: Homo sapiens

<400> SEQUENCE: 32
ccttcaagcc gttcatcatt ttctccaacc gccatgaaat ccggcgcatc gatcttcaca     60
aaggagacta cagcgtcctg gtgcccggcc tgcgcaacac catcgccctg gacttccacc    120
tcagccagag cgccctctac tggaccgacg tggtggagga caagatctac cgcgggaagc    180
tgctggacaa cggaggtgac caccgattgc tgccaggcag gatgcacaca ggcggagcgc    240
tcaggcgcta ggggccacag gtcccatcca agtggcccca aagcagaggc ttggctcccc    300 catccccac acttctgttc                                                 320

<210> SEQ ID NO 33
<211> LENGTH: 300
<212> TYPE: DNA
<213> ORGANISM: Homo sapiens

<400> SEQUENCE: 33
tgcctttcag ctccaaatct acccttatat tacctgttct gaaataacag acaagactct     60
ttgaagtctt tcctctgtag taagcatgat gctaagtttg tcagtagagg gcgctggagg    120
gccgtggcag gaggaaggag tttccttca cggttccagt aagttgcagg tttttttgctt    180 cttgctcttt ctgcgttgct gccaaactgc actgtcccag ccatgcaccc agactgtgct    240
gcctgacttc ctgcaaactc aaggccccat cttagctcag taatcacctc actgtggccc    300

<210> SEQ ID NO 34
<211> LENGTH: 323
```

```
<212> TYPE: DNA
<213> ORGANISM: Homo sapiens

<400> SEQUENCE: 34
ggtcagccac tgaggaactc tgggtgcacc gctggggcag agcatccctg aacagaccct      60
gcagcagcag caaaggaaca cgcagcagca gcagcacact gcaccctgga ggcagaaaga     120
ggagttcccg cctcccaccg tgtcccgcca gcgccctcta ctggcaaaac ttaacatcga     180
cctgtgaagg agaaactcac aggatggcag agccggggag ctgagatgtt aagaaatcga     240
ccattctgcc tctgccacta gcctcattta acttatcctc gggactttag tctcctgtaa     300
aatgaaaggg ttgggtgaga ttg                                             323

<210> SEQ ID NO 35
<211> LENGTH: 260
<212> TYPE: DNA
<213> ORGANISM: Homo sapiens

<400> SEQUENCE: 35
tcggacattt ccctgtctct taaacccagt tttgccgctt tgtcctgtct tggattccgc      60
acgctgcaca aaaatggcc agtagagggc gctgctggct tactttttag aaaactgctc     120
acagcctgat ttcagcactt tcaaaaacat ggaaattatc ttaattcagt caaagcaatc     180
agaacgagaa aactgtctta aattcatcaa agttgtttct ttgtgtcttt ttctatttcg     240
tttccccaaa ggcatcaata                                                 260

<210> SEQ ID NO 36
<211> LENGTH: 543
<212> TYPE: DNA
<213> ORGANISM: Homo sapiens

<400> SEQUENCE: 36
tggctcagtc atggctactg aacggcggac aagttgctgt gatgccataa tggtgaaact      60
tgctagaaat cagtcctgta gggtgctggg gaaagctgtt tatgggaaga tgtctcacta     120
ccgcgccttg gctacaaacc accttaggag gttgcagggg aaagccactg gccactgagt     180
gttgctggct gtgtatggca gcaggagggc cctggagaac ctgtgagcca aaggcgctgg     240
gggccagcga aaccacgcgc ccctgccaac cccgctgaga ctccaccgag ccggaggcaa     300 aactcttttct cctgcaatgt ttctcgagcg ccctctactg gcaaaacttc ggtgccaacg     360
gcaaattctt gaaaaggttc agatttattt tcgcaaagca gtcaaataag gtgaattcag     420
aggtgagagg caataaatca ataactggta tagagtccaa caggtaaata aacccaaacc     480
ttttattctt gcaaatctag gcttcgtttc cttgttttta aaatggtggg agaagtaggg     540
aaa                                                                   543

<210> SEQ ID NO 37
<211> LENGTH: 10
<212> TYPE: DNA
<213> ORGANISM: Homo sapiens
<220> FEATURE:
<221> NAME/KEY: misc_feature
<222> LOCATION: (1)..(3)
<223> OTHER INFORMATION: May or may not be present

<400> SEQUENCE: 37 gccrccatgg                                                             10

<210> SEQ ID NO 38
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccaatcgtgg catatcctct                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agagcgagat tccgtctcaa                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aggggttggt ctccctatgt                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgcttgtcct tccttcctgt                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
catcccactc catcaccttc                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aggcatgact gggaagaaca                                                  20

<210> SEQ ID NO 44
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cagggctctc ctgcaaatag                                                 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
cctccacaac ccatgaagtc                                                 20

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctcccgtgtg gtacctgag                                                  19

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
acagggctgc ttgtaccact                                                 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtctgaatgg tggccgtagt                                                 20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtttcgcatc cacctttcat                                                 20

<210> SEQ ID NO 50
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 50
tgaggcagca gctatcctaa g                                               21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agaagcactg cctggtagga                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tcttttgcaa tgctctttgg                                                 20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gagaccctcc accccctac                                                  19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggcgtgtttg atttgctttt                                                 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cccctttccc taaactggag                                                 20

<210> SEQ ID NO 56
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 56
gccacctttg gtcttgacat                                                   20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agtttgcagg tggcttgact                                                   20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58 cacccccttta ctccactcaa                                                  20

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tggaatttgt gttgacattg aa                                                22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgcatttcag gacacagtga                                                   20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccttcaagcc gttcatcatt                                                   20

<210> SEQ ID NO 62
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 62
tgcctttcag ctccaaatct                                                 20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggtcagccac tgaggaactc                                                 20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tcggacattt ccctgtctct                                                 20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tggctcagtc atggctactg                                                 20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tggaattgct gctcagattg                                                 20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gcagcaaaga aaagcaaagg                                                 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 68
tacccatcag gaagctcacc                                       20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tccggagttc aggtctctgt                                       20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggaagctcat ttacccagca                                       20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aagcctgggc tcagtaacaa                                       20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggcaaatctc tgcacctctc                                       20

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccttcctttc taaatgacga gaga                                  24

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
acaatggctg gcccatagta                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggagaggtg gttcaacaaa                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gaactcctga cccctcacaa                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gtagagacgg ggtttcacca                                              20

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agccatggaa taaagtgcat c                                            21

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aagagcccca agaagtggat                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 80
ccatccacct gctcttcatt                                               20

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggatgctgga ggaggtcac                                                19

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gcggaaactg aaccaaaaga                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aggatgggct atgaggtggt                                               20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gttagccctg agtgcccata                                               20

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tgctccaaac ctaccottct t                                             21

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
```

-continued tgggcctagc tcaaaagaaa                    20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
agtggttttg gggtttttcc                    20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ctgttgaacc ccaaactgct                    20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
aatgaggcct gccacataag                    20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gttttcccca gtcctcttcc                    20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
atcagcggtg tcagtcttcc                    20

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
tttgatttcc ttcactctgg aa                                              22
```

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
ggctggctta aatggtctga                                                 20
```

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
tcaaaagaat gtgccaatgc                                                 20
```

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
acacttgggc tgagagtggt                                                 20
```

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

```
gaacagaagt gtgggggatg                                                 20
```

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

```
gggccacagt gaggtgatta                                                 20
```

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

```
caatctcacc caaccctttc                                                 20
```

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
tattgatgcc tttggggaaa                                             20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
tttccctact tctcccacca                                             20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
aaaattagct gggcatggtg                                             20

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aaccctgtca ctgcagctc                                              19

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccatcctgaa tgtgatcgtg                                             20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cacacggctg ttcactttgt                                             20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
atggaagccg ttgttattcg                                              20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
gagcacctgg cactaaaagc                                              20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
gggatgcata ggggaggtat                                              20

<210> SEQ ID NO 108
<211> LENGTH: 30
<212> TYPE: DNA
<213> ORGANISM: Homo sapiens

<400> SEQUENCE: 108
acgtacgtca ccaggtggcg ctacgtacgt                                   30

<210> SEQ ID NO 109
<211> LENGTH: 30
<212> TYPE: DNA
<213> ORGANISM: Homo sapiens

<400> SEQUENCE: 109
cgtacgtaca ccaggtggcg ctcgtacgta                                   30

<210> SEQ ID NO 110
<211> LENGTH: 30
<212> TYPE: DNA
<213> ORGANISM: Homo sapiens

<400> SEQUENCE: 110
gtacgtacca ccaggtggcg ctgtacgtac                                   30